(12) United States Patent
Nakazato et al.

(10) Patent No.: US 7,951,811 B2
(45) Date of Patent: May 31, 2011

(54) PYRROLO[2,3-D]PYRIMIDINE DERIVATIVES SUBSTITUTED WITH A CYCLIC AMINO GROUP

(75) Inventors: Atsuro Nakazato, Tokyo (JP); Taketoshi Okubo, Tokyo (JP); Dai Nozawa, Tokyo (JP); Tomoko Tamita, Tokyo (JP); Ludo E. J. Kennis, Beerse (BE)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 653 days.

(21) Appl. No.: 11/630,042

(22) PCT Filed: Jun. 24, 2005

(86) PCT No.: PCT/JP2005/012152
§ 371 (c)(1),
(2), (4) Date: Jun. 16, 2008

(87) PCT Pub. No.: WO2006/001511
PCT Pub. Date: Jan. 5, 2006

(65) Prior Publication Data
US 2008/0280928 A1 Nov. 13, 2008

(30) Foreign Application Priority Data

Jun. 25, 2004 (JP) ................................. 2004-188128

(51) Int. Cl.
*C07D 487/04* (2006.01)
*A61K 31/519* (2006.01)
*A61P 25/24* (2006.01)
*A61P 25/28* (2006.01)
*A61P 25/16* (2006.01)
*A61P 29/00* (2006.01)

(52) U.S. Cl. ..................... 514/265.1; 544/280; 546/113; 514/300

(58) Field of Classification Search .................. 544/280; 514/262.1, 265.1
See application file for complete search history.

(56) References Cited

U.S. PATENT DOCUMENTS

| 6,187,781 | B1 | 2/2001 | Nakazato et al. |
| 6,600,038 | B1 | 7/2003 | Nakazato et al. |
| 6,852,732 | B2 | 2/2005 | Nakazato et al. |
| 2005/0209253 | A1 | 9/2005 | Nakazato et al. |
| 2007/0060602 | A1 | 3/2007 | Nakazato et al. |
| 2007/0254898 | A1 | 11/2007 | Nakazato et al. |

FOREIGN PATENT DOCUMENTS

| WO | WO 94/13676 A1 | 6/1994 |
| WO | 97/29110 A1 | 8/1997 |
| WO | WO 98/42699 A1 | 1/1998 |
| WO | 98/47903 A1 | 10/1998 |
| WO | WO 99/51597 A1 | 10/1999 |
| WO | WO 99/51599 A1 | 10/1999 |
| WO | WO 99/51600 A1 | 10/1999 |
| WO | WO 00/53604 A1 | 9/2000 |
| WO | WO 02/02549 A1 | 1/2002 |
| WO | WO 2004/058767 A1 | 7/2004 |
| WO | WO 2005/066142 A3 | 7/2005 |
| WO | WO 2005/066178 A1 | 7/2005 |
| WO | WO 2005/066182 A1 | 7/2005 |
| WO | WO 2005/085253 A1 | 9/2005 |
| WO | WO 2006/001501 A1 | 1/2006 |
| WO | WO 2006/001511 A1 | 1/2006 |

OTHER PUBLICATIONS

Vippagunta et. al. (Adv. Drug Delivery Rev., 2001, 48, pp. 3-26).*
Mario Bonamico et al., "Condensation Reactions of Tetracyanoethylene and its Monoanion Promoted by Lewis Acids: Synthesis and Crystal, Moleuclar, and Electronic Structure of a Novel Heterocycle, the 2, 3, 6, 7-Tetracyano-5-(tricyanoethenylimino)-3H-1,4,7b-triazabenzo[i,j]pentalenide Ion", J. Chem. Soc. Perkin Trans. 2, 121-125 (1990).
Sudha R. Vippagunta, et al., "Crystalline Solids", Advanced Drug Delivery Reviews, vol. 48, pp. 3-26, 2001.

* cited by examiner

*Primary Examiner* — Susanna Moore
(74) *Attorney, Agent, or Firm* — Sughrue Mion, PLLC

(57) ABSTRACT

[PROBLEM TO BE SOLVED]
An object of the present invention is to provide an antagonist against CRF receptors and/or an agonist for δ receptors which is effective as a therapeutic or prophylactic agent for diseases in which CRF is considered to be involved, such as depression, anxiety, Alzheimer's disease, Parkinson's disease, Huntington's chorea, eating disorder, hypertension, gastrointestinal diseases, drug dependence, cerebral infarction, cerebral ischemia, cerebral edema, cephalic external wound, inflammation, immunity-related diseases, alopecia, irritable bowel syndrome, sleep disorders, epilepsy, dermatitides, schizophrenia, pain, etc.
[SOLUTION]
A pyrrolopyrimidine or pyrrolopyridine derivative substituted with a cyclic amino group represented by the following a [I]

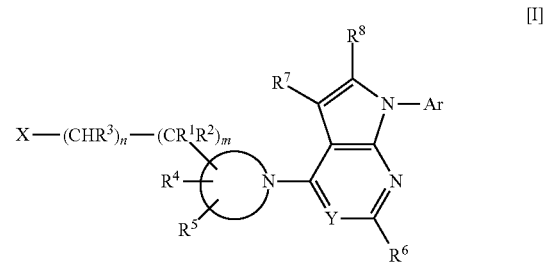

has a high affinity for CRF receptors and/or δ receptors, and is effective against diseases in which CRF is considered to be involved.

8 Claims, No Drawings

PYRROLO[2,3-D]PYRIMIDINE DERIVATIVES SUBSTITUTED WITH A CYCLIC AMINO GROUP

DETAILED DESCRIPTION OF THE INVENTION

1. Technical Field

The present invention relates to a therapeutic agent for diseases in which corticotropin releasing factor (CRF) is considered to be involved, such as depression, anxiety, Alzheimer's disease, Parkinson's disease, Huntington's chorea, eating disorder, hypertension, gastrointestinal diseases, drug dependence, cerebral infarction, cerebral ischemia, cerebral edema, cephalic external wound, inflammation, immunity-related diseases, alopecia, irritable bowel syndrome, sleep disorders, epilepsy, dermatitides, schizophrenia, pain, etc.

2. Description of the Prior Art

CRF is a hormone comprising 41 amino acids (Science, 213, 1394-1397, 1981; and J. Neurosci., 7, 88-100, 1987), and it is suggested that CRF plays a core role in biological reactions against stresses (Cell. Mol. Neurobiol., 14, 579-588, 1994; Endocrinol., 132, 723-728, 1994; and Neuroendocrinol. 61, 445-452, 1995). For CRF, there are the following two paths: a path by which CRF acts on peripheral immune system or sympathetic nervous system through hypothalamus-pituitary-adrenal system, and a path by which CRF functions as a neurotransmitter in central nervous system (in Corticotropin Releasing Factor: Basic and Clinical Studies of a Neuropeptide, pp. 29-52, 1990). Intraventricular administration of CRF to hypophysectomized rats and normal rats causes an anxiety-like symptom in both types of rats (Pharmacol. Rev., 43, 425-473, 1991; and Brain Res. Rev., 15, 71-100, 1990). That is, there are suggested the participation of CRF in hypothalamus-pituitary-adrenal system and the pathway by which CRF functions as a neurotransmitter in central nervous system.

The review by Owens and Nemeroff in 1991 summarizes diseases in which CRF is involved (Pharmacol. Rev., 43, 425-474, 1991). That is, CRF is involved in depression, anxiety, Alzheimer's disease, Parkinson's disease, Huntington's chorea, eating disorder, hypertension, gastrointestinal diseases, drug dependence, inflammation, immunity-related diseases, etc. It has recently been reported that CRF is involved also in epilepsy, cerebral infarction, cerebral ischemia, cerebral edema, and cephalic external wound (Brain Res. 545, 339-342, 1991; Ann. Neurol. 31, 48-498, 1992; Dev. Brain Res. 91, 245-251, 1996; and Brain Res. 744, 166-170, 1997). Accordingly, antagonists against CRF receptors are useful as therapeutic agents for the diseases described above.

Opioid analgesics are well known for their ability to reduce the perception of pain without a loss of consciousness. At least three major types of opioid receptors (δ, μ, κ) are involved in the modulation of a variety of opioid effects. In the field of opioid research, selective agonists for the δ-opioid receptor have shown promising therapeutic potential as analgesics without the adverse side effects associated with morphine and other opioid drugs which are selective for the μ-opioid receptor. There are several lines of evidence showing that stimulation of δ-opioid receptor could alleviate pain process (J. Pharmacol. Exp. Ther. 307, 1079-1089, 2003).

WO02/002549, WO00/053604 and WO04/058767 disclose pyrrolopyridine and pyrrolopyrimidine derivatives as CRF receptor antagonists. However, none disclose the compounds provided in the present invention.

Problem(s) to be Solved by Invention

An object of the present invention is to provide an antagonist against CRF receptors and/or an agonist for δ receptors which is effective as a therapeutic or prophylactic agent for diseases in which CRF is considered to be involved, such as depression, anxiety, Alzheimer's disease, Parkinson's disease, Huntington's chorea, eating disorder, hypertension, gastrointestinal diseases, drug dependence, cerebral infarction, cerebral ischemia, cerebral edema, cephalic external wound, inflammation, immunity-related diseases, alopecia, irritable bowel syndrome, sleep disorders, epilepsy, dermatitides, schizophrenia, pain, etc.

Means for Solving Problem

The present inventors earnestly investigated pyrrolopyrimidine and pyrrolopyridine derivatives substituted with a cyclic amino group that have a high affinity for CRF receptors and/or δ receptors, whereby the present invention has been accomplished.

The present invention is pyrrolopyrimidine and pyrrolopyridine derivatives substituted with a cyclic amino group explained below.

A pyrrolopyrimidine or pyrrolopyridine derivative substituted with a cyclic amino group represented by the following a [I]:

$$X-(CHR^3)_n-(CR^1R^2)_m \begin{array}{c} R^4 \\ R^5 \end{array} N \begin{array}{c} R^7 \\ R^8 \\ N-Ar \\ N \\ Y \\ R^6 \end{array} \quad [I]$$

(wherein the cyclic amino group is represented by the following a [II]:

$$X-(CHR^3)_n-(CR^1R^2)_m \begin{array}{c} R^4 \\ R^5 \end{array} N- \quad [II]$$

in which the cyclic amino group is a 3- to 8-membered saturated cyclic amine or a 3- to 8-membered saturated cyclic amine bridged with $C_{1-5}$alkylene or $C_{1-4}$alkylene-O—$C_{1-4}$alkylene between any different two carbon atoms of the cyclic amine, which cyclic amine is substituted with a group represented by —$(CR^1R^2)_m$—$(CHR^3)_n$—X, $R^4$ and $R^5$ independently on the same or different carbon atoms of the cyclic amine;

X is —$CO_2R^9$, —$CON(R^{10})R^{11}$, —$P(=O)(R^{12})R^{13}$ or —$S(=O)_kR^{14}$;

Y is N or $CR^{15}$;

$R^1$ is hydrogen, hydroxy, $C_{1-5}$alkyl, $C_{1-5}$alkoxy-$C_{1-5}$alkyl or hydroxy-$C_{1-5}$alkyl;

$R^2$ is hydrogen or $C_{1-5}$alkyl;

$R^3$ is hydrogen, cyano, $C_{1-5}$alkyl, $C_{1-5}$alkoxy-$C_{1-5}$alkyl or hydroxy-$C_{1-5}$alkyl;

m is an integer selected from 0, 1, 2, 3, 4 and 5;

n is 0 or 1;

with the proviso that when X is —$CO_2R^9$ or —$CON(R^{10})R^{11}$, and n is 0, then m is an integer selected from 1, 2, 3, 4 and 5;

R$^4$ is hydrogen, hydroxy, hydroxy-C$_{1-5}$alkyl, cyano, cyano-C$_{1-5}$alkyl or C$_{1-5}$alkyl;

R$^5$ is hydrogen or C$_{1-5}$alkyl;

R$^6$ is hydrogen, halogen, C$_{1-5}$alkyl, C$_{3-8}$cycloalkyl, C$_{3-8}$cycloalkyl-C$_{1-5}$alkyl, hydroxy, C$_{1-5}$alkoxy, C$_{3-8}$cycloalkyloxy or —N(R$^{16}$)R$^{17}$;

R$^7$ and R$^8$ are the same or different, and independently are hydrogen, halogen, C$_{1-5}$alkyl, C$_{3-8}$cycloalkyl, C$_{3-8}$cycloalkyl-C$_{1-5}$alkyl, hydroxy, C$_{1-5}$alkoxy, C$_{3-8}$cycloalkyloxy, —N(R$^{18}$)R$^{19}$, —CO$_2$R$^{20}$ cyano, nitro, C$_{1-5}$alkylthio, trifluoromethyl or trifluoromethoxy; or R$^7$ and R$^8$ are taken together to form —CH$_2$—CH$_2$—CH$_2$—CH$_2$— or —CH=CH—CH=CH—;

R$^9$ is hydrogen, C$_{1-20}$alkyl, aryl, C$_{3-8}$cycloalkyl or —CHR$^{1a}$OC(=O)-A$^1$-R$^{1b}$, wherein said C$_{1-20}$alkyl optionally contains one to four double bonds and/or one to four triple bonds, and/or said C$_{1-20}$alkyl is optionally substituted with one of the substituents selected from the group consisting of hydroxy, halogen, cyano, C$_{1-10}$alkoxy, C$_{1-5}$alkoxycarbonyl, C$_{3-8}$cycloalkyl, —C(=O)N(R$^{2a}$)R$^{2b}$, —N(R$^{3a}$)R$^{3b}$ and aryl which aryl is optionally substituted with one or more substituents, which are the same or different, selected from the group consisting of halogen, C$_{1-5}$alkyl and C$_{1-5}$alkoxy;

R$^{1a}$ is hydrogen or C$_{1-5}$alkyl;

A$^1$ is oxygen or a single bond;

R$^{1b}$ is C$_{1-5}$alkyl, C$_{3-8}$cycloalkyl or C$_{3-8}$cycloalkyl-C$_{1-5}$alkyl;

R$^{2a}$ and R$^{2b}$ are the same or different, and independently hydrogen or C$_{1-3}$alkyl;

R$^{3a}$ and R$^{3b}$ are the same or different, and independently hydrogen or C$_{1-3}$alkyl; or R$^{3a}$ and R$^{3b}$ are taken together to form —(CH$_2$)$_s$-A$^2$-(CH$_2$)$_t$—;

A$^2$ is methylene, oxygen, sulfur, NR$^{4a}$ or a single bond;

R$^{4a}$ is hydrogen, C$_{1-5}$alkyl or benzyl;

s and t are the same or different, and independently an integer selected from 1, 2 or 3;

R$^{10}$ is hydrogen, C$_{1-5}$alkyl, C$_{3-8}$cycloalkyl or C$_{3-8}$cycloalkyl-C$_{1-5}$alkyl;

R$^{11}$ is hydrogen, C$_{1-5}$alkyl, C$_{3-8}$cycloalkyl, C$_{3-8}$cycloalkyl-C$_{1-5}$alkyl or —CHR$^{5a}$—(CH$_2$)$_u$—C(=O)R$^{5b}$ or R$^{10}$ and R$^{11}$ are taken together to form —(CH$_2$)$_v$-A$^3$-(CH$_2$)$_w$—;

R$^{5a}$ is hydrogen, C$_{1-5}$alkyl, aryl or heteroaryl, wherein said C$_{1-5}$alkyl is optionally substituted with one of the substituents selected from the group consisting of aryl, heteroaryl, hydroxy, hydroxycarbonyl, 4-hydroxyphenyl, C$_{1-5}$alkoxy, amino, guanidino, mercapto, C$_{1-5}$alkylthio or aminocarbonyl or R$^{10}$ and R$^{5a}$ are taken together to form —(CH$_2$)$_p$—;

p is 3 or 4;

u is 0 or 1;

R$^{5b}$ is hydroxy, C$_{1-5}$alkoxy, benzyloxy or —N(R$^{6a}$)R$^{6b}$;

R$^{6a}$ and R$^{6b}$ are the same or different, and independently hydrogen or C$_{1-3}$alkyl;

v and w are the same or different, and independently an integer selected from 1, 2 or 3;

A$^3$ is methylene, oxygen, sulfur or NR$^{7a}$;

R$^{7a}$ is hydrogen, C$_{1-5}$alkyl or benzyl;

R$^{12}$ and R$^{13}$ are the same or different, and independently are —OR$^{21}$ or —N(R$^{22}$)R$^{23}$;

R$^{14}$ is —OR$^{21}$ or —N(R$^{22}$)R$^{23}$;

k is 1 or 2;

R$^{15}$ is hydrogen, C$_{1-5}$alkyl, halogen, cyano or —CO$_2$R$^{24}$;

R$^{16}$ and R$^{17}$ are the same or different, and independently are hydrogen, C$_{1-5}$alkyl, C$_{3-8}$cycloalkyl or C$_{3-8}$cycloalkyl-C$_{1-5}$alkyl;

R$^{18}$ and R$^{19}$ are the same or different, and independently are hydrogen, C$_{1-5}$alkyl, C$_{3-8}$cycloalkyl or C$_{3-8}$cycloalkyl-C$_{1-5}$alkyl;

R$^{20}$ is hydrogen or C$_{1-5}$alkyl;

R$^{21}$ is hydrogen, C$_{1-5}$alkyl, C$_{3-8}$cycloalkyl or C$_{3-8}$cycloalkyl-C$_{1-5}$alkyl;

R$^{22}$ and R$^{23}$ are the same or different, and independently are hydrogen, C$_{1-5}$alkyl, C$_{3-8}$cycloalkyl or C$_{3-8}$cycloalkyl-C$_{1-5}$alkyl;

R$^{24}$ is hydrogen or C$_{1-5}$alkyl;

Ar is aryl or heteroaryl which aryl or heteroaryl is unsubstituted or substituted with one or more substituents, which are the same or different, selected from the group consisting of halogen, C$_{1-5}$alkyl, C$_{3-8}$cycloalkyl, C$_{2-5}$alkenyl, C$_{2-5}$alkynyl, C$_{1-5}$alkoxy, C$_{1-5}$alkylthio, C$_{1-5}$alkylsulfinyl, C$_{1-5}$alkylsulfonyl, cyano, nitro, hydroxy, —CO$_2$R$^{25}$, —C(=O)R$^{26}$, —CON(R$^{27}$)R$^{28}$, —OC(=O)R$^{29}$, —NR$^{30}$CO$_2$R$^{31}$, —S(O)$_r$N(R$^{32}$)R$^{33}$, trifluoromethyl, trifluoromethoxy, difluoromethoxy, fluoromethoxy, methylenedioxy, ethylenedioxy and —N(R$^{34}$)R$^{35}$;

R$^{25}$ is hydrogen, C$_{1-5}$alkyl, C$_{3-8}$cycloalkyl or C$_{3-8}$cycloalkyl-C$_{1-5}$alkyl;

R$^{26}$ is hydrogen or C$_{1-5}$alkyl;

R$^{27}$ and R$^{28}$ are the same or different, and independently are hydrogen, C$_{1-5}$alkyl, C$_{3-8}$cycloalkyl or C$_{3-8}$cycloalkyl-C$_{1-5}$alkyl;

R$^{29}$ is hydrogen or C$_{1-5}$alkyl;

R$^{30}$ is hydrogen or C$_{1-5}$alkyl;

R$^{31}$ is hydrogen or C$_{1-5}$alkyl;

R$^{32}$ and R$^{33}$ are the same or different, and independently are hydrogen, C$_{1-5}$alkyl, C$_{3-8}$cycloalkyl or C$_{3-8}$cycloalkyl-C$_{1-5}$alkyl;

r is 1 or 2;

R$^{34}$ and R$^{35}$ are the same or different, and independently are hydrogen, C$_{1-5}$alkyl, C$_{3-8}$cycloalkyl or C$_{3-8}$cycloalkyl-C$_{1-5}$alkyl), individual isomers thereof, racemic or non-racemic mixtures of isomers thereof or N-oxide thereof, or pharmaceutically acceptable salts and hydrates thereof.

The terms used in the present specification have the following meanings.

The term "a 3- to 8-membered saturated cyclic amine" means aziridine, azetidine, pyrrolidine, piperidine, azepane or azocane.

The term "C$_{1-5}$alkylene" means a straight or branched chain alkylene of 1 to 5 carbon atoms, such as methylene, ethylene, propylene, trimethylene, tetramethylene, pentamethylene or the like.

The term "a 3- to 8-membered saturated cyclic amine bridged with C$_{1-5}$alkylene or C$_{1-4}$alkylene-O—C$_{1-4}$alkylene between any different two carbon atoms of the cyclic amine" includes, for example, 8-azabicyclo[3.2.1]oct-8-yl, 9-azabicyclo[3.3.1]non-9-yl, 7-azabicyclo[2.2.1]hept-7-yl, 3-oxa-7-azabicyclo[3.3.1]non-7-yl and 3-oxa-9-azabicyclo[3.3.1]non-9-yl.

The term "C$_{1-20}$alkyl" means a straight chain or branched chain alkyl group of 1 to 20 carbon atoms, such as methyl, ethyl, propyl, isopropyl, butyl, isobutyl, t-butyl, sec-butyl, pentyl, isopentyl, tridecyl, 3,7,11,15-tetramethyl-hexadecyl or the like.

The term "C$_{1-20}$alkyl optionally contains one to four double bonds and/or one to four triple bonds" includes for example, allyl, 3,7-dimethyl-octa-2,6-dienyl, but-3-ynyl, dodec-11-ynyl or the like.

The term "C$_{1-10}$alkoxy" means a straight chain or branched chain alkoxy group of 1 to 10 carbon atoms, such as methoxy, ethoxy, propoxy, isopropyloxy, butoxy, isobutyloxy, pentyloxy, isopentyloxy, decyloxy, 3,7-dimethyl-octyloxy or the like.

The term "$C_{1-5}$alkoxy-$C_{1-5}$alkyl" means a substituted $C_{1-5}$alkyl group having the above-mentioned $C_{1-5}$alkoxy group as the substituent, such as methoxymethyl, 2-methoxyethyl, 2-ethoxyethyl or the like.

The term "hydroxy-$C_{1-5}$alkyl" means a substituted $C_{1-5}$alkyl group having hydroxy group, such as hydroxymethyl, 1-hydroxyethyl, 2-hydroxyethyl, 1-hydroxypropyl, 2-hydroxypropyl, 3-hydroxypropyl, 4-hydroxybutyl, 5-hydroxypentyl or the like.

The term "cyano-$C_{1-5}$alkyl" means a substituted $C_{1-5}$alkyl group having cyano group, such as cyanomethyl, 1-cyanoethyl, 2-cyanoethyl, 3-cyanopropyl, 4-cyanobutyl, 5-cyanopentyl or the like.

The term "$C_{3-8}$cycloalkyl" means a cyclic alkyl group of 3 to 8 carbon atoms, such as cyclopropyl, cyclobutyl, cyclopentyl, cyclohexyl, cycloheptyl or the like.

The term "$C_{3-8}$cycloalkyl-$C_{1-5}$alkyl" means a substituted $C_{1-5}$alkyl group having the above-mentioned $C_{3-8}$cycloalkyl as the substituent, such as cyclopropylmethyl, cyclopropylethyl, cyclopentylethyl or the like.

The term "$C_{3-8}$cycloalkyloxy" means a cyclic alkoxy group of 3 to 8 carbon atoms, such as cyclopropyloxy, cyclobutyloxy, cyclopentyloxy or the like.

The term "halogen" means fluorine, chlorine, bromine or iodine atom.

The term "aryl" means a monocyclic or bicyclic group of 6 to 12 ring carbon atoms having at least one aromatic ring, such as phenyl, naphthyl or the like.

The term "$C_{1-5}$alkoxycarbonyl" means a carbonyl group having above mentioned $C_{1-5}$alkoxy group, such as methoxycarbonyl, ethoxycarbonyl, t-butoxycarbonyl or the like.

The term "heteroaryl" means a monocyclic or bicyclic group of 5 to 12 ring atoms having at least one aromatic ring having in its ring 1 to 4 atoms which may be the same or different and are selected from nitrogen, oxygen and sulfur, such as pyridyl, pyrimidinyl, imidazolyl, quinolyl, indolyl, benzofuranyl, quinoxalinyl, benzo[1,2,5]thiadiazolyl, benzo[1,2,5]oxadiazolyl or the like.

The term "$C_{2-5}$alkenyl" means a straight chain or branched chain alkenyl group of 2 to 5 carbon atoms, such as vinyl, isopropenyl, allyl or the like.

The term "$C_{2-5}$alkynyl" means a straight chain or branched chain alkynyl group of 2 to 5 carbon atoms, such as ethynyl, prop-1-ynyl, prop-2-ynyl or the like.

The term "$C_{1-5}$alkylthio" means a straight chain or branched chain alkylthio group of 1 to 5 carbon atoms, such as methylthio, ethylthio, propylthio, isopropylthio or the like.

The term "$C_{1-5}$alkysulfinyl" means a straight chain or branched chain alkylsulfinyl group of 1 to 5 carbon atoms, such as methanesulfinyl, ethanesulfinyl or the like.

The term "$C_{1-5}$alkysulfonyl" means a straight chain or branched chain alkylsulfonyl group of 1 to 5 carbon atoms, such as methanesulfonyl, ethanesulfonyl or the like.

The term "aryl or heteroaryl which aryl or heteroaryl is unsubstituted or substituted with one or more substituents, which are the same or different, selected from the group consisting of halogen, $C_{1-5}$alkyl, $C_{3-8}$cycloalkyl, $C_{2-5}$alkenyl, $C_{2-5}$alkynyl, $C_{1-5}$alkoxy, $C_{1-5}$alkylthio, $C_{1-5}$alkylsulfinyl, $C_{1-5}$alkylsulfonyl, cyano, nitro, hydroxy, —$CO_2R^{25}$, —$C(=O)R^{26}$, —$CON(R^{27})R^{28}$, —$C(=O)R^{29}$, —$NR^{30}CO_2R^{31}$, —$S(O)_rN(R^{32})^{33}$, trifluoromethyl, trifluoromethoxy, difluoromethoxy, fluoromethoxy, methylenedioxy, ethylenedioxy and —$N(R^{34})R^{35}$" includes for example, 2,4-dimethylphenyl, 2,6-dimethylphenyl, 2,4-dibromophenyl, 2-bromo-4-isoproylphenyl, 2,4-dichlorophenyl, 2,6-dichlorophenyl, 2-chloro-4-trifluoromethylphenyl, 4-methoxy-2-methylphenyl, 2-chloro-4-trifluoromethoxyphenyl, 4-isopropyl-2-methylthiophenyl, 2,4,6-trimethylphenyl, 4-bromo-2,6-dimethylphenyl, 4-bromo-2,6-diethylphenyl, 4-chloro-2,6-dimethylphenyl, 2,4,6-tribromophenyl, 2,4,5-tribromophenyl, 2,4,6-trichlorophenyl, 2,4,5-trichlorophenyl, 4-bromo-2,6-dichlorophenyl, 6-chloro-2,4-dibromophenyl, 2,4-dibromo-6-fluorophenyl, 2,4-dibromo-6-methylphenyl, 2,4-dibromo-6-methoxyphenyl, 2,4-dibromo-6-methylthiophenyl, 2,6-dibromo-4-isopropylphenyl, 2,6-dibromo-4-trifluoromethylphenyl, 2-bromo-4-trifluoromethylphenyl, 4-bromo-2-chlorophenyl, 2-bromo-4-chlorophenyl, 4-bromo-2-methylphenyl, 4-chloro-2-methylphenyl, 2,4-dimethoxyphenyl, 2,6-dimethyl-4-methoxyphenyl, 4-chloro-2,6-dibromophenyl, 4-bromo-2,6-difluorophenyl, 2,6-dichloro-4-trifluoromethylphenyl, 2,6-dichloro-4-trifluoromethoxyphenyl, 2,6-dibromo-4-trifluoromethoxyphenyl, 2-chloro-4,6-dimethylphenyl, 2-bromo-4,6-dimethoxyphenyl, 2-bromo-4-isopropyl-6-methoxyphenyl, 2,4-dimethoxy-6-methylphenyl, 6-dimethylamino-4-methylpyridin-3-yl, 2-chloro-6-trifluoromethylpyridin-3-yl, 2-chloro-6-trifluoromethoxypyridin-3-yl, 2-chloro-6-methoxypyridin-3-yl, 6-methoxy-2-trifluoromethylpyridin-3-yl, 2-chloro-6-difluoromethylpyridin-3-yl, 6-methoxy-2-methylpyridin-3-yl, 2,6-dimethoxypyridin-3-yl, 4,6-dimethyl-2-trifluoromethylpyrimidin-5-yl, 2-dimethylamino-6-methylpyridin-3-yl, 6-dimethylamino-2-methylpyridin-3-yl, 2,3-dihydrobenzo[1,4]dioxin-5-yl and benzo[1,3]dioxol-4-yl, 5,7-dimethylbenzo[1,2,5]thiadiazol-4-yl, 5,7-dimethylbenzo[1,2,5]oxadiazol-4-yl, 2-isopropoxy-6-trifluoromethylpyridin-3-yl, 2-methoxy-6-methylpyridin-3-yl, 2,6-dimethylpyridin-3-yl, 2-bromo-6-methoxypyridin-3-yl, 2-chloro-6-dimethylaminopyridin-3-yl, 2,6-dichloropyridin-3-yl, 2,4-dimethyl-6-dimethylaminopyridin-3-yl, 2,4,6-trimethylpyridin-3-yl, 2,4,6-trimethylpyrimidin-5-yl, 4,6-dimethyl-2-dimethylaminopyrimidin-5-yl, 5-iodo-3-methylpyridin-2-yl, 3-methyl-5-methylaminopyridin-2-yl, 3-dimethylamino-5-methylpyridin-2-yl, 5-methyl-3-methylaminopyridin-2-yl, 3-chloro-5-methylpyridin-2-yl, 3-amino-5-methylpyridin-2-yl, 5-methyl-3-nitropyridin-2-yl, 5-diethylamino-3-methylpyridin-2-yl, 5-fluoro-3-methylpyridin-2-yl, 5-chloro-3-methylpyridin-2-yl, 5-dimethylamino-3-methylpyridin-2-yl, 5-amino-3-methylpyridin-2-yl, 3-methyl-5-nitropyridin-2-yl, 3-bromo-5-methylpyridin-2-yl, 4-chloro-2,5-dimethoxyphenyl, 4,5-dimethyl-2-methoxyphenyl, 5-fluoro-2,4-dimethylphenyl, 2,4-dimethoxy-5-methylphenyl, 2-chloro-4-methoxy-5-methylphenyl, 2-chloro-5-fluoro-4-methylphenyl, 2-bromo-4,5-dimethoxyphenyl, 2-bromo-5-fluoro-4-methoxyphenyl, 2-chloro-4,5-dimethoxyphenyl, 2,5-dichloro-4-methoxyphenyl, 2,4-dichloro-5-fluorophenyl, 2-chloro-5-fluoro-4-methoxyphenyl, 2,4,5-trichlorophenyl, 2-chloro-5-fluoro-4-methylphenyl, 5-fluoro-4-methoxy-2-methylphenyl, 4,5-dimethoxy-2-methylphenyl, 5-chloro-4-methoxy-2-methylphenyl, 2,4,5-trimethylphenyl, 6-methoxy-4-methylpyridin-3-yl, 4-methoxy-6-methylpyridin-3-yl, 4,6-dimethylpyridin-3-yl, 2-chloro-4-isopropylphenyl, 2-chloro-4-methylphenyl, 4-amino-2-chlorophenyl, 2-chloro-4-dimethylcarbamoylphenyl, 2-chloro-4-methylcarbamoylphenyl, 4-carbamoyl-2-chlorophenyl, 2-chloro-4-methylsulfonylphenyl, 4-carboxy-2-chlorophenyl, 2-chloro-4-iodophenyl, 2-bromo-4-methylthiophenyl, 2-bromo-4-methylsulfinylphenyl, 2-bromo-4-dimethylaminophenyl, 2-bromo-4-methylsulfonylphenyl, 2-bromo-4-cyclopentylphenyl, 2-bromo-4-tert-butylphenyl, 2-bromo-4- propylphenyl, 2-bromo-4-methylphenyl, 2-bromo-4-trifluoromethoxyphenyl, 2-bromo-4-methoxyphenyl, 2-bromo-4-ethoxyphenyl, 4-isopropyl-2-methylsulfonylphenyl, 4-cyclopentyl-2-methylthiophenyl, 4-butyl-2-methylthiophenyl, 4-methoxy-2-methylthiophenyl, 2-methylthio-4-propylphenyl, 2-dimethylamino-4-isopropylphenyl, 2-iodo-4-isopropylphenyl, 2-fluoro-4-methylphenyl, 2,4-difluorophenyl, 2-chloro-4-methoxyphenyl, 2-chloro-4-hydroxyphenyl, 4-cyano-2-methoxyphenyl, 4-bromo-2-methoxyphenyl, 2-methoxy-4-methylphenyl, 4-chloro-2-methoxyphenyl, 2-hydroxy-4-methylphenyl, 4-fluoro-2-methoxyphenyl, 2-hydroxy-4-methylphenyl, 4-cyano-2-methoxyphenyl, 2-chloro-4-methylthiophenyl, 2-methoxy-4-trifluoromethylphenyl, 4-isopropyl-2-methoxyphenyl, 2-chloro-4-cyanophenyl, 2-chloro-4-ethoxycarbonylphenyl, 2-chloro-4-methylaminophenyl, 4-cyano-2-trifluoromethylphenyl, 4-cyano-2-methylphenyl, 2-methyl-4-trifluoromethoxyphenyl, 2-cyano-4-trifluoromethylphenyl, 4-carboxyamino-2-trifluoromethylphenyl, 4-methoxy-2-trifluoromethylphenyl, 4-fluoro-2-methylphenyl, 4-hydroxy-2-methylphenyl, 4-methoxy-2-methoxycarbonylphenyl, 2-ethyl-4-methoxyphenyl, 2-formyl-4-methoxyphenyl, 4-chloro-2-trifluoromethylphenyl, 4-dimethylamino-2-trifluoromethylphenyl, 4-difluoromethoxy-2-methylphenyl, 2-cyano-4-methoxyphenyl, 4-hydroxy-2-trifluoromethylphenyl, 4-isopropyl-2-trifluoromethylphenyl, 4-diethylamino-2-methylphenyl, 4-fluoro-2-trifluoromethylphenyl, 4-propoxy-2-trifluoromethylphenyl, 4-dimethylamino-2-methylthiophenyl, 4-isopropyl-2-isopropylthiophenyl, 2-ethylthio-4-isopropylphenyl, 4-methylamino-2-methylthiophenyl, 2-methylthio-4-propionylphenyl, 4-acetyl-2-methylthiophenyl, 4-cyano-2-methylthiophenyl, 4-methoxy-2-methylthiophenyl, 4-ethyl-2-methylthiophenyl, 4-bromo-2-methylthiophenyl, 4-isopropyl-2-methylsulfinylphenyl, 2,4-dimethylthiophenyl, 4,6-dimethyl-2-isopropylphenyl, 4,6-dimethyl-2-isopropenylphenyl, 2-acetyl-4,6-dimethylphenyl, 2,6-dimethyl-4-trifluoromethylphenyl, 2,6-dimethyl-4-isopropenylphenyl, 4-acetyl-2,6-dimethylphenyl, 2,4,6-triethylphenyl, 4,6-dimethyl-2-methylthiophenyl, 4,6-dimethyl-2-iodophenyl, 2-fluoromethoxy-4,6-dimethylphenyl, 4,6-dimethyl-2-isopropoxyphenyl, 4,6-dimethyl-2-ethoxyphenyl, 2,6-dichloro-4-ethoxyphenyl, 2-bromo-4,6-dimethoxyphenyl, 2-bromo-6-hydroxy-4-methoxyphenyl, 2,6-dibromo-4-ethoxyphenyl, 4-bromo-2-methoxy-6-methylphenyl, 2,6-dibromo-4-methoxyphenyl, 4,6-dibromo-2-trifluoromethoxyphenyl, 2,4-dibromo-6-trifluoromethylphenyl, 4-bromo-2-chloro-6-methylphenyl, 4-chloro-2,6-dimethoxyphenyl, 2,4-dichloro-6-methoxyphenyl, 4,6-dichloro-2-methylthiophenyl, 4,6-dichloro-2-trifluoromethylphenyl, 2,6-dimethoxy-4-ethylphenyl, 4,6-dimethyl-2-methoxyphenyl, 2,6-dimethoxy-4-methylphenyl, 2-chloro-6-methoxy-4-methylphenyl, 4,6-dimethyl-2-ethoxyphenyl, 6-hydroxy-2,4-dimethylphenyl, 4-cyano-2-methoxy-6-methylphenyl, 6-fluoro-2-methoxy-4-methylphenyl, 4-acetyl-2-methoxy-6-methylphenyl, 2-chloro-4,6-dimethoxyphenyl, 2,6-dimethoxy-4-ethoxyphenyl, 2,4,6-trimethoxyphenyl, 4,6-dibromo-2-trifluoromethoxyphenyl, 2-bromo-4-dimethylamino-6-methoxyphenyl, 4-bromo-2-methoxy-6-methylphenyl, 4,6-dimethoxy-2-propoxyphenyl, 4,6-dichloro-2-propoxyphenyl, 2-bromo-6-hydroxy-4-methoxyphenyl, 2,4,6-trifluorophenyl, 2-bromo-6-fluoro-4-methylphenyl, 4-difluoromethoxy-2,6-dimethylphenyl, 2,6-dimethyl-4-ethoxyphenyl, 2,6-dimethyl-4-isopropoxyphenyl, 2,6-dimethyl-4-methylthiophenyl, 2,6-dimethyl-4-methylsulfonylphenyl, 2,6-dimethyl-4-methylsulfinylophenyl, 2,3-dichlorophenyl, 4-methoxy-2,3-dimethylphenyl, 2-chloro-3-fluoro-4-methoxyphenyl, 2,3,4-trichlorophenyl, 4-methoxy-2,5-dimethylphenyl, 4-cyano-2,6-dimethylphenyl and 4-fluoro-2,6-dimethylphenyl.

The "pharmaceutically acceptable salts" in the present invention include, for example, salts with an inorganic acid such as sulfuric acid, hydrochloric acid, hydrobromic acid, phosphoric acid, nitric acid or the like; salts with an organic acid such as acetic acid, oxalic acid, lactic acid, tartaric acid, fumaric acid, maleic acid, citric acid, benzenesulfonic acid, methanesulfonic acid, p-toluenesulfonic acid, benzoic acid, camphorsulfonic acid, ethanesulfonic acid, glucoheptonic acid, gluconic acid, glutamic acid, glycolic acid, malic acid, malonic acid, mandelic acid, galactaric acid, naphthalene-2-sulfonic acid or the like; salts with one or more metal ions such as lithium ion, sodium ion, potassium ion, calcium ion, magnesium ion, zinc ion, aluminium ion or the like; salts with amines such as ammonia, arginine, lysine, piperazine, choline, diethylamine, 4-phenylcyclohexylamine, 2-aminoethanol, benzathine or the like.

A compound of the present invention includes any isomers such as diastereomers, enantiomers, geometric isomers and tautomeric forms. In a compound represented by a [I], if the cyclic amino group has one or more chiral carbons and/or if there is an axial chirality between Ar and pyrrolopyrimidine (or pyrrolopyridine) ring, several stereoisomers (diastereomers or enantiomers) can exist. The compound of the present invention includes all of the individual isomers and the racemic and non-racemic mixtures of the isomers.

Preferable examples of the compound of the present invention are as follows.

That is, preferable are compounds represented by the following formula [I]:

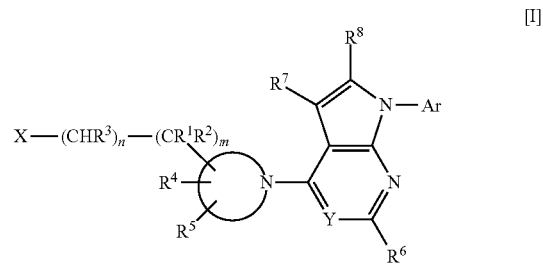

(wherein the cyclic amino group is represented by the following a [II]:

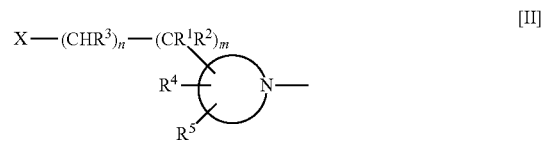

in which the cyclic amino group is a 3- to 8-membered saturated cyclic amine or a 3- to 8-membered saturated cyclic amine bridged with $C_{1-5}$alkylene or $C_{1-4}$alkylene-O—$C_{1-4}$alkylene between any different two carbon atoms of the cyclic amine, which cyclic amine is substituted with a group represented by —$(CR^1R^2)_m$—$(CHR^3)_n$—X, $R^4$ and $R^5$ independently on the same or different carbon atoms of the cyclic amine;

X is —$CO_2R^9$, —$CON(R^{10})R^{11}$, —$P(=O)(R^{12})R^{13}$ or —$S(=O)_kR^{14}$;

Y is N or $CR^{15}$;

$R^1$ is hydrogen, hydroxy, $C_{1-5}$alkyl, $C_{1-5}$alkoxy-$C_{1-5}$alkyl or hydroxy-$C_{1-5}$alkyl;

$R^2$ is hydrogen or $C_{1-5}$alkyl;

$R^3$ is hydrogen, cyano, $C_{1-5}$alkyl, $C_{1-5}$alkoxy-$C_{1-5}$alkyl or hydroxy-$C_{1-5}$alkyl;

m is an integer selected from 0, 1, 2, 3, 4 and 5;

n is 0 or 1;

with the proviso that when X is —$CO_2R^9$ or —$CON(R^{10})R^{11}$, and n is 0, then m is an integer selected from 1, 2, 3, 4 and 5;

$R^4$ is hydrogen, hydroxy, hydroxy-$C_{1-5}$alkyl, cyano, cyano-$C_{1-5}$alkyl or $C_{1-5}$alkyl;

$R^5$ is hydrogen or $C_{1-5}$alkyl;

$R^6$ is hydrogen, $C_{1-5}$alkyl, $C_{3-8}$cycloalkyl, $C_{3-8}$cycloalkyl-$C_{1-5}$alkyl, hydroxy, $C_{1-5}$alkoxy, $C_{3-8}$cycloalkyloxy or —$N(R^{16})R^{17}$;

$R^7$ and $R^8$ are the same or different, and independently are hydrogen, halogen, $C_{1-5}$alkyl, $C_{3-8}$cycloalkyl, $C_{3-8}$cycloalkyl-$C_{1-5}$alkyl, hydroxy, $C_{1-5}$alkoxy, $C_{3-8}$cycloalkyloxy, —$N(R^{18})R^{19}$, —$CO_2R^{20}$, cyano, nitro, $C_{1-5}$alkylthio, trifluoromethyl or trifluoromethoxy; or $R^7$ and $R^8$ are taken together to form —$CH_2$—$CH_2$—$CH_2$—$CH_2$— or —CH=CH—CH=CH—;

$R^9$ is hydrogen, $C_{1-10}$alkyl, $C_{3-8}$cycloalkyl or $C_{3-8}$cycloalkyl-$C_{1-5}$alkyl;

$R^{10}$ and $R^{11}$ are the same or different, and independently are hydrogen, $C_{1-5}$alkyl, $C_{3-8}$cycloalkyl or $C_{3-8}$cycloalkyl-$C_{1-5}$alkyl;

$R^{12}$ and $R^{13}$ are the same or different, and independently are —$OR^{21}$ or —$N(R^{22})R^{23}$;

$R^{14}$ is —$OR^{21}$ or —$N(R^{22})R^{23}$;

k is 1 or 2;

$R^{15}$ is hydrogen, $C_{1-5}$alkyl, halogen, cyano or —$CO_2R^{24}$;

$R^{16}$ and $R^{17}$ are the same or different, and independently are hydrogen, $C_{1-5}$alkyl, $C_{3-8}$cycloalkyl or $C_{3-8}$cycloalkyl-$C_{1-5}$alkyl;

$R^{18}$ and $R^{19}$ are the same or different, and independently are hydrogen, $C_{1-5}$alkyl, $C_{3-8}$cycloalkyl or $C_{3-8}$cycloalkyl-$C_{1-5}$alkyl;

$R^{20}$ is hydrogen or $C_{1-5}$alkyl;

$R^{21}$ is hydrogen, $C_{1-5}$alkyl, $C_{3-8}$cycloalkyl or $C_{3-8}$cycloalkyl-$C_{1-5}$alkyl;

$R^{22}$ and $R^{23}$ are the same or different, and independently are hydrogen, $C_{1-5}$alkyl, $C_{3-8}$cycloalkyl or $C_{3-8}$cycloalkyl-$C_{1-5}$alkyl;

$R^{24}$ is hydrogen or $C_{1-5}$alkyl;

Ar is aryl or heteroaryl which aryl or heteroaryl is unsubstituted or substituted with 1 or more substituents, which are the same or different, selected from the group consisting of halogen, $C_{1-5}$alkyl, $C_{3-8}$cycloalkyl, $C_{2-5}$alkenyl, $C_{2-5}$alkynyl, $C_{1-5}$alkoxy, $C_{1-5}$alkylthio, $C_{1-5}$alkylsulfinyl, $C_{1-5}$alkylsulfonyl, cyano, nitro, hydroxy, —$CO_2R^{25}$, —C(=O)$R^{26}$, —$CON(R^{27})R^{28}$, —OC(=O)$R^{29}$, —$NR^{30}CO_2R^{31}$, —S(O)$_r$N(R$^{32}$)R$^{33}$, trifluoromethyl, trifluoromethoxy, difluoromethyl, fluoromethoxy, methylenedioxy, ethylenedioxy and —$N(R^{34})R^{35}$;

$R^{25}$ is hydrogen, $C_{1-5}$alkyl, $C_{3-8}$cycloalkyl or $C_{3-8}$cycloalkyl-$C_{1-5}$alkyl;

$R^{26}$ is hydrogen or $C_{1-5}$alkyl;

$R^{27}$ and $R^{28}$ are the same or different, and independently are hydrogen, $C_{1-5}$alkyl, $C_{3-8}$cycloalkyl or $C_{3-8}$cycloalkyl-$C_{1-5}$alkyl;

$R^{29}$ is hydrogen or $C_{1-5}$alkyl;

$R^{30}$ is hydrogen or $C_{1-5}$alkyl;

$R^{31}$ is hydrogen or $C_{1-5}$alkyl;

$R^{32}$ and $R^{33}$ are the same or different, and independently are hydrogen, $C_{1-5}$alkyl, $C_{3-8}$cycloalkyl or $C_{3-8}$cycloalkyl-$C_{1-5}$alkyl;

r is 1 or 2;

$R^{34}$ and $R^{35}$ are the same or different, and independently are hydrogen, $C_{1-5}$alkyl, $C_{3-8}$cycloalkyl or $C_{3-8}$cycloalkyl-$C_{1-5}$alkyl), individual isomers thereof, racemic or non-racemic mixtures of isomers thereof or N-oxide thereof, or pharmaceutically acceptable salts and hydrates thereof.

More preferable are compounds represented by the a [I] in which Y is N. More preferable are compounds represented by the a [I] in which Y is N; m is an integer selected from 1, 2, 3, 4 and 5; n is 0; $R^1$, $R^2$, $R^4$ and $R^5$ are hydrogen. More preferable are compounds represented by the a [I] in which Y is N; the cyclic amino group is a 4- to 7-membered saturated cyclic amine; m is an integer selected from 1, 2 and 3; n is 0; $R^1$, $R^2$, $R^4$ and $R^5$ are hydrogen; $R^6$ is $C_{1-5}$alkyl; $R^7$ and $R^8$ are the same or different, and independently are hydrogen or $C_{1-5}$alkyl; Ar is phenyl which phenyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —$N(R^{34})R^{35}$ (wherein $R^{34}$ and $R^{35}$ are the same or different, and independently are hydrogen or $C_{1-3}$alkyl). More preferable are compounds represented by the a [I] in which X is —$CO_2H$, —$CONH_2$, —P(=O)(OH)$_2$ or —S(=O)$_2$OH; Y is N; the cyclic amino group is a 6-membered saturated cyclic amine; m is an integer selected from 1, 2 and 3; n is 0; $R^1$, $R^2$, $R^4$ and $R^5$ are hydrogen; $R^6$ is $C_{1-3}$alkyl; $R^7$ and $R^8$ are the same or different, and independently are hydrogen or $C_{1-3}$alkyl; Ar is phenyl which phenyl is substituted with two or three substituents, which are the same or different, selected from the group consisting of chloro, bromo, $C_{1-3}$alkyl, $C_{1-3}$alkoxy, $C_{1-3}$alkylthio, trifluoromethyl, trifluoromethoxy and dimethylamino. More preferable are compounds represented by the a [I] in which X is —$CO_2H$; Y is N; the cyclic amino group is a 6-membered saturated cyclic amine; m is an integer selected from 1, 2 and 3; n is 0; $R^1$, $R^2$, $R^4$ and $R^5$ are hydrogen; $R^6$ is methyl; $R^7$ and $R^8$ are the same or different, and independently are hydrogen or methyl; Ar is phenyl which phenyl is substituted with two or three substituents, which are the same or different, selected from the group consisting of chloro, bromo, $C_{1-3}$alkyl, $C_{1-3}$alkoxy, $C_{1-3}$alkylthio and trifluoromethyl.

Other preferable are compounds represented by the a [I] in which Y is $CR^{15}$. More preferable are compounds represented by the a [I] in which Y is $CR^{15}$; m is an integer selected from 1, 2, 3, 4 and 5; n is 0; $R^1$, $R^2$, $R^4$ and $R^5$ are hydrogen; $R^{15}$ is hydrogen or halogen. More preferable are compounds represented by the a [I] in which Y is CH; the cyclic amino group is a 4- to 7-membered saturated cyclic amine; m is an integer selected from 1, 2 and 3; n is 0; $R^1$, $R^2$, $R^4$ and $R^5$ are hydrogen; $R^6$ is $C_{1-5}$alkyl; $R^7$ and $R^8$ are the same or different, and independently are hydrogen or $C_{1-5}$alkyl; Ar is phenyl which phenyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —$N(R^{34})R^{35}$ (wherein $R^{34}$ and $R^{35}$ are the same or different, and independently are hydrogen or $C_{1-3}$alkyl. More preferable are compounds represented by the a [I] in which X is —$CO_2H$, —$CONH_2$, —P(=O)(OH)$_2$ or —S(=O)$_2$OH; Y is CH; the cyclic amino group is a 6-membered saturated cyclic amine; m is an integer selected from 1, 2 and 3; n is 0; $R^1$, $R^2$, $R^4$ and $R^5$ are hydrogen; $R^6$ is $C_{1-3}$alkyl; $R^7$ and $R^8$ are the same or different, and independently are hydrogen or $C_{1-3}$alkyl; Ar is phenyl which phenyl is substituted with two or three substituents, which are the same or different, selected from the group consisting of chloro, bromo, $C_{1-3}$alkyl, $C_{1-3}$alkoxy, $C_{1-3}$alkylthio, trifluoromethyl, trifluoromethoxy and dimethylamino. More preferable are compounds represented by the a [I] in which X is —$CO_2H$; Y is CH; the cyclic amino group is a 6-membered saturated cyclic amine; m is an integer selected from 1, 2 and 3; n is 0; $R^1$, $R^2$, $R^4$ and $R^5$ are hydrogen; $R^6$ is methyl; $R^7$ and $R^8$ are the same or different, and independently are hydrogen or methyl; Ar is phenyl which phenyl is substituted with two or three substituents, which are the same or different, selected from the group consisting of chloro, bromo, $C_{1-3}$alkyl, $C_{1-3}$alkoxy, $C_{1-3}$alkylthio and trifluoromethyl.

The preferable cyclic amino group is 6-membered saturated amine.

The preferable X is $CO_2H$, $CONH_2$, $P(O)(OH)_2$ or $S(O)_2OH$. The more preferable X is $CO_2H$.

The preferable Y is N or CH.

The preferable $R^1$ is hydrogen.

The preferable $R^2$ is hydrogen.

The preferable $R^3$ is hydrogen.

The preferable $R^4$ is hydrogen.

The preferable $R^5$ is hydrogen.

The preferable $R^6$ is $C_{1-3}$ alkyl. The more preferable $R^6$ is methyl.

The preferable $R^7$ is $C_{1-3}$ alkyl. The more preferable $R^7$ is methyl.

The preferable $R^8$ is hydrogen or $C_{1-3}$ alkyl. The more preferable $R^8$ is hydrogen or methyl.

The preferable Ar is phenyl which phenyl is substituted with two or three substituents, which are the same or different, selected from the group consisting of chloro, bromo, $C_{1-3}$alkyl, $C_{1-3}$alkoxy, $C_{1-3}$alkylthio, trifluoromethyl, trifluoromethoxy and dimethylamino. The more preferable Ar is phenyl which phenyl is substituted with two or three substituents, which are the same or different, selected from the group consisting of chloro, bromo and $C_{1-3}$alkyl.

Especially preferable compounds of the present invention are:

{1-[7-(4-bromo-2,6-dimethyl-phenyl)-2,5,6-trimethyl-7H-pyrrolo[2,3-d]pyrimidin-4-yl]-piperidin-4-yl}-acetic acid

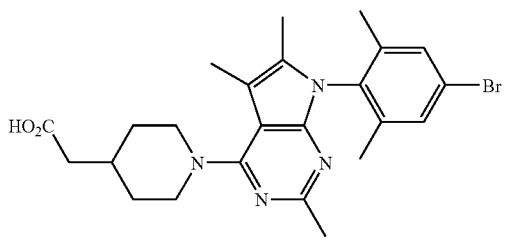

{1-[7-(4-bromo-2,6-dimethyl-phenyl)-2,5-dimethyl-7H-pyrrolo[2,3-d]pyrimidin-4-yl]-piperidin-4-yl}-acetic acid

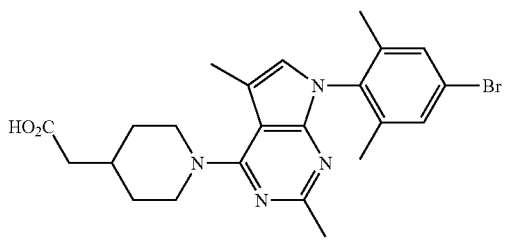

{1-[1-(4-bromo-2,6-dimethyl-phenyl)-2,3,6-trimethyl-1H-pyrrolo[2,3-b]pyridin-4-yl]-piperidin-4-yl}-acetic acid

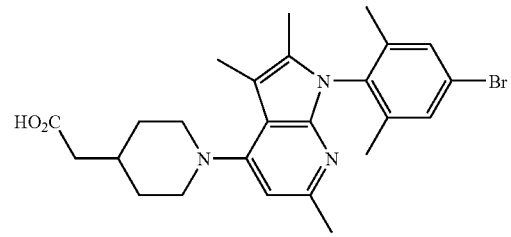

{1-[1-(4-bromo-2,6-dimethyl-phenyl)-3,6-dimethyl-1H-pyrrolo[2,3-b]pyridin-4-yl]-piperidin-4-yl}-acetic acid

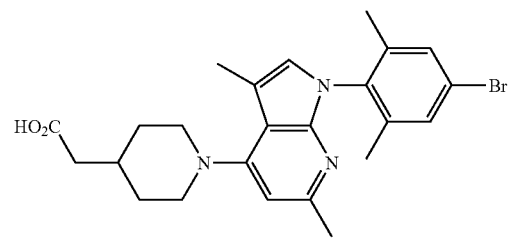

{1-[1-(4-chloro-2,6-dimethyl-phenyl)-2,3,6-trimethyl-1H-pyrrolo[2,3-b]pyridin-4-yl]-piperidin-4-yl}-acetic acid

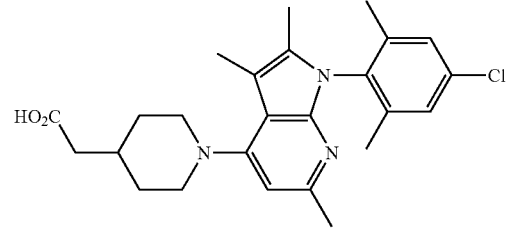

{1-[1-(4-chloro-2,6-dimethyl-phenyl)-3,6-dimethyl-1H-pyrrolo[2,3-b]pyridin-4-yl]-piperidin-4-yl}-acetic acid

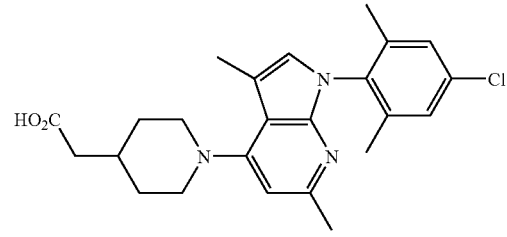

{1-[1-(2,6-dibromo-4-isopropyl-phenyl)-2,3,6-trimethyl-1H-pyrrolo[2,3-b]pyridin-4-yl]-piperidin-4-yl}-acetic acid

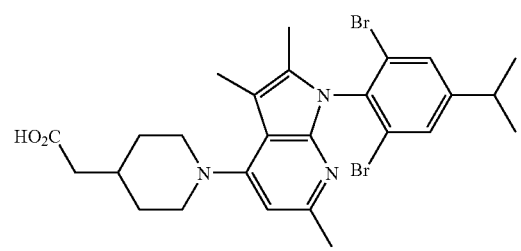

{1-[1-(2,6-dibromo-4-isopropyl-phenyl)-3,6-dimethyl-1H-pyrrolo[2,3-b]pyridin-4-yl]-piperidin-4-yl}-acetic acid

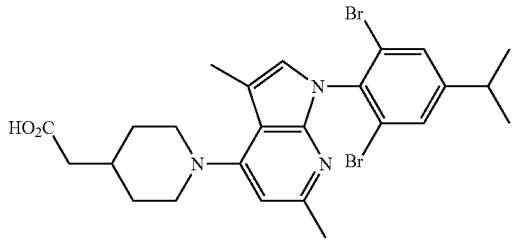

{1-[3,6-dimethyl-1-(2,4,6-tribromo-phenyl)-1H-pyrrolo[2,3-b]pyridin-4-yl]-piperidin-4-yl}-acetic acid

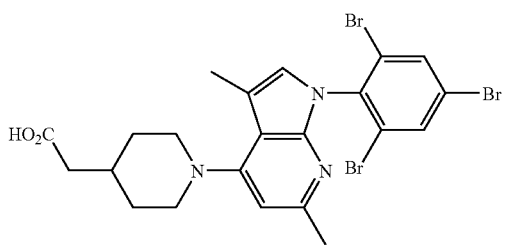

{1-[1-(4-bromo-2,6-dichloro-phenyl)-3,6-dimethyl-1H-pyrrolo[2,3-b]pyridin-4-yl]-piperidin-4-yl}-acetic acid

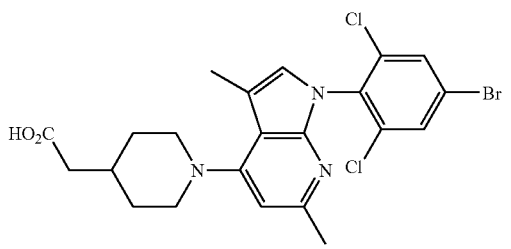

{1-[3,6-dimethyl-1-(2,4,6-trichloro-phenyl)-1H-pyrrolo[2,3-b]pyridin-4-yl]-piperidin-4-yl}-acetic acid

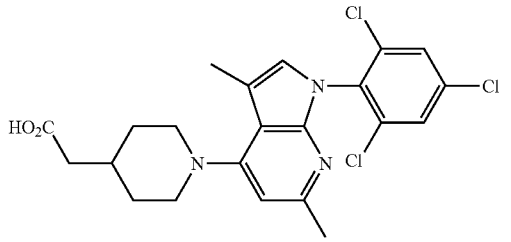

{1-[1-(2,6-dibromo-4-chloro-phenyl)-3,6-dimethyl-1H-pyrrolo[2,3-b]pyridin-4-yl]-piperidin-4-yl}-acetic acid

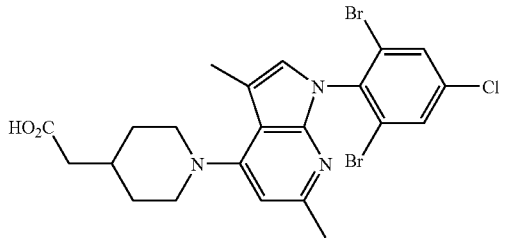

{1-[1-(2-bromo-4-isopropyl-phenyl)-3,6-dimethyl-1H-pyrrolo[2,3-b]pyridin-4-yl]-piperidin-4-yl}-acetic acid

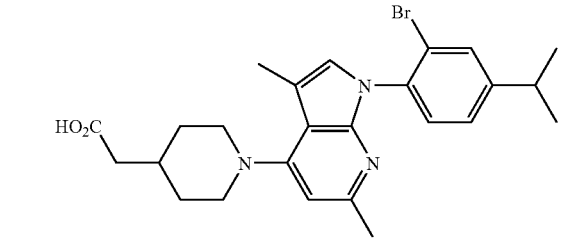

{1-[1-(4-isopropyl-2-methylsulfanyl-phenyl)-3,6-dimethyl-1H-pyrrolo[2,3-b]pyridin-4-yl]-piperidin-4-yl}-acetic acid

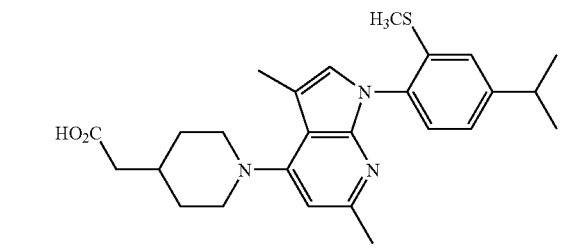

{1-[1-(2,4-dibromo-phenyl)-3,6-dimethyl-1H-pyrrolo[2,3-b]pyridin-4-yl]-piperidin-4-yl}-acetic acid

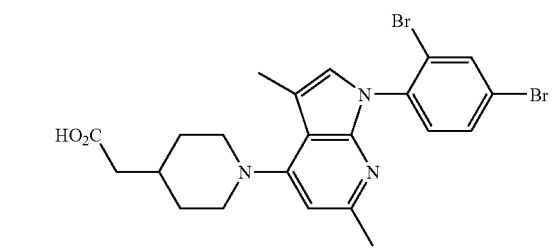

3-{1-[7-(4-bromo-2,6-dimethyl-phenyl)-2,5,6-trimethyl-7H-pyrrolo[2,3-d]pyrimidin-4-yl]-piperidin-4-yl}-propionic acid

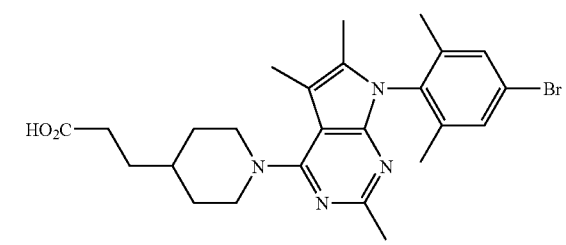

3-{1-[7-(4-bromo-2,6-dimethyl-phenyl)-2,5-dimethyl-7H-pyrrolo[2,3-d]pyrimidin-4-yl]-piperidin-4-yl}-propionic acid

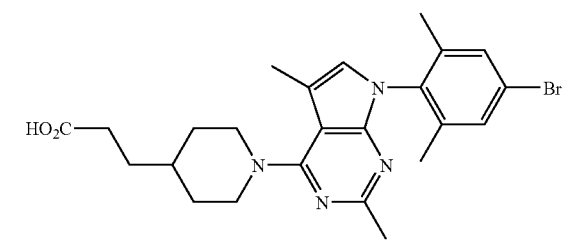

3-{1-[1-(4-bromo-2,6-dimethyl-phenyl)-2,3,6-trimethyl-1H-pyrrolo[2,3-b]pyridin-4-yl]-piperidin-4-yl}-propionic acid

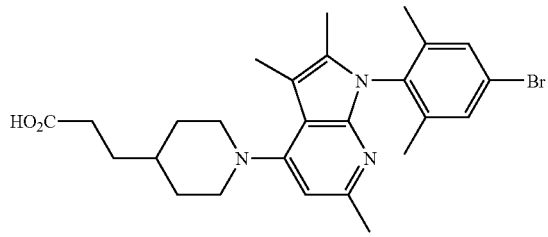

3-{1-[1-(4-bromo-2,6-dimethyl-phenyl)-3,6-dimethyl-1H-pyrrolo[2,3-b]pyridin-4-yl]-piperidin-4-yl}-propionic acid

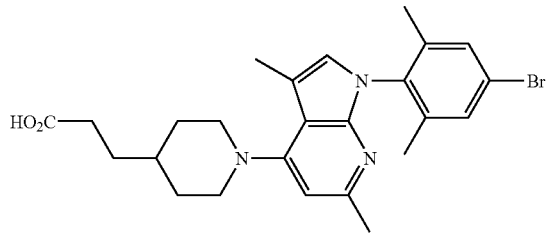

3-{1-[1-(4-chloro-2,6-dimethyl-phenyl)-2,3,6-trimethyl-1H-pyrrolo[2,3-b]pyridin-4-yl]-piperidin-4-yl}-propionic acid

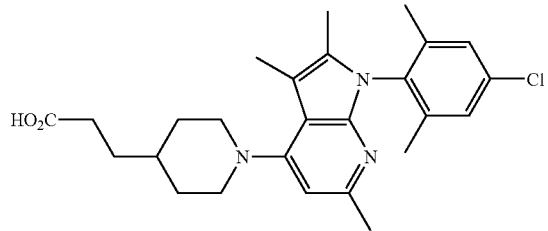

3-{1-[1-(4-chloro-2,6-dimethyl-phenyl)-3,6-dimethyl-1H-pyrrolo[2,3-b]pyridin-4-yl]-piperidin-4-yl}-propionic acid

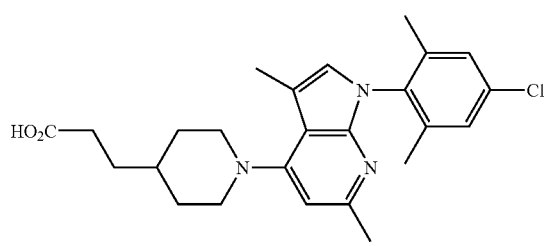

3-{1-[1-(2,6-dibromo-4-isopropyl-phenyl)-2,3,6-trimethyl-1H-pyrrolo[2,3-b]pyridin-4-yl]-piperidin-4-yl}-propionic acid

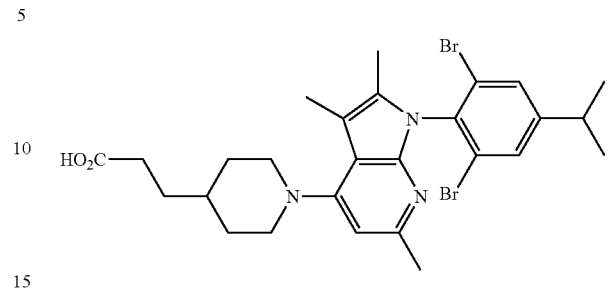

3-{1-[1-(2,6-dibromo-4-isopropyl-phenyl)-3,6-dimethyl-1H-pyrrolo[2,3-b]pyridin-4-yl]-piperidin-4-yl}-propionic acid

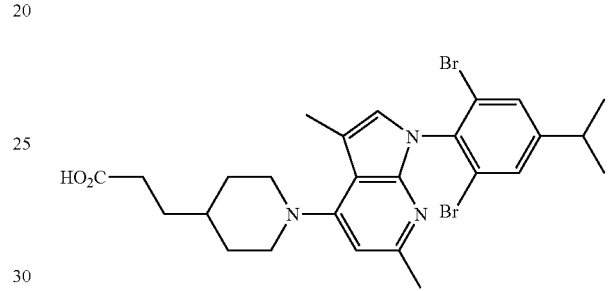

3-{1-[1-(4-bromo-2,6-dichloro-phenyl)-3,6-dimethyl-1H-pyrrolo[2,3-b]pyridin-4-yl]-piperidin-4-yl}-propionic acid

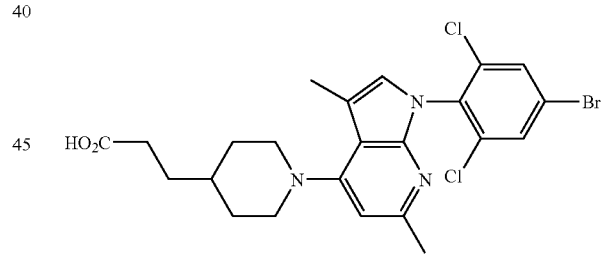

3-{1-[3,6-dimethyl-1-(2,4,6-trichloro-phenyl)-1H-pyrrolo[2,3-b]pyridin-4-yl]piperidin-4-yl}-propionic acid

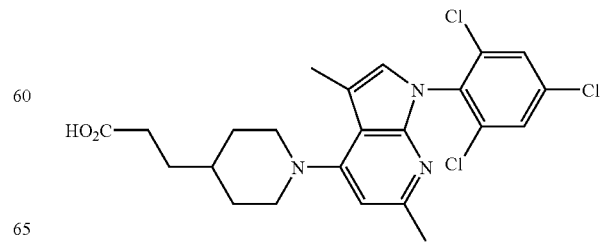

3-{1-[1-(2,6-dibromo-4-chloro-phenyl)-3,6-dimethyl-1H-pyrrolo[2,3-b]pyridin-4-yl]-piperidin-4-yl}-propionic acid

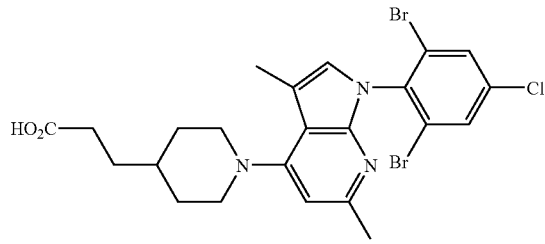

3-{1-[1'-(4-methoxy-2,6-dimethyl-phenyl)-3,6-dimethyl-1H-pyrrolo[2,3-b]pyridin-4-yl]-piperidin-4-yl}-propionic acid

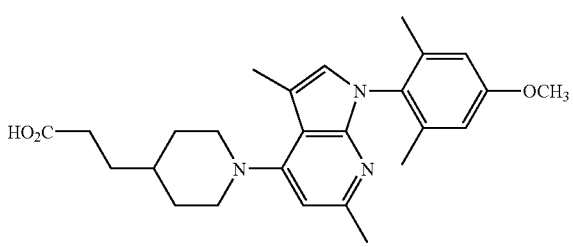

3-{1-[1-(2-bromo-4-isopropyl-phenyl)-3,6-dimethyl-1H-pyrrolo[2,3-b]pyridin-4-yl]-piperidin-4-yl}-propionic acid

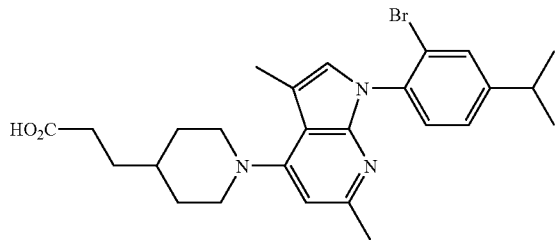

3-{1-[1-(4-isopropyl-2-methylsulfanyl-phenyl)-3,6-dimethyl-1H-pyrrolo[2,3-b]pyridin-4-yl]-piperidin-4-yl}-propionic acid

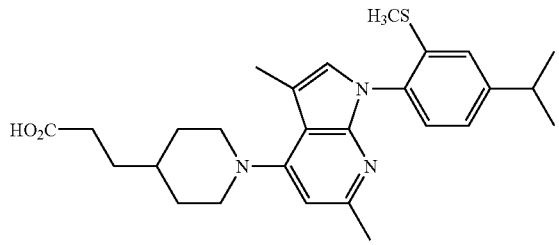

3-{1-[1-(2,4-dibromo-phenyl)-3,6-dimethyl-1H-pyrrolo[2,3-b]pyridin-4-yl]-piperidin-4-yl}-propionic acid

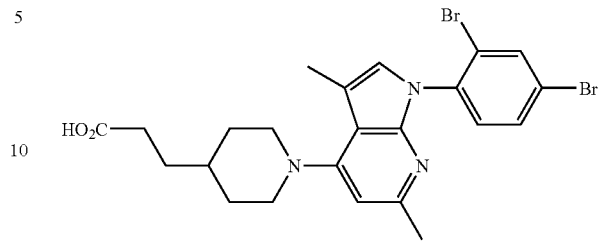

4-{1-[1-(4-bromo-2,6-dimethyl-phenyl)-2,3,6-trimethyl-1H-pyrrolo[2,3-b]pyridin-4-yl]-piperidin-4-yl}-butyric acid

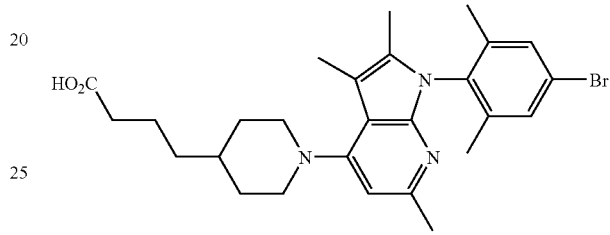

4-{1-[1-(4-bromo-2,6-dimethyl-phenyl)-3,6-dimethyl-1H-pyrrolo[2,3-b]pyridin-4-yl]-piperidin-4-yl}-butyric acid

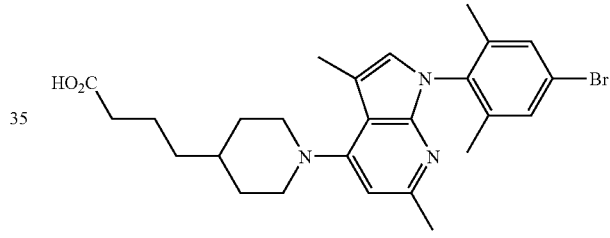

{8-[1-(4-bromo-2,6-dimethyl-phenyl)-3,6-dimethyl-1H-pyrrolo[2,3-b]pyridin-4-yl]-8-aza-bicyclo[3.2.1]oct-3-yl}-acetic acid

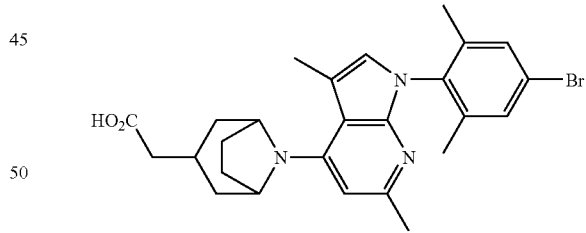

{1-[1-(4-bromo-2,6-dimethyl-phenyl)-3,6-dimethyl-1H-pyrrolo[2,3-b]pyridin-4-yl]-piperidin-3-yl}-acetic acid

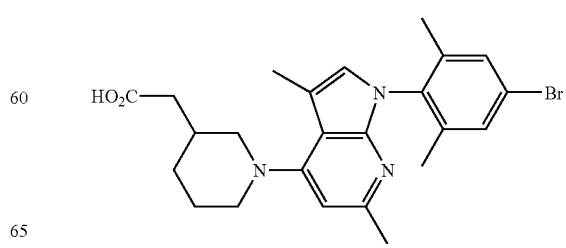

2-{1-[1-(4-bromo-2,6-dimethyl-phenyl)-3,6-dimethyl-1H-pyrrolo[2,3-b]pyridin-4-yl]-piperidin-4-yl}-acetamide

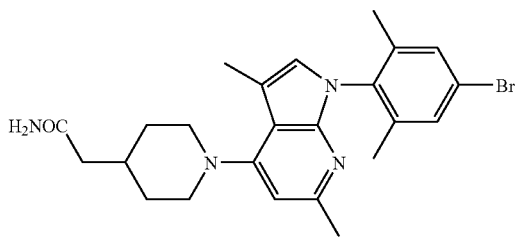

3-{1-[1-(4-bromo-2,6-dimethyl-phenyl)-3,6-dimethyl-1H-pyrrolo[2,3-b]pyridin-4-yl]-piperidin-4-yl}-propionamide

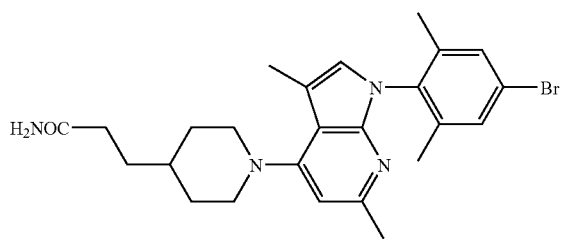

{1-[1-(4-bromo-2,6-dimethyl-phenyl)-3,6-dimethyl-1H-pyrrolo[2,3-b]pyridin-4-yl]-piperidin-4-ylmethyl}-phosphonic acid

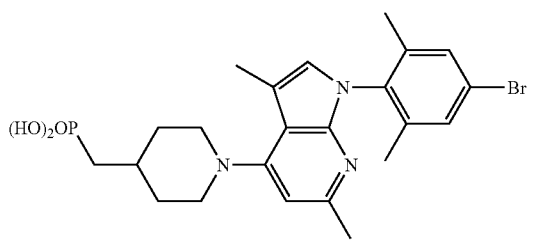

{1-[1-(4-bromo-2,6-dimethyl-phenyl)-3,6-dimethyl-1H-pyrrolo[2,3-b]pyridin-4-yl]-piperidin-4-yl}-methanesulfonic acid

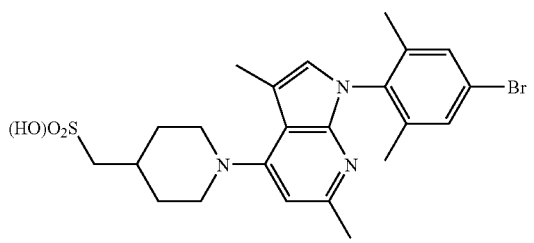

2-{1-[1-(4-bromo-2,6-dimethyl-phenyl)-3,6-dimethyl-1H-pyrrolo[2,3-b]pyridin-4-yl]-piperidin-4-yl}-ethanesulfonic acid

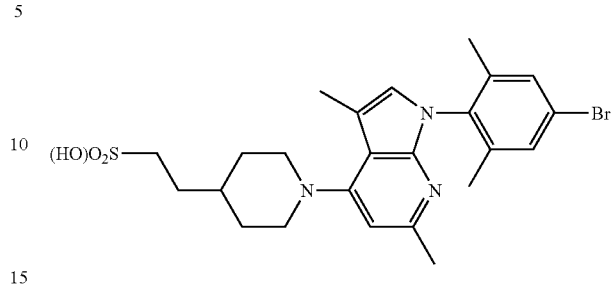

2-{1-[1-(4-bromo-2,6-dimethyl-phenyl)-3,6-dimethyl-1H-pyrrolo[2,3-b]pyridin-4-yl]-piperidin-4-yl}-ethanesulfonic acid amide

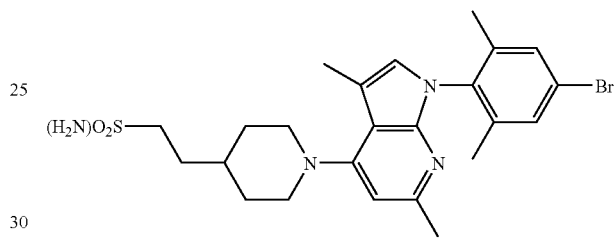

{1-[7-(4-isopropyl-2-methylsulfanyl-phenyl)-2,5-dimethyl-7H-pyrrolo[2,3-d]pyrimidin-4-yl]-piperidin-4-yl}-acetic acid

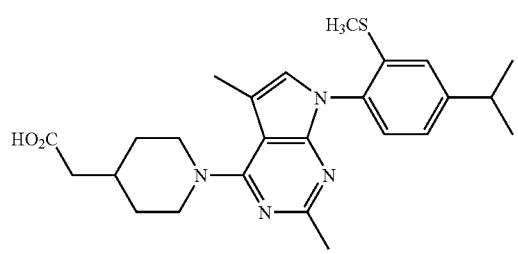

4-{1-[7-(4-bromo-2,6-dimethyl-phenyl)-2,5,6-trimethyl-7H-pyrrolo[2,3-d]pyrimidin-4-yl]-piperidin-4-yl}-butyric acid

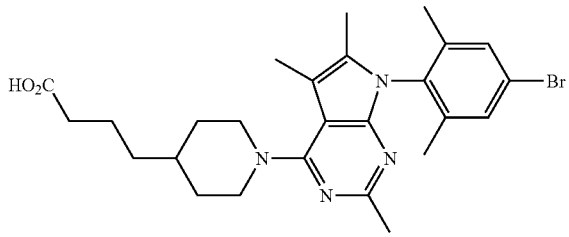

2-{1-[7-(4-bromo-2,6-dimethyl-phenyl)-2,5,6-trimethyl-7H-pyrrolo[2,3-d]pyrimidin-4-yl]-3,3-dimethyl-piperidin-4-yl}-acetamide

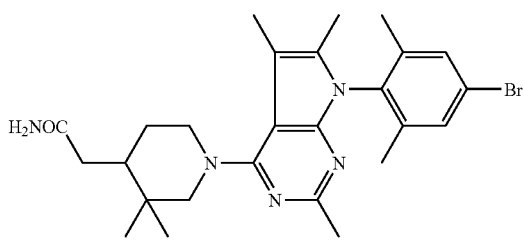

2,2-dimethyl-propionic acid 2-{1-[1-(4-bromo-2,6-dimethyl-phenyl)-3,6-dimethyl-1H-pyrrolo[2,3-b]pyridin-4-yl]-piperidin-4-yl}-acetoxymethyl ester

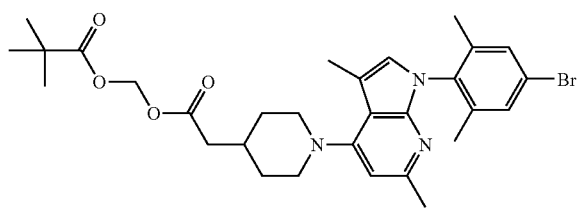

and (S)-2-(2-{1-[1-(4-bromo-2,6-dimethyl-phenyl)-3,6-dimethyl-1H-pyrrolo[2,3-b]pyridin-4-yl]-piperidin-4-yl}-acetylamino)-3-phenyl-propionic acid ethyl ester.

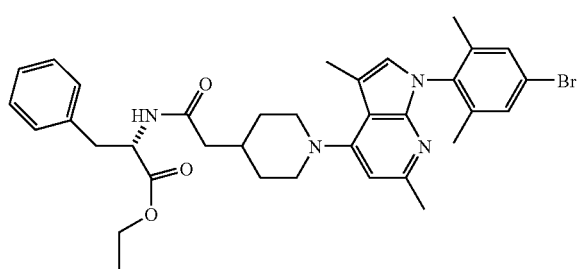

The compound represented by the a [I] can be produced, for example, by the process shown in the following reaction schemes 1-4 [in the following reaction scheme, $R^1$, $R^2$, $R^3$, $R^5$, $R^6$, $R^7$, $R^8$, m, n, Y and Ar are as defined above; $L^1$, $L^2$ and $L^3$ are the same or different, and independently chloro, bromo, iodo, methanesulfonyloxy, benzenesulfonyloxy, p-toluenesulfonyloxy or trifluoromethanesulfonyloxy group; $X^a$ is —CN, —$CO_2(C_{1-5}$alkyl), —$CON(R^{10})R^{11}$ or —$S(O)_2N(R^{22})R^{23}$; $X^b$ is $OR^9$ or $N(R^{10})R^{11}$; $R^a$ is $C_{1-5}$alkyl; d is an integer selected from 1, 2, 3, 4, 5 and 6; e and f are the same or different, independently, integers selected from 1, 2 and 3].

Reaction Scheme 1

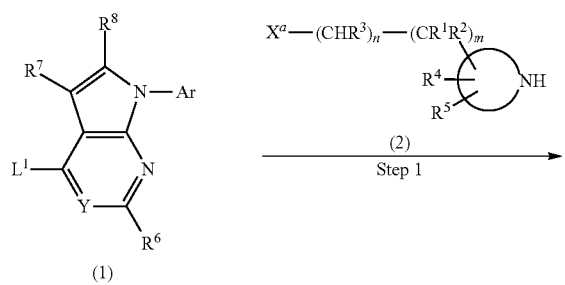

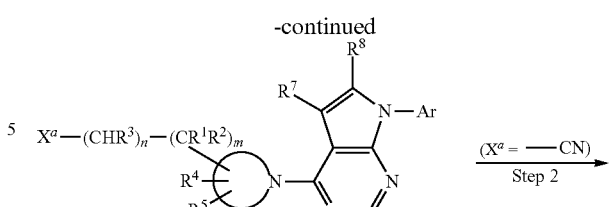

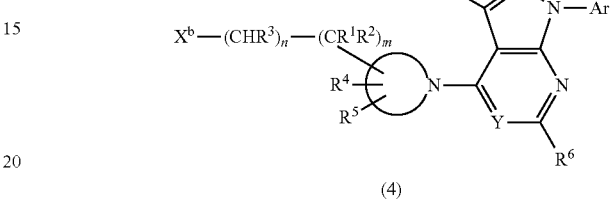

Step 1:

Compound (3), a compound of the present invention, can be obtained by reacting Compound (1) with Compound (2) in an inert solvent or without any solvent in the presence or absence of a base. Herein, the base includes, for example, amines such as triethylamine, N,N-diisopropylethylamine, pyridine and the like; inorganic bases such as sodium carbonate, potassium carbonate, sodium hydrogencarbonate, potassium hydrogencarbonate, sodium hydroxide, potassium hydroxide, barium hydroxide, sodium hydride and the like; metal alcoholates such as sodium methoxide, sodium ethoxide, potassium tert-butoxide and the like; metal amides such as sodium amide, lithium diisopropylamide and the like; and Grignard reagents such as methylmagnesium bromide and the like. The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; hydrocarbons such as benzene, toluene, xylene and the like; esters such as ethyl acetate, ethyl formate and the like; amides such as N,N-dimethylformamide, N-methylpyrrolidone, N,N-dimethylacetamide and the like; acetonitrile; dimethyl sulfoxide; pyridine; chloroform; dichloromethane; water; and mixtures of solvents selected from these inert solvents.

Step 2:

When $X^a$ is a cyano group, the cyano group can be converted to the carboxy group, a $C_{1-5}$alkoxycarbonyl group or the carbamoyl group by using an acid or a base in an inert solvent or without any solvent. Herein, the acid includes, for example, organic acids such as formic acid, acetic acid, trifluoroacetic acid, benzenesulfonic acid, methanesulfonic acid, p-toluenesulfonic acid, benzoic acid, trifluoromethanesulfonic acid and the like; inorganic acids such as sulfuric acid, hydrochloric acid, hydrobromic acid, phosphoric acid, polyphosphoric acid, nitric acid or the like. The base includes, for example, inorganic bases such as sodium carbonate, potassium carbonate, sodium hydrogencarbonate, potassium hydrogencarbonate, sodium hydroxide, potassium hydroxide, lithium hydroxide, barium hydroxide and the like; metal alcoholates such as sodium methoxide, sodium ethoxide, potassium tert-butoxide and the like. The inert solvent includes, for example, alcohols such as methanol, ethanol, isopropyl alcohol, ethylene glycol, tert-butanol and the like; ethers such as diethyl ether, tetrahydrofuran, 1,4-dioxane, 1,2-dimethoxyethane and the like; hydrocarbons such as benzene, toluene, xylene and the like; esters such as ethyl acetate, ethyl formate and the like; amides such as N,N-dimethylformamide, N-methylpyrrolidone, N,N-dimethylacetamide and the like; acetonitrile; dimethyl sulfoxide; pyridine; chloroform; dichloromethane; water; and mixtures of solvents selected from these inert solvents.

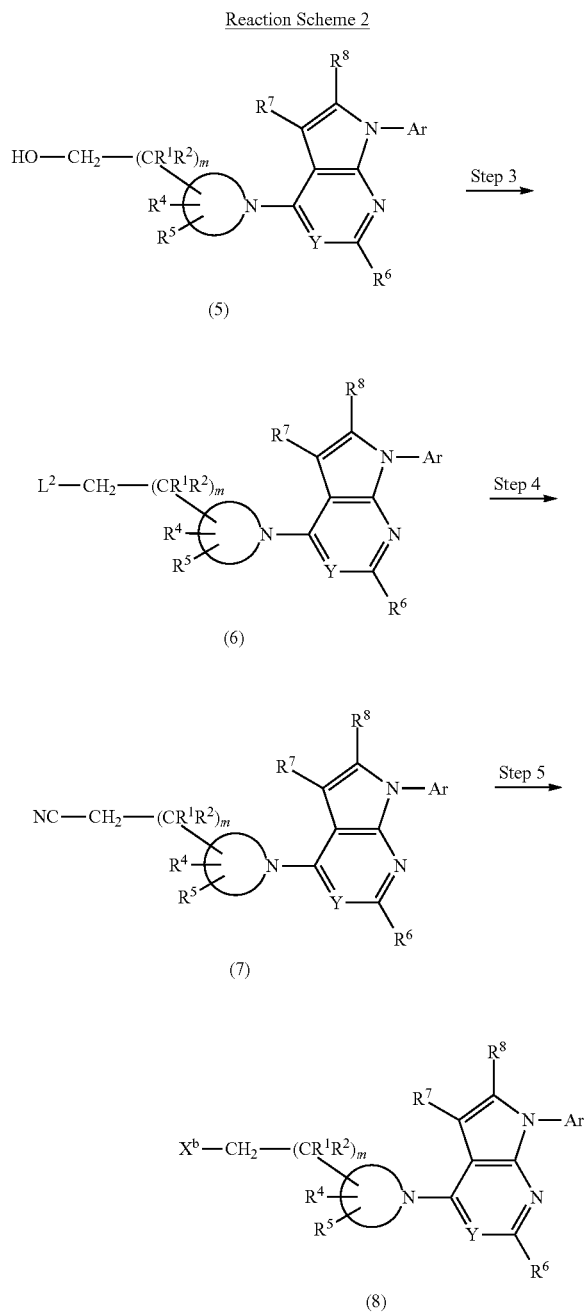

Step 3:

The hydroxy group in Compound (5), which can be prepared in the similar method as described in step 1, can be converted to $L^2$ by using a halogenating agent or a sulfonating agent in the presence or absence of a base in an inert solvent or without any solvent. Herein, the halogenating reagent includes, for example, phosphoryl chloride, phosphoryl bromide, phosphorous pentachloride, phosphorous trichloride, phosphorous pentabromide, phosphorous tribromide, thionyl chloride, thionyl bromide, oxalyl chloride, oxalyl bromide, $PPh_3$-$CCl_4$, $PPh_3$-$CBr_4$ and the like. The sulfonating reagent includes, for example, p-toluenesulfonyl chloride, methanesulfonyl chloride, p-toluenesulfonic anhydride, methansulfonic anhydride, trifluoromethanesulfonic anhydride, N-phenylbis(trifluoromethanesulfonimide) and the like. The base includes, for example, amines such as triethylamine, N,N-diisopropylethylamine, pyridine, N,N-dimethylaniline, N,N-diethylaniline and the like; inorganic bases such as sodium carbonate, potassium carbonate, sodium hydrogencarbonate, potassium hydrogencarbonate, sodium hydroxide, potassium hydroxide, barium hydroxide, sodium hydride and the like; metal alcoholates such as sodium methoxide, sodium ethoxide, potassium tert-butoxide and the like; metal amides such as sodium amide, lithium diisopropylamide and the like; and Grignard reagents such as methyl magnesium bromide and the like. The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; hydrocarbons such as benzene, toluene, xylene and the like; esters such as ethyl acetate, ethyl formate and the like; amides such as N,N-dimethylformamide, N-methylpyrrolidone, N,N-dimethylacetamide and the like; acetonitrile; dimethyl sulfoxide; pyridine; chloroform; dichloromethane; water; and mixtures of solvents selected from these inert solvents.

When $L^2$ is not an iodide atom, $L^2$ can be converted to an iodine atom before performing the next step by using sodium iodide or potassium iodide in an inert solvent.

Step 4:

$L^2$ in Compound (6) can be converted to the cyano group by reacting compound (6) with a cyanide in the presence or absence of a phase transfer catalyst or a Crown ether in an inert solvent. Herein, the cyanide includes, for example, potassium cyanide, sodium cyanide and the like. The phase transfer catalyst includes, for example, tetrabutylammonium chloride, tetrabutylammonium bromide, tetrabutylammonium iodide, tetrabutylammonium hydrogensulfate, tetraethylammonium chloride, tetraethylammonium bromide, tetraethylammonium iodide, benzyltributylammonium chloride, benzyltributylammonium bromide, benzyltributylammonium iodide, benzyltriethylammonium chloride, benzyltriethylammonium bromide, benzyltriethylammonium iodide and the like. The Crown ether includes, for example, 15-Crown-5, 18-Crown-6 and the like. The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; hydrocarbons such as benzene, toluene, xylene and the like; esters such as ethyl acetate, ethyl formate and the like; amides such as N,N-dimethylformamide, N-methylpyrrolidone, N,N-dimethylacetamide and the like; acetonitrile; dimethyl sulfoxide; pyridine; chloroform; dichloromethane; water; and mixtures of solvents selected from these inert solvents.

Step 5:

The cyano group in Compound (7) can be converted to a carboxy group or a carbamoyl group in the same method as described in step 2.

Reaction Scheme 3

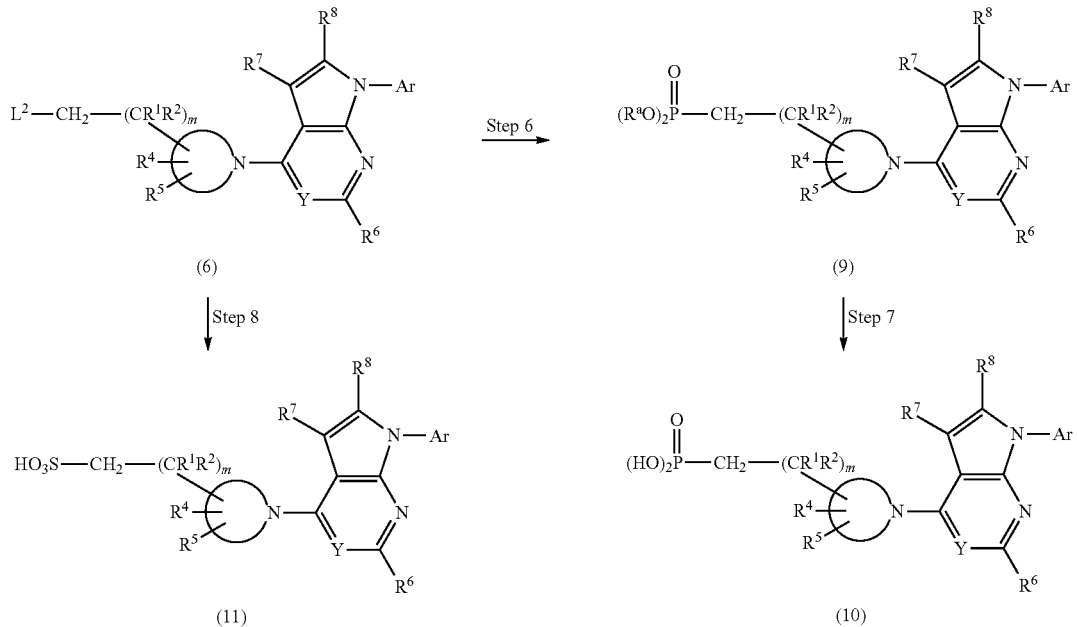

Step 6:

Compound (6) can be converted to Compound (9) by reacting Compound (6) with the trialkyl phosphite. Herein, the trialkyl phosphite includes, for example, trimethyl phosphite, triethyl phosphite, triisopropyl phosphite and the like.

Step 7:

The phosphate ester group in Compound (9) can be hydrolyzed by using an acid or a base in an inert solvent. Herein, the acid includes, for example, organic acids such as formic acid, acetic acid, trifluoroacetic acid, benzenesulfonic acid, methanesulfonic acid, p-toluenesulfonic acid, benzoic acid, trifluoromethanesulfonic acid and the like; inorganic acids such as sulfuric acid, hydrochloric acid, hydrobromic acid, phosphoric acid, polyphosphoric acid, nitric acid or the like. The base includes, for example, sodium carbonate, potassium carbonate, sodium hydrogencarbonate, potassium hydrogencarbonate, sodium hydroxide, potassium hydroxide, barium hydroxide, sodium hydride, potassium hydride and the like; metal alcoholates such as sodium methoxide, sodium ethoxide, potassium tert-butoxide and the like. The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; hydrocarbons such as benzene, toluene, xylene and the like; esters such as ethyl acetate, ethyl formate and the like; amides such as N,N-dimethylformamide, N-methylpyrrolidone, N,N-dimethylacetamide and the like; acetonitrile; dimethyl sulfoxide; pyridine; water; and mixtures of solvents selected from these inert solvents.

Step 8:

Compound (11) can be obtained by reacting Compound (6) with a sulfite in the presence or absence of a phase transfer catalyst or a Crown ether in an inert solvent. Herein, the sulfite includes, for example, sodium sulfite, potassium sulfite and the like. The phase transfer catalyst includes, for example, tetrabutylammonium chloride, tetrabutylammonium bromide, tetrabutylammonium iodide, tetrabutylammonium hydrogensulfate, tetraethylammonium chloride, tetraethylammonium bromide, tetraethylammonium iodide, benzyltributylammonium chloride, benzyltributylammonium bromide, benzyltributylammonium iodide, benzyltriethylammonium chloride, benzyltriethylammonium bromide, benzyltriethylammonium iodide and the like. The Crown ether includes, for example, 15-Crown-5, 18-Crown-6 and the like. The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; hydrocarbons such as benzene, toluene, xylene and the like; esters such as ethyl acetate, ethyl formate and the like; amides such as N,N-dimethylformamide, N-methylpyrrolidone, N,N-dimethylacetamide and the like; acetonitrile; dimethyl sulfoxide; pyridine; water; and mixtures of solvents selected from these inert solvents.

Reaction Scheme 4

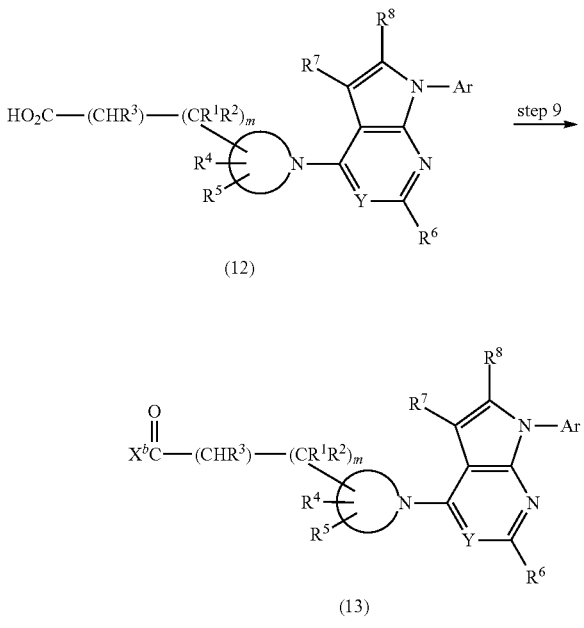

Step 9:

When $X^b$ is not hydroxy, Compound (13), a compound of the present invention, can be synthesized from Compound (12) by conventional methods for amidating a carboxyl group, esterification of a carboxyl group or alkylation of a carboxy group in the presence or absence of a base in an inert solvent. Conventional methods for amidating a carboxyl group or esterification of a carboxyl group are: for example, the reaction via a mixed acid anhydride obtained by the reaction of Compound (12) with haloformic acid ester (e.g., ethyl chloroformate or isobutyl chloroformate) or an acid chloride (e.g., benzoyl chloride or pivaloyl chloride); the reaction in the presence of a condensing agent such as N,N'-dicyclohexylcarbodiimide (DCC), 1-(3-dimethylaminopropyl)-3-ethylcarbodiimide hydrochloride (EDCl), carbonyldiimidazole (CDI), diphenylphosphorylazide (DPPA), diethyl cyanophosphate or the like, and optionally an additive such as 1-hydroxybenzotriazole (HOBt), N-hydroxysuccinimide, 4-dimethylaminopyridine or the like; or the reaction via an acid halide obtained by the reaction of Compound (12) with a halogenating reagent such as thionyl chloride, oxalyl chloride, or the like; conventional methods for alkylation of a carboxy group is the reaction with an alkylating reagent such as alkylhalide or alkylsulfonate in the presence or absence of an additive to accelerate the reaction such as NaI and KI. When $R^9$ contains an alkoxycarbonyl group, the alkoxycarbonyl group can be converted to the carboxy group by using a method as described in Protective Group in Organic Synthesis (T. W. Greene, P. G. M. Wuts; $3^{rd}$ ed., 1999, John Wiley & sons, Inc.). The base includes amines such as triethylamine, N,N-diisopropylethylamine, pyridine, 1,8-diazabicyclo[5.4.0]undec-7-ene and the like; inorganic bases such as sodium carbonate, potassium carbonate, sodium hydrogencarbonate, potassium hydrogencarbonate, sodium hydroxide, potassium hydroxide, lithium hydroxide, barium hydroxide, sodium hydride and the like; metal alcoholates such as sodium methoxide, sodium ethoxide, potassium tert-butoxide and the like. The acid includes, for example, organic acids such as formic acid, acetic acid, trifluoroacetic acid, benzenesulfonic acid, methanesulfonic acid, p-toluenesulfonic acid, benzoic acid, trifluoromethanesulfonic acid and the like; inorganic acids such as sulfuric acid, hydrochloric acid, hydrobromic acid, phosphoric acid, polyphosphoric acid, nitric acid or the like. The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; hydrocarbons such as benzene, toluene and the like; amides such as N,N-dimethylformamide, N-methylpyrrolidone, N,N-dimethylacetamide and the like; acetonitrile; dimethyl sulfoxide; pyridine; chloroform; dichloromethane; water; and mixtures of solvents selected from these inert solvents.

Reaction Scheme 5

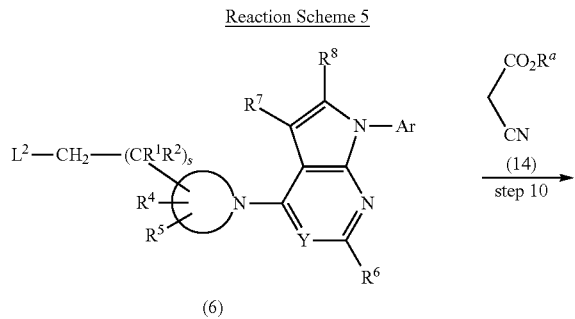

(6)

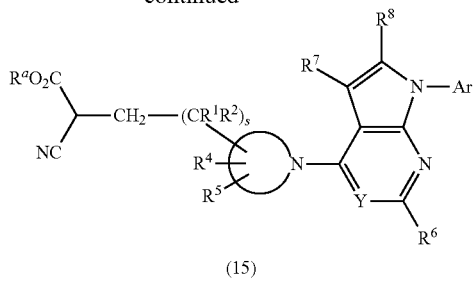

(15)

Step 10:

Compound (15), a compound of the present invention, can be obtained by reacting Compound (6) with Compound (14) in the presence or absence of a base in an inert solvent. The base includes amines such as triethylamine, N,N-diisopropylethylamine, pyridine, 1,8-diazabicyclo[5.4.0]undec-7-ene and the like; inorganic bases such as sodium carbonate, potassium carbonate, sodium hydrogencarbonate, potassium hydrogencarbonate, sodium hydride and the like; metal alcoholates such as sodium methoxide, sodium ethoxide, potassium tert-butoxide and the like. The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; hydrocarbons such as benzene, toluene and the like; amides such as N,N-dimethylformamide, N-methylpyrrolidone, N,N-dimethylacetamide and the like; acetonitrile; dimethyl sulfoxide; pyridine; chloroform; dichloromethane; water; and mixtures of solvents selected from these inert solvents.

Reaction Scheme 6

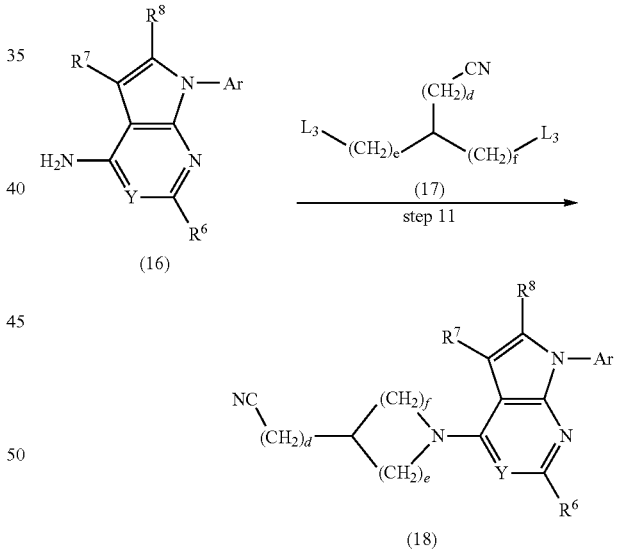

Step 11:

Compound (18) can be obtained by reacting Compound (16) with Compound (17) in the presence or absence of a base in an inert solvent or without any solvent. The base includes amines such as triethylamine, N,N-diisopropylethylamine, or pyridine and the like; inorganic bases such as sodium carbonate, potassium carbonate, sodium hydrogencarbonate, potassium hydrogencarbonate, sodium hydroxide, potassium hydroxide, barium hydroxide, sodium hydride and the like; metal alcoholates such as sodium methoxide, sodium ethoxide, potassium tert-butoxide and the like. The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; hydrocarbons such as benzene, toluene and the like; amides such as N,N-dimethylformamide, N-methylpyrrolidone, N,N-dimethylacetamide and the like; acetonitrile; dimethyl sulfoxide; pyridine; chloroform; dichloromethane; water; and mixtures of solvents selected from these inert solvents.

The compound of the present invention can be converted to a salt in an inert solvent with an inorganic acid such as sulfuric acid, hydrochloric acid, hydrobromic acid, phosphoric acid, nitric acid or the like, with an organic acid such as acetic acid, oxalic acid, lactic acid, tartaric acid, fumaric acid, maleic acid, citric acid, benzenesulfonic acid, methanesulfonic acid, p-toluenesulfonic acid, benzoic acid, camphorsulfonic acid, ethanesulfonic acid, glucoheptonic acid, gluconic acid, glutamic acid, glycolic acid, malic acid, malonic acid, mandelic acid, galactaric acid, naphthalene-2-sulfonic acid or the like, with an inorganic base such as lithium hydroxide, sodium hydroxide, potassium hydroxide, calcium hydroxide, magnesium hydroxide, zinc hydroxide, aluminum hydroxide or the like or with an organic base such as ammonia, arginine, lysine, piperazine, choline, diethylamine, 4-phenylcyclohexylamine, 2-aminoethanol, benzathine or the like. The inert solvent includes, for example, alcohols such as methanol, ethanol, isopropyl alcohol, ethylene glycol and the like; ethers such as diethyl ether, diisopropyl ether, tetrahydrofuran, 1,4-dioxane, 1,2-dimethoxyethane and the like; hydrocarbons such as benzene, toluene and the like; esters such as ethyl acetate, ethyl formate and the like; ketones such as acetone, methylethylketone and the like; amides such as N,N-dimethylformamide, N-methylpyrrolidone, N,N-dimethylacetamide and the like; acetonitrile; dichloromethane; chloroform; dimethyl sulfoxide; pyridine; water; and mixtures of solvents selected from these inert solvents.

The compound of the present invention is useful as a therapeutic or prophylactic agent for diseases in which CRF is considered to be involved. For this purpose, the compound of the present invention can be formulated into tablets, pills, capsules, granules, powders, solutions, emulsions, suspensions, injections and the like by a conventional preparation technique by adding conventional fillers, binders, disintegrators, pH-adjusting agents, solvents, etc.

The compound of the present invention can be administered to an adult patient in a dose of 0.1 to 500 mg per day in one portion or several portions orally or parenterally. The dose can be properly increased or decreased depending on the kind of a disease and the age, body weight and symptom of a patient.

EMBODIMENTS OF THE INVENTION

The present invention is concretely explained with reference to the following examples and test example, but is not limited thereto.

EXAMPLE 1

Synthesis of {1-[1-(4-methoxy-2,6-dimethyl-phenyl)-3,6-dimethyl-1H-pyrrolo[2,3-b]pyridin-4-yl]-piperidin-4-yl}-acetic acid (compound 1-013)

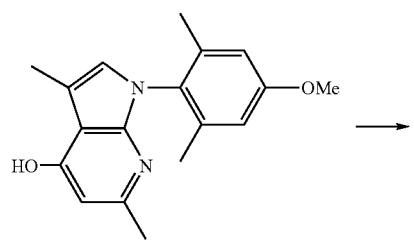

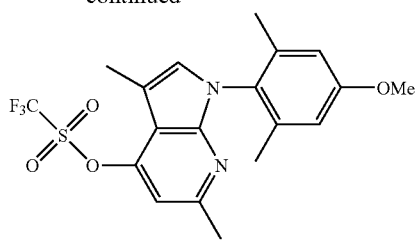

(1) Under $N_2$ atmosphere, to a mixture of 1-(4-methoxy-2,6-dimethyl-phenyl)-3,6-dimethyl-1H-pyrrolo[2,3-b]pyridin-4-ol (1.5 g), triethylamine (1.0 g) in $CHCl_3$ (9 mL), trifluoromethanesulfonic anhydride (1.0 mL) was added with cooling in an ice bath and the mixture was stirred for 30 minutes. The reaction was quenched with water and the mixture was extracted with $CHCl_3$. The organic phase was washed with saturated aqueous $NaHCO_3$ solution, dried over anhydrous $MgSO_4$ and filtered. The filtrate was concentrated under reduced pressure to obtain crude trifluoromethanesulfonic acid 1-(4-methoxy-2,6-dimethylphenyl)-3,6-dimethyl-1H-pyrrolo[2,3-b]pyridin-4-yl ester (2.19 g). This material was used in the next step without further purification.

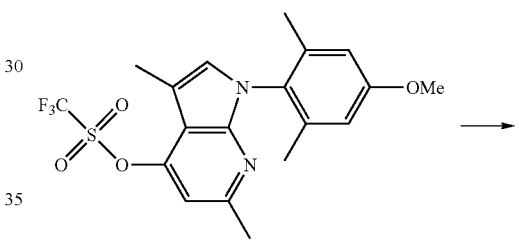

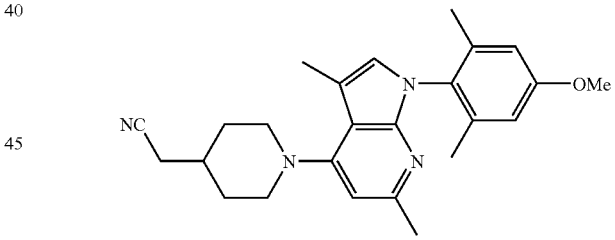

(2) A mixture of crude trifluoromethanesulfonic acid 1-(4-methoxy-2,6-dimethylphenyl)-3,6-dimethyl-1H-pyrrolo[2,3-b]pyridin-4-yl ester (1.1 g), N,N-diisopropylethylamine (0.65 g) and piperidin-4-yl-acetonitrile (1.6 g) was heated at 150° C. in a sealed tube for 7 hours. After cooling to room temperature, ethyl acetate and water were poured into the mixture, and separated. The aqueous phase was extracted with ethyl acetate, and the organic phase was dried over $MgSO_4$ and filtered. The filtrate was concentrated under reduced pressure and the residue was purified with column chromatography (silica gel: Wako gel C200, eluent: hexane: ethyl acetate=3/1) to obtain {1-[1-(4-methoxy-2,6-dimethylphenyl)-3,6-dimethyl-1H-pyrrolo[2,3-b]pyridin-4-yl]-piperidin-4-yl}-acetonitrile (0.58 g) as a pale yellow crystal.

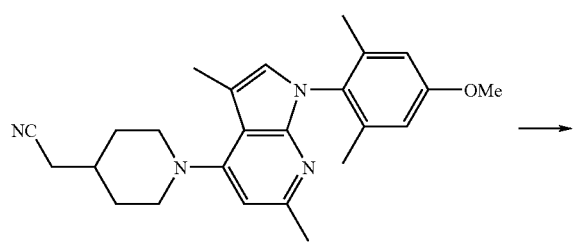

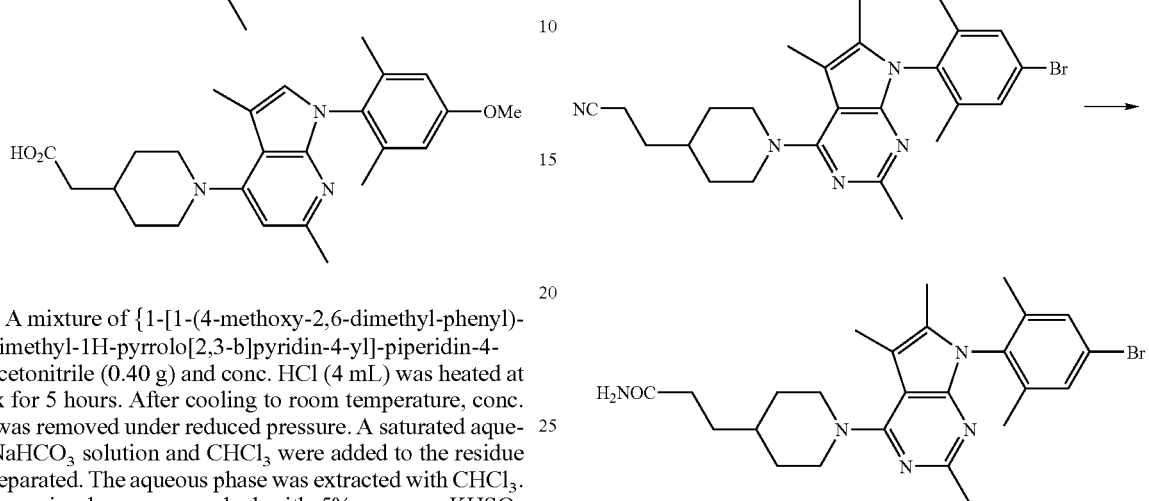

(3) A mixture of {1-[1-(4-methoxy-2,6-dimethyl-phenyl)-3,6-dimethyl-1H-pyrrolo[2,3-b]pyridin-4-yl]-piperidin-4-yl}-acetonitrile (0.40 g) and conc. HCl (4 mL) was heated at reflux for 5 hours. After cooling to room temperature, conc. HCl was removed under reduced pressure. A saturated aqueous NaHCO₃ solution and CHCl₃ were added to the residue and separated. The aqueous phase was extracted with CHCl₃. The organic phase was washed with 5% aqueous KHSO₄ solution, dried over MgSO₄ and filtered. The filtrate was concentrated under reduced pressure and the residue was purified with column chromatography (silica gel: Wako gel C200, eluent: CHCl₃:methanol=40/1) and the resulting solid was washed with methanol to obtain the title compound (0.21 g).

EXAMPLE 2

Synthesis of 3-{1-[7-(4-bromo-2,6-dimethyl-phenyl)-2,5,6-trimethyl-7H-pyrrolo[2,3-d]pyrimidin-4-yl]-piperidin-4-yl}-propionamide (compound 1-040)

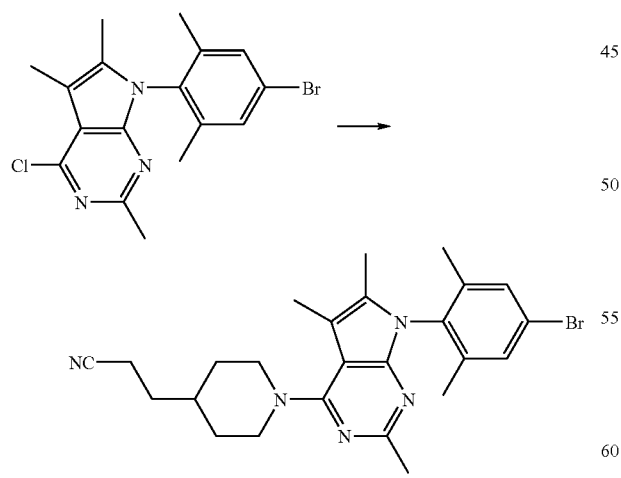

(1) A suspension of 7-(4-bromo-2,6-dimethyl-phenyl)-4-chloro-2,5,6-trimethyl-7H-pyrrolo[2,3-d]pyrimidine (2.0 g), 3-(piperidin-4-yl)propionitrile (1.4 g) and N,N-diisopropyl-ethylamine (1.4 g) in EtOH (4 mL) was heated at 100° C. in a sealed tube for 11 hours. After cooling to room temperature, the solvent was removed under reduced pressure. The residue was purified with column chromatography (silica gel: Wako gel C200, eluent: hexane:ethyl acetate:CHCl₃=8/2/1) to obtain 3-{1-[7-(4-bromo-2,6-dimethyl-phenyl)-2,5,6-trimethyl-7H-pyrrolo[2,3-d]pyrimidin-4-yl]-piperidin-4-yl}-propionitrile (2.0 g) as a white crystal.

(2) To 3-{1-[7-(4-bromo-2,6-dimethyl-phenyl)-2,5,6-trimethyl-7H-pyrrolo[2,3-d]pyrimidin-4-yl]-piperidin-4-yl}-propionitrile (0.40 g), H₂SO₄ (4 mL) was added and the mixture was stirred at room temperature for 5 hours. The reaction mixture was poured into ice, and then was made to alkaline by adding 4 M aqueous NaOH solution. The mixture was extracted with ethyl acetate and the organic phase and the organic phase was dried over Na₂SO₄. The desiccant was removed by filtration and the filtrate was concentrated under reduced pressure. The residue was purified with column chromatography (silica gel: Wako gel C200, eluent: CHCl₃:methanol=60/1) to obtain an oil. The oily product was crystallized from diethylether to obtain the title compound (0.33 g) as a white crystal.

EXAMPLE 3

Synthesis of (2-{1-[1-(4-bromo-2,6-dimethyl-phenyl)-3,6-dimethyl-1H-pyrrolo[2,3-b]pyridin-4-yl]-piperidin-4-yl}-ethyl)-phosphonic acid hydrochloride (compound 1-046)

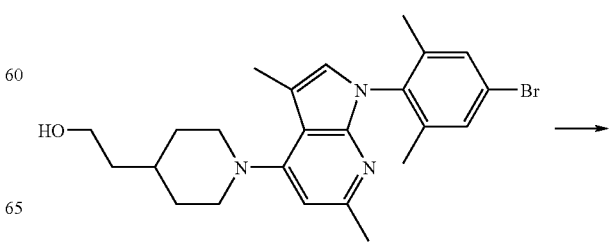

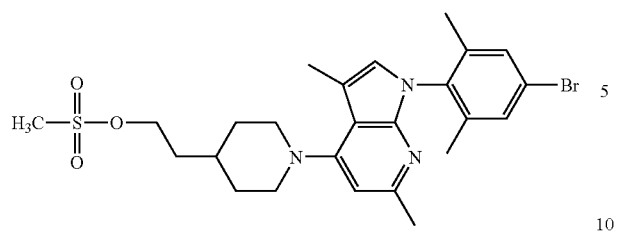

(1) To a solution of 2-{1-[1-(4-bromo-2,6-dimethyl-phenyl)-3,6-dimethyl-1H-pyrrolo[2,3-b]pyridin-4-yl]-piperidin-4-yl}-ethanol (0.93 g), which was prepared in the similar method as shown in example 1, in CHCl₃ (10 mL), was added methanesulfonyl chloride (0.47 g) and pyridine (0.64 g) and the mixture was stirred at room temperature for 3 hours. Water was added into the reaction mixture and the mixture was extracted with CHCl₃. The organic phase was washed with water and brine, dried over Na₂SO₄ and filtered. The filtrate was concentrated under reduced pressure to obtain a brown oil. The oily product was crystallized from diisopropylether to obtain methanesulfonic acid 2-{1-[1-(4-bromo-2,6-dimethyl-phenyl)-3,6-dimethyl-1H-pyrrolo[2,3-b]pyridin-4-yl]-piperidin-4-yl}-ethyl ester (1.0 g).

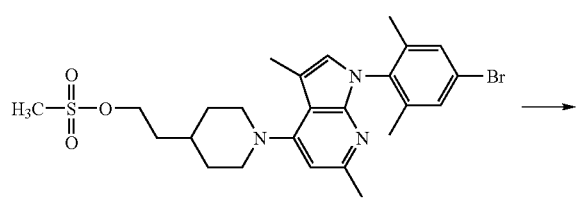

(2) A mixture of methanesulfonic acid 2-{1-[1-(4-bromo-2,6-dimethyl-phenyl)-3,6-dimethyl-1H-pyrrolo[2,3-b]pyridin-4-yl]-piperidin-4-yl}-ethyl ester (0.70 g) and NaI (0.59 g) in acetone (14 mL) was heated at reflux for 3 hours. After cooling to room temperature, water was added and the mixture was extracted with ethyl acetate. The organic phase was washed with water, dried over Na₂SO₄ and filtered. The filtrate was concentrated under reduced pressure. The residue was purified with column chromatography (silica gel: Wako gel C200, eluent: hexane:ethyl acetate=10/1) to obtain 1-(4-bromo-2,6-dimethyl-phenyl)-4-[4-(2-iodo-ethyl)-piperidin-1-yl]-3,6-dimethyl-1H-pyrrolo[2,3-b]pyridine (0.65 g) as a white crystal.

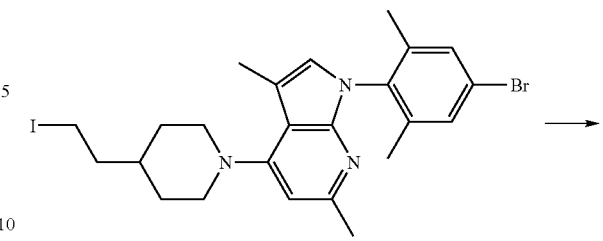

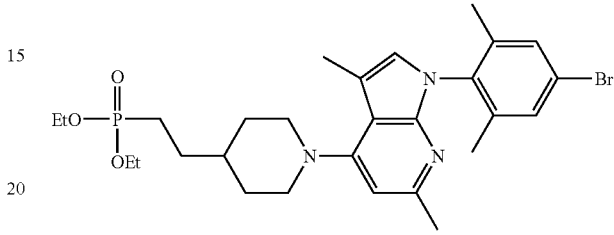

(3) Under N₂ atmosphere, a mixture of 1-(4-bromo-2,6-dimethyl-phenyl)-4-[4-(2-iodo-ethyl)-piperidin-1-yl]-3,6-dimethyl-1H-pyrrolo[2,3-b]pyridine (0.25 g) and triethyl phosphite (10 mL) was heated at 160° C. for 4.5 hours. After the reaction was completed, excess triethyl phosphate was removed under reduced pressure. The residue was purified with column chromatography (silica gel: Wako gel C200, eluent: hexane:ethyl acetate=1/1) to obtain a colorless oil. The oily product was crystallized from diisopropylether (10 mL) to provide (2-{1-[1-(4-bromo-2,6-dimethyl-phenyl)-3,6-dimethyl-1H-pyrrolo[2,3-b]pyridin-4-yl]-piperidin-4-yl}-ethyl)-phosphonic acid diethyl ester (0.16 g) as a white crystal.

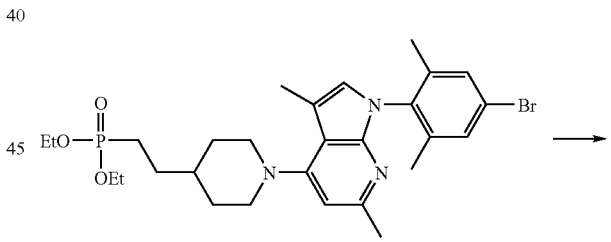

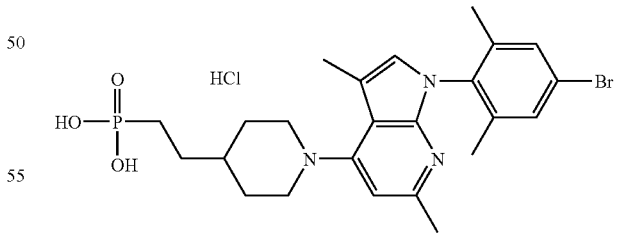

(4) A mixture of 2-{1-[1-(4-bromo-2,6-dimethyl-phenyl)-3,6-dimethyl-1H-pyrrolo[2,3-b]pyridin-4-yl]-piperidin-4-yl}-ethyl)-phosphonic acid diethyl ester (67 mg) and 6 M HCl (4 mL) was heated at reflux for 10 hours. And then 12 M HCl (2 mL) was added and the reaction mixture was heated at reflux for 10 hours. The reaction mixture was concentrated under reduced pressure to obtain the title compound as an amorphous (13 mg).

EXAMPLE 4

Synthesis of 2-{1-[1-(4-bromo-2,6-dimethyl-phenyl)-3,6-dimethyl-1H-pyrrolo[2,3-b]pyridin-4-yl]-piperidin-4-yl}-ethanesulfonic acid (compound 1-048)

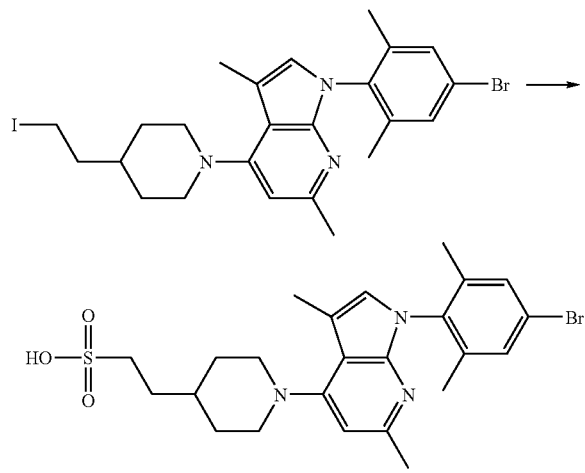

A mixture of 1-(4-bromo-2,6-dimethyl-phenyl)-4-[4-(2-iodo-ethyl)-piperidin-1-yl]-3,6-dimethyl-1H-pyrrolo[2,3-b]pyridine (0.25 g), Na$_2$SO$_3$ (0.28 g), tetrabutylammonium iodide (16 mg), ethanol (5 mL), tetrahydrofuran (5 mL) and water (3 mL) was heated at reflux for 10 hours. The reaction mixture was concentrated under reduced pressure. The residue was purified with column chromatography (silica gel: Wako gel C200, eluent: ethyl acetate:methanol=5/1) to obtain the title compound (56 mg) as a yellow amorphous.

EXAMPLE 5

Synthesis of {1-[1-(4-bromo-2,6-dimethylphenyl)-3,6-dimethyl-1H-pyrrolo[2,3-b]pyridin-4-yl]piperidin-4-yl}acetic acid ethyl ester hydrochloride (compound 1-050)

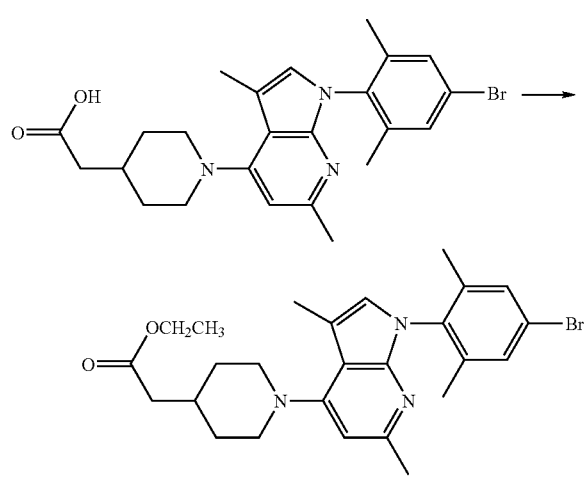

To a solution of {1-[1-(4-bromo-2,6-dimethyl-phenyl)-3,6-dimethyl-1H-pyrrolo[2,3-b]pyridin-4-yl]-piperidin-4-yl}-acetic acid (100 mg) in CHCl$_3$ (4 mL) in an ice cooling bath was added ethanol (20 mg), 1-(3-dimethylaminopropyl)-3-ethylcarbodiimide hydrochloride (61 mg), and dimethylaminopyridine (26 mg), and the mixture was stirred at room temperature for 1 hour. The reaction mixture was poured into ethyl acetate and water, and separated. The organic phase was washed with brine, dried over Na$_2$SO$_4$, and filtered. The filtrate was concentrated under reduced pressure and the residue was purified with column chromatography (silica gel: Wako gel C200, eluent: hexane:ethyl acetate=4/1) to obtain {1-[1-(4-bromo-2,6-dimethylphenyl)-3,6-dimethyl-1H-pyrrolo[2,3-b]pyridin-4-yl]piperidin-4-yl}acetic acid ethyl ester (99 mg). {1-[1-(4-Bromo-2,6-dimethylphenyl)-3,6-dimethyl-1H-pyrrolo[2,3-b]pyridin-4-yl]piperidin-4-yl}acetic acid ethyl ester was dissolved in ethanol (2 mL) and 4 M HCl in ethyl acetate solution (60 μL) was added into the solution with cooling in an ice bath. After stirring at room temperature, the reaction mixture was concentrated under reduced pressure, and the residue was crystallized from diisopropylether (1 mL). The crystal was collected by filtration to obtain the title compound. (95 mg)

EXAMPLE 6

Synthesis of {1-[1-(4-bromo-2,6-dimethyl-phenyl)-3,6-dimethyl-1H-pyrrolo[2,3-b]pyridin-4-yl]-piperidin-4-yl}-acetic acid 1-cyclohexyloxycarbonyloxy-ethyl ester (compound 1-071)

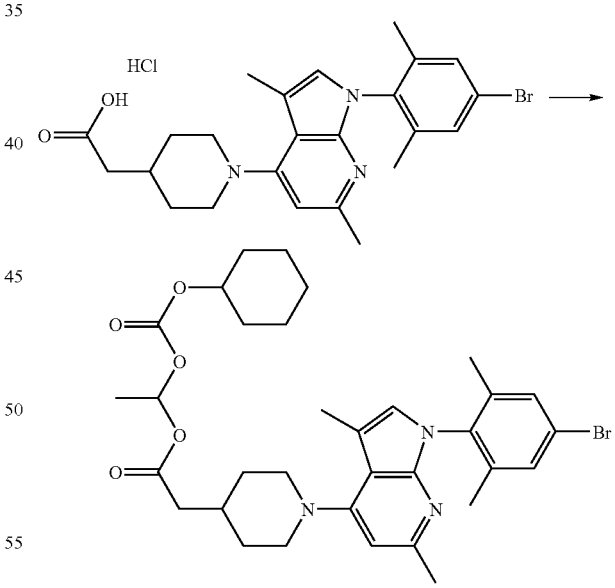

A suspension of {1-[1-(4-bromo-2,6-dimethyl-phenyl)-3,6-dimethyl-1H-pyrrolo[2,3-b]pyridin-4-yl]-piperidin-4-yl}-acetic acid hydrochloride (300 mg), 1-chloroethyl cyclohexyl carbonate (293 mg), potassium carbonate (196 mg) and NaI (213 mg) in DMF (3 mL) was heated at 60° C. for 3 hours. After cooling to room temperature, water was added and the mixture was extracted with ethyl acetate. The organic phase was washed with brine and concentrated under reduced pressure. The residue was purified with column chromatography (silica gel: Wako gel C200, eluent: hexane:ethyl acetate=4/1) to obtain the title compound (225 mg) as a colorless oil.

EXAMPLE 7

Synthesis of (S)-2-(2-{1-[1-(4-bromo-2,6-dimethyl-phenyl)-3,6-dimethyl-1H-pyrrolo[2,3-b]pyridin-4-yl]-piperidin-4-yl}-acetylamino)-3-phenyl-propionic acid (compound 1-074)

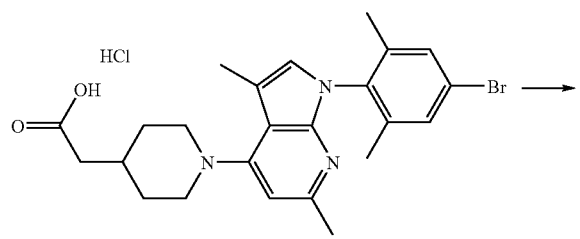

(1) To a solution of {1-[1-(4-bromo-2,6-dimethyl-phenyl)-3,6-dimethyl-1H-pyrrolo[2,3-b]pyridin-4-yl]-piperidin-4-yl}-acetic acid hydrochloride (300 mg), L-phenylalanine ethyl ester hydrochloride (204 mg), 1-hydroxybenzotriazole (108 mg) and triethylamine (90 mg) in DMF (3 mL) in an ice cooling bath was added 1-(3-dimethylaminopropyl)-3-ethyl-carbodiimide hydrochloride (170 mg), and the mixture was stirred at room temperature for 4 hours. Water was added into the reaction mixture and the mixture was extracted with ethyl acetate. The organic phase was washed with a saturated aqueous NaHCO₃ solution and brine, and concentrated under reduced pressure. The residue was purified with column chromatography (silica gel: Wako gel C200, eluent: hexane:ethyl acetate=1/1) to obtain (S)-2-(2-{1-[1-(4-bromo-2,6-dimethyl-phenyl)-3,6-dimethyl-1H-pyrrolo[2,3-b]pyridin-4-yl]-piperidin-4-yl}-acetylamino)-3-phenyl-propionic acid ethyl ester (222 mg) as a colorless oil.

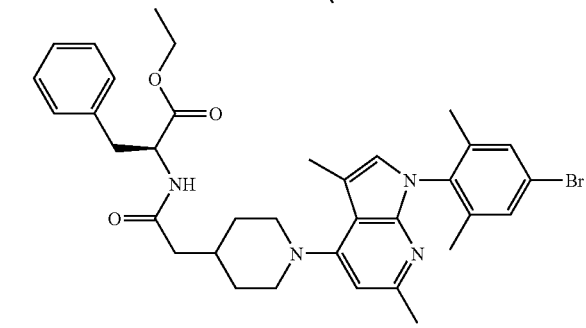

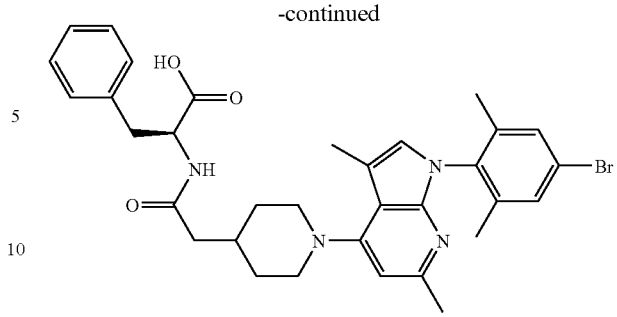

(2) A mixture of (S)-2-(2-{1-[1-(4-bromo-2,6-dimethyl-phenyl)-3,6-dimethyl-1H-pyrrolo[2,3-b]pyridin-4-yl]-piperidin-4-yl}-acetylamino)-3-phenyl-propionic acid ethyl ester (140 mg), 4 M NaOH (1 mL) and EtOH (2 mL) was stirred at room temperature for 24 hours. 1 M KHSO₄ (10 mL) was added into the reaction mixture and the mixture was extracted with ethyl acetate. The organic phase was washed with brine, and concentrated under reduced pressure. The residue was purified with column chromatography (silica gel: Wako gel C200, eluent: CHCl₃:MeOH=9/1) to obtain the title compound (35 mg) as an amorphous.

EXAMPLE 8

Synthesis of 4-{1-[7-(4-bromo-2,6-dimethyl-phenyl)-2,5,6-trimethyl-7H-pyrrolo[2,3-d]pyrimidin-4-yl]-piperidin-4-yl}-2-cyano-butyric acid ethyl ester (compound 1-063)

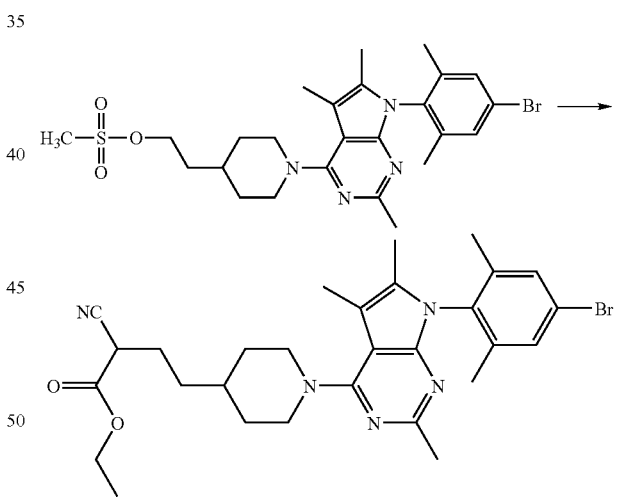

Under N₂ atmosphere, to a solution of cyanoacetic acid ethyl ester (93 mg) in THF (3 mL) was added sodium hydride (33 mg) and the mixture was stirred for 30 minutes. Methanesulfonic acid 2-{1-[7-(4-bromo-2,6-dimethyl-phenyl)-2,5,6-trimethyl-7H-pyrrolo[2,3-d]pyrimidin-4-yl]-piperidin-4-yl}-ethyl ester (300 mg) was added, and the mixture was heated at reflux for 3 hours. Cyanoacetic acid ethyl ester (93 mg) was added, and the reaction mixture was heated at reflux for 1 hour. And then NaI (7 mg) was added, and the mixture was heated at reflux for 2 hours. After cooling to room temperature, 5% aqueous KHSO₄ solution was added into the reaction mixture and the mixture was extracted with ethyl acetate. The organic phase was dried over MgSO₄ and filtered

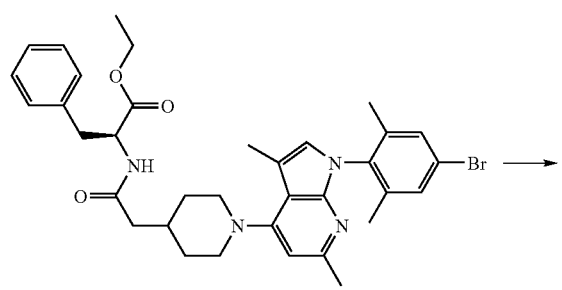

and the filtrate was concentrated under reduced pressure. The residue was purified with column chromatography (silica gel: Wako gel C200, eluent: hexane:ethyl acetate=4/1) to obtain the title compound (57 mg) as a colorless oil.

EXAMPLE 9

Synthesis of {1-[1-(4-bromo-2,6-dimethyl-phenyl)-3,6-dimethyl-1H-pyrrolo[2,3-b]pyridin-4-yl]-piperidin-4-yl}-acetic acid

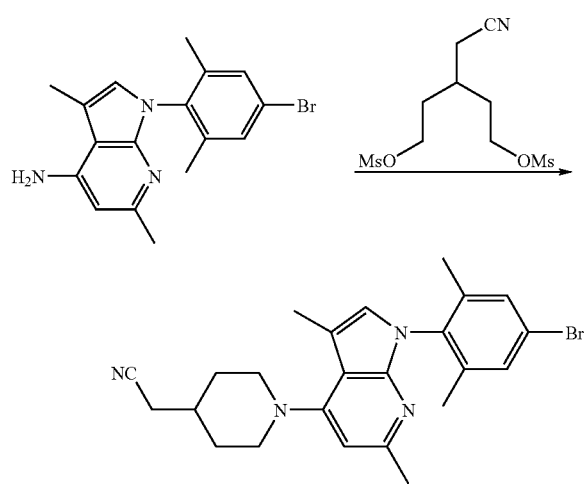

(1) A mixture of 1-(4-bromo-2,6-dimethyl-phenyl)-3,6-dimethyl-1H-pyrrolo[2,3-b]pyridin-4-ylamine (10.0 g), methanesulfonic acid 3-cyanomethyl-5-methanesulfonyloxy-pentyl ester (11.3 g) and N,N-diisopropylethylamine (8.25 g) in N-methylpyrrolidone (10 mL) was heated at 135° C. for 4 hours. Methanesulfonic acid 3-cyanomethyl-5-methanesulfonyloxy-pentyl ester (2.60 g) was added to the reaction mixture and the mixture was heated at 135° C. for 4.5 hours. After cooling to room temperature, the reaction mixture was poured into a mixture of ethyl acetate, hexane and water (10/1/3), and separated. The aqueous phase was extracted with a mixture of ethyl acetate and hexane (10/1). The combined organic phase was washed with brine, dried over MgSO$_4$, and filtered, and concentrated under reduced pressure. The residue was purified with column chromatography (silica gel: Wako gel C200, eluent: hexane:ethyl acetate:CHCl$_3$=4/1/0.5) to obtain a solid. The solid was crystallized from diisopropylether to obtain {1-[1-(4-bromo-2,6-dimethyl-phenyl)-3,6-dimethyl-1H-pyrrolo[2,3-b]pyridin-4-yl]-piperidin-4-yl}-acetonitrile (8.61 g) as a solid.

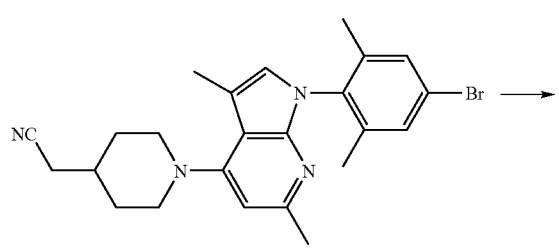

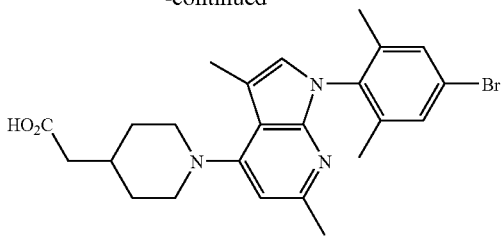

(2) A mixture of {1-[1-(4-bromo-2,6-dimethyl-phenyl)-3,6-dimethyl-1H-pyrrolo[2,3-b]pyridin-4-yl]-piperidin-4-yl}-acetonitrile (10.0 g) and conc. HCl (100 mL) was heated at reflux for 10 h. After evaporating conc. HCl under reduced pressure. To the residue, aqueous NaHCO$_3$ solution and CHCl$_3$ were added and partitioned. The organic phase was washed with H$_2$O, 1M aqueous KHSO$_4$ solution and brine, dried over Na$_2$SO$_4$, and filtered, and concentrated under reduced pressure. The residue was purified with column chromatography (silica gel: Wako gel C200, eluent: hexane:ethyl acetate=1/1) to obtain a solid. The solid was recrystallized from EtOH and washed with H$_2$O to give the title compound (6.0 g) as a crystal.

REFERENCE EXAMPLE 1

Synthesis of methanesulfonic acid 3-cyanomethyl-5-methanesulfonyloxy-pentyl ester

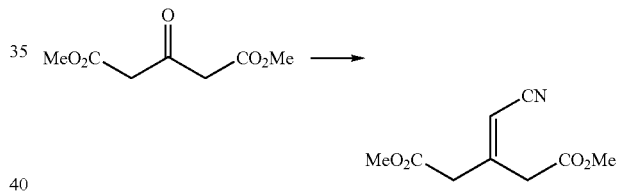

(1) To a solution of 3-oxo-pentanedioic acid dimethyl ester (523 g) in toluene (750 mL), cyanoacetic acid (511 g), NH$_4$OAc (46.3 g) and acetic acid (90.1 g) were added and heated at reflux with dehydrating by Dean-Stark apparatus for 8 h. After cooling to room temperature, the reaction mixture was washed with water, saturated aqueous NaHCO$_3$ solution and brine. The organic phase was dried over MgSO$_4$, filtered, and concentrated under reduced pressure to give crude 3-cyanomethylene-pentanedioic acid dimethyl ester (403 g) as an oil. $^1$H NMR (200 MHz, CDCl$_3$) δ ppm 3.39 (d, J=0.88 Hz, 2 H), 3.62 (s, 2 H), 3.72 (s, 3 H), 3.74 (s, 3 H), 5.51 (s, 1 H).

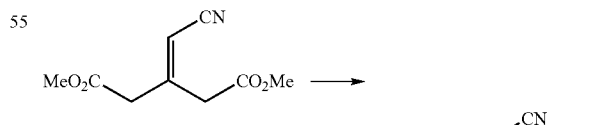

(2) To a solution of crude 3-cyanomethylene-pentanedioic acid dimethyl ester (403 g) in methanol (500 mL), 5% Pd—C was added and the mixture was stirred at room temperature for 4 days. The Pd—C was removed by filtration and the filtrate was concentrated under reduced pressure to give crude 3-cyanomethyl-pentanedioic acid dimethyl ester (212 g). The residue was purified by distillation to obtain 3-cyanomethyl-pentanedioic acid dimethyl ester (bp 130-150° C., 133 Pa) as a yellow oil. $^1$H NMR (200 MHz, CDCl$_3$) δ ppm 2.46-2.61 (m, 5 H) 2.62-2.78 (m, 4 H) 3.71 (s, 6 H).

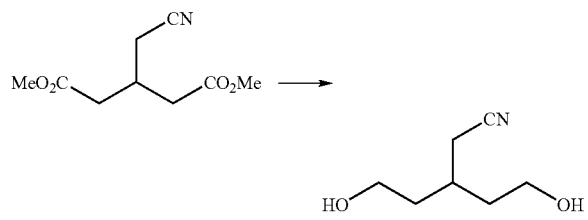

(3) Under nitrogen atmosphere, 3-cyanomethyl-pentanedioic acid dimethyl ester (212 g) was added to a suspension of LiAlH$_4$ (50.0 g) in THF (1.8 L) at −20° C. After stirring for 30 min., H$_2$O (200 mL) was slowly added to the reaction mixture. The insoluble material was removed by filtration and the filtrate was concentrated under reduced pressure to obtain 5-hydroxy-3-(2-hydroxy-ethyl)-pentanenitrile (131 g). $^1$H NMR (200 MHz, CDCl$_3$) δ ppm 1.38-1.91 (m, 4 H) 1.98-2.36 (m, 1 H) 2.50 (d, J=5.71 Hz, 2 H) 3.51-3.90 (m, 4 H).

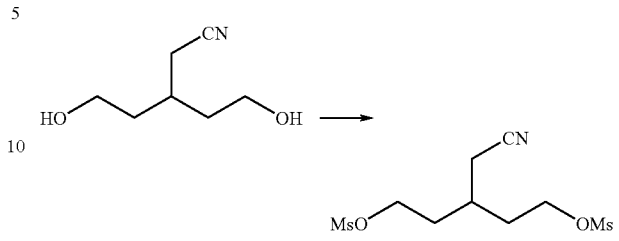

(4) Under nitrogen atmosphere, a solution of 5-hydroxy-3-(2-hydroxy-ethyl)-pentanenitrile (100 g) and Et$_3$N (170 g) in THF (500 mL) was cooled to −15° C. and MsCl (168 g) was added slowly and the reaction mixture was stirred at room temperature for 1.5 h. After adding H$_2$O (1.2 L) into the reaction mixture, and the mixture was stirred at room temperature for 30 min. The precipitate was collected by filtration and dried to obtain the title compound (145 g) as a pale brown crystal. $^1$H NMR (200 MHz, CDCl$_3$) δ ppm 1.65-2.09 (m, 5 H) 2.68 (d, J=5.75 Hz, 2 H) 3.20 (s, 6 H) 4.29 (t, J=6.45 Hz, 4 H).

TABLE 1*[1]

| Com. No. | Ex. No | X—(CHR$^3$)$_n$—(CR$^1$R$^2$)$_m$ R$^4$—(N)—R$^5$ | Y | R$^6$ | R$^7$ | R$^8$ | —Ar | melting point (° C.) (solvent for crystallization) |
|---|---|---|---|---|---|---|---|---|
| 1-001 | 1 | HO$_2$C—[piperidine]—N— | N | CH$_3$ | CH$_3$ | CH$_3$ | 2,6-dimethyl-4-bromophenyl | 205-207 (EtOAc) |
| 1-002 | 1 | HO$_2$C—[piperidine]—N— | N | CH$_3$ | CH$_3$ | H | 2,6-dimethyl-4-bromophenyl | 229-231 (EtOAc) |
| 1-003 | 1 | HO$_2$C—[piperidine]—N— | CH | CH$_3$ | CH$_3$ | CH$_3$ | 2,6-dimethyl-4-bromophenyl | 140-142*[2] (Et$_2$O) |

TABLE 1*1-continued
| Com. No. | Ex. No | X—(CHR³)ₙ—(CR¹R²)ₘ, R⁴, R⁵ (ring) | Y | R⁶ | R⁷ | R⁸ | —Ar | melting point (°C.) (solvent for crystallization) |
|---|---|---|---|---|---|---|---|---|
| 1-004 | 1 | 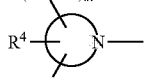 | CH | CH₃ | CH₃ | H | 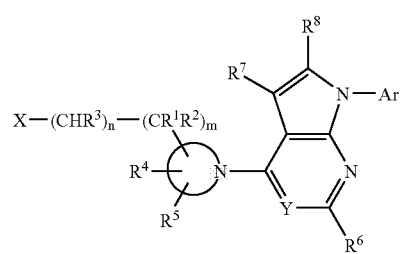 | 223-225 (EtOH/EtOAc) |
| 1-005 | 1 | 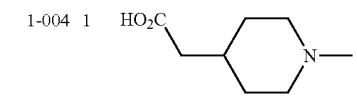 | CH | CH₃ | CH₃ | CH₃ | 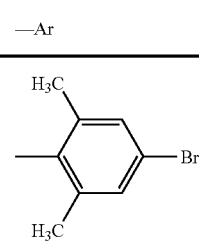 | 144-146 (EtOAc) |
| 1-006 | 1 | 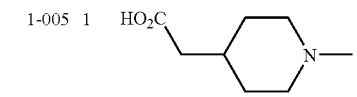 | CH | CH₃ | CH₃ | H | 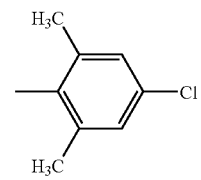 | 207-209 (EtOAc) |
| 1-007 | 1 | 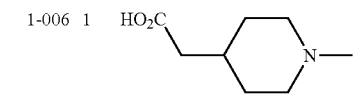 | CH | CH₃ | CH₃ | CH₃ | 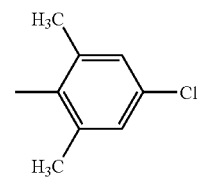 | 148-150 (EtOAc) |
| 1-008 | 1 | 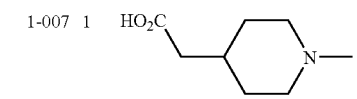 | CH | CH₃ | CH₃ | H | 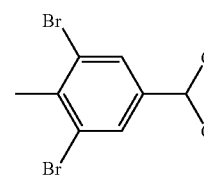 | 208-210 (EtOAc) |
| 1-009 | 1 | 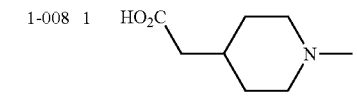 | CH | CH₃ | CH₃ | H | 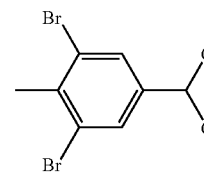 | 236-238 (EtOAc) |

TABLE 1*¹-continued
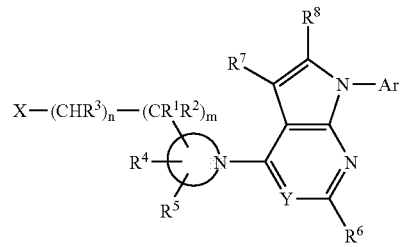
| Com. No. | Ex. No | X—(CHR³)ₙ—(CR¹R²)ₘ with R⁴, R⁵, N | Y | R⁶ | R⁷ | R⁸ | —Ar | melting point (° C.) (solvent for crystallization) |
|---|---|---|---|---|---|---|---|---|
| 1-010 | 1 | 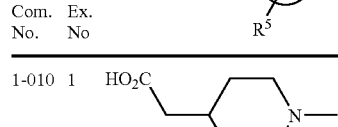 | CH | CH₃ | CH₃ | H | 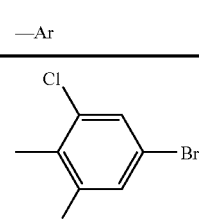 | 230-232 (EtOAc) |
| 1-011 | 1 | 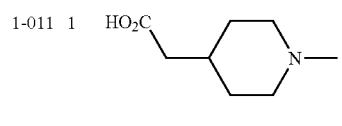 | CH | CH₃ | CH₃ | H | 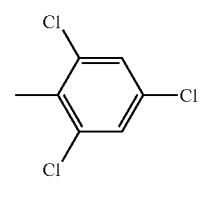 | 231-233 (EtOAc) |
| 1-012 | 1 | 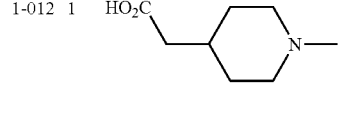 | CH | CH₃ | CH₃ | H | 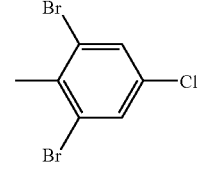 | 235-237 (EtOAc) |
| 1-013 | 1 | 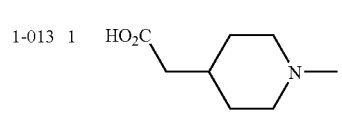 | CH | CH₃ | CH₃ | H | 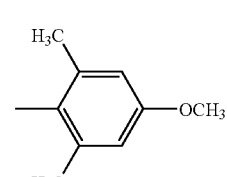 | 215-217 (MeOH) |
| 1-014 | 1 | 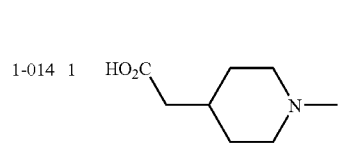 | CH | CH₃ | CH₃ | H | 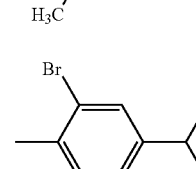 | 193-195 (EtOAc) |
| 1-015 | 1 | 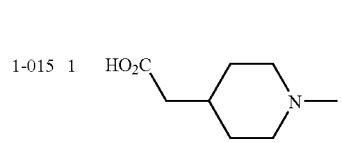 | CH | CH₃ | CH₃ | H | 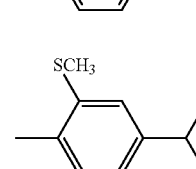 | 216-218 (EtOAc) |
| 1-016 | 1 | 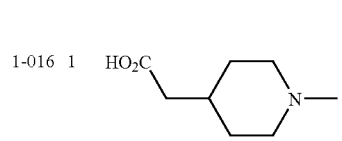 | CH | CH₃ | CH₃ | H | 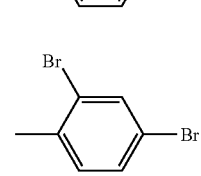 | 233-235 (EtOAc) |

TABLE 1*¹-continued
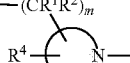
| Com. No. | Ex. No | X—(CHR³)ₙ—(CR¹R²)ₘ / R⁴ / R⁵ | Y | R⁶ | R⁷ | R⁸ | —Ar | melting point (° C.) (solvent for crystallization) |
|---|---|---|---|---|---|---|---|---|
| 1-017 | 1 | 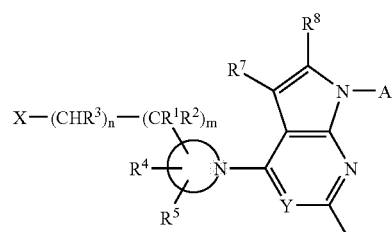 | N | CH₃ | CH₃ | CH₃ | 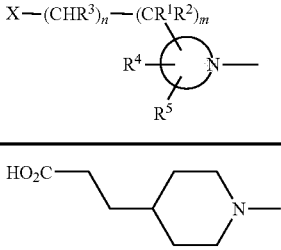 | 255-257 (EtOH/EtOAc) |
| 1-018 | 1 | 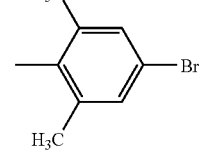 | N | CH₃ | CH₃ | H | 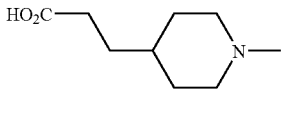 | 277-279 (EtOAc) |
| 1-019 | 1 | 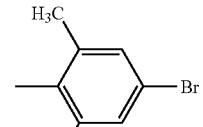 | CH | CH₃ | CH₃ | CH₃ | 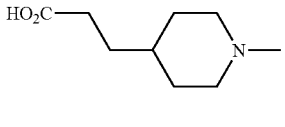 | 271-273 (EtOAc) |
| 1-020 | 1 | 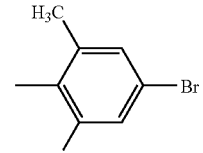 | CH | CH₃ | CH₃ | H | 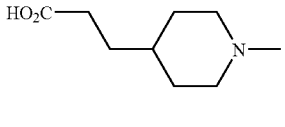 | 275-277 (decomp.) (EtOAc/EtOH) |
| 1-021 | 1 | 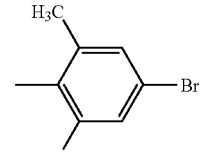 | CH | CH₃ | CH₃ | CH₃ | 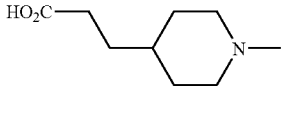 | 249-251 (EtOAc) |
| 1-022 | 1 | 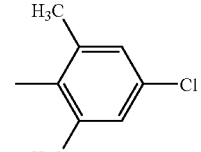 | CH | CH₃ | CH₃ | H | 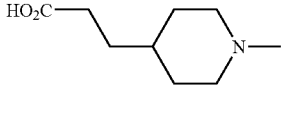 | 261-263 (EtOAc) |

TABLE 1*¹-continued

| Com. No. | Ex. No | X—(CHR³)ₙ—(CR¹R²)ₘ / R⁴ / R⁵ | Y | R⁶ | R⁷ | R⁸ | —Ar | melting point (° C.) (solvent for crystallization) |
|---|---|---|---|---|---|---|---|---|
| 1-023 | 1 | HO₂C-CH₂-(4-piperidinyl)-N-CH₃ | CH | CH₃ | CH₃ | CH₃ | 2,6-dibromo-4-isopropylphenyl | 275-277 (EtOAc) |
| 1-024 | 1 | HO₂C-CH₂-(4-piperidinyl)-N-CH₃ | CH | CH₃ | CH₃ | H | 2,6-dibromo-4-isopropylphenyl | 232-234 (EtOAc) |
| 1-025 | 1 | HO₂C-CH₂-(4-piperidinyl)-N-CH₃ | CH | CH₃ | CH₃ | H | 4-bromo-2,6-dichlorophenyl | 265-267 (EtOAc) |
| 1-026 | 1 | HO₂C-CH₂-(4-piperidinyl)-N-CH₃ | CH | CH₃ | CH₃ | H | 2,4,6-trichlorophenyl | 254-256 (EtOAc) |
| 1-027 | 1 | HO₂C-CH₂-(4-piperidinyl)-N-CH₃ | CH | CH₃ | CH₃ | H | 2,6-dibromo-4-chlorophenyl | 260-262 (EtOAc) |
| 1-028 | 1 | HO₂C-CH₂-(4-piperidinyl)-N-CH₃ | CH | CH₃ | CH₃ | H | 4-methoxy-2,6-dimethylphenyl | 253-255 (EtOAc/IPE) |
| 1-029 | 1 | HO₂C-CH₂-(4-piperidinyl)-N-CH₃ | CH | CH₃ | CH₃ | H | 2-bromo-4-isopropylphenyl | 232-234 (EtOAc) |

TABLE 1*¹-continued
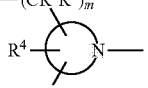
| Com. No. | Ex. No | X—(CHR³)ₙ—(CR¹R²)ₘ R⁴—N— R⁵ | Y | R⁶ | R⁷ | R⁸ | —Ar | melting point (° C.) (solvent for crystallization) |
|---|---|---|---|---|---|---|---|---|
| 1-030 | 1 | 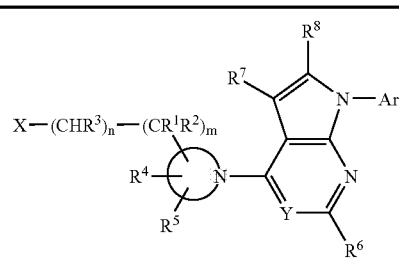 | CH | CH₃ | CH₃ | H | 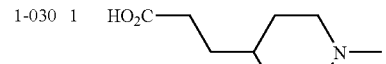 | 250-252 (EtOAc) |
| 1-031 | 1 | 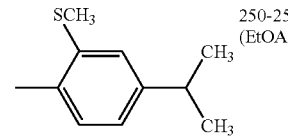 | CH | CH₃ | CH₃ | H | 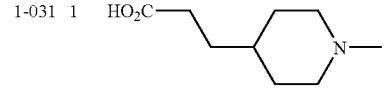 | 248-250 (EtOAc) |
| 1-032 | 1 | 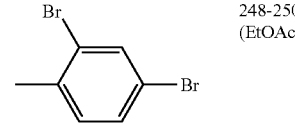 | CH | CH₃ | CH₃ | CH₃ | 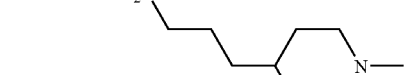 | 181-183 (EtOAc) |
| 1-033 | 1 | 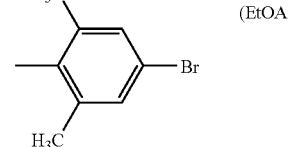 | CH | CH₃ | CH₃ | H | 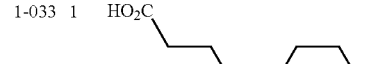 | 200-202 (EtOAc) |
| 1-034 | 1 | 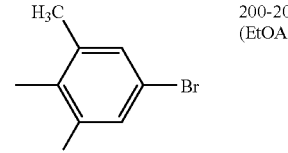 | CH | CH₃ | CH₃ | H | 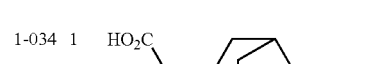 | 244-246 (EtOAc) |
| 1-035 | 1 | 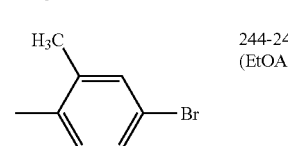 | CH | CH₃ | CH₃ | H |  | 250-252 (EtOAc) |
| 1-036 | 1 | 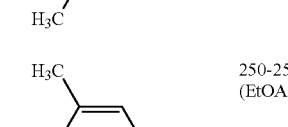 | CH | CH₃ | CH₃ | H | 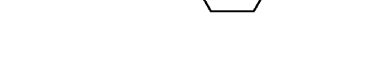 | 251-253 (EtOAc) |

TABLE 1*1-continued

| Com. No. | Ex. No | X—(CHR³)ₙ—(CR¹R²)ₘ with R⁴,R⁵,N substituents | Y | R⁶ | R⁷ | R⁸ | —Ar | melting point (° C.) (solvent for crystallization) |
|---|---|---|---|---|---|---|---|---|
| 1-037 | 2 | H₂NOC—[4-(N-methylpiperidinyl)methyl] | N | CH₃ | CH₃ | CH₃ | 4-Br-2,6-(CH₃)₂-phenyl | 254-256 (IPE/EtOAc) |
| 1-038 | 2 | H₂NOC—[4-(N-methylpiperidinyl)methyl] | N | CH₃ | CH₃ | H | 4-Br-2,6-(CH₃)₂-phenyl | 252-254 (IPE/EtOAc) |
| 1-039 | 2 | H₂NOC—[4-(N-methylpiperidinyl)methyl] | CH | CH₃ | CH₃ | H | 4-Br-2,6-(CH₃)₂-phenyl | 214-216*² (EtOAc/EtOH) |
| 1-040 | 2 | H₂NOC—CH₂—[4-(N-methylpiperidinyl)] | N | CH₃ | CH₃ | CH₃ | 4-Br-2,6-(CH₃)₂-phenyl | 126-128 (Et₂O) |
| 1-041 | 2 | H₂NOC—CH₂—[4-(N-methylpiperidinyl)] | N | CH₃ | CH₃ | H | 4-Br-2,6-(CH₃)₂-phenyl | 233-235 (IPE/EtOAc) |
| 1-042 | 2 | H₂NOC—CH₂—[4-(N-methylpiperidinyl)] | CH | CH₃ | CH₃ | H | 4-Br-2,6-(CH₃)₂-phenyl | 215-216*² (EtOAc/EtOH) |

TABLE 1*1-continued
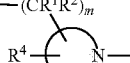
| Com. No. | Ex. No | X—(CHR³)ₙ—(CR¹R²)ₘ \ R⁴—N— / R⁵ | Y | R⁶ | R⁷ | R⁸ | —Ar | melting point (° C.) (solvent for crystallization) |
|---|---|---|---|---|---|---|---|---|
| 1-043 | 3 | 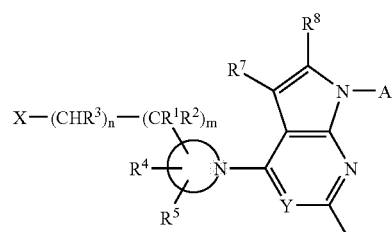 | CH | CH₃ | CH₃ | H | 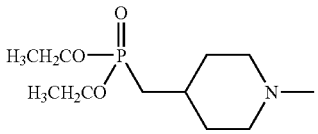 | 137-139 (IPE) |
| 1-044 | 3 | 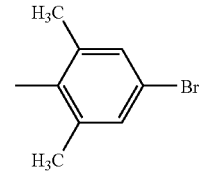 | CH | CH₃ | CH₃ | H | 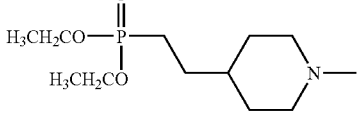 | 127-128 (IPE) |
| 1-045 | 3 | 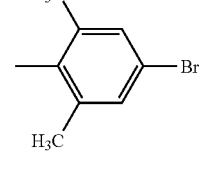 | CH | CH₃ | CH₃ | H | 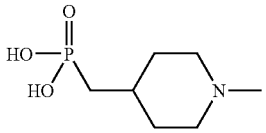 | amorphous*² |
| 1-046 | 3 | 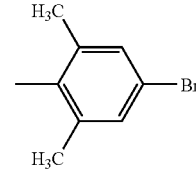 | CH | CH₃ | CH₃ | H | 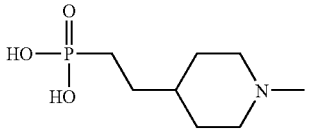 | amorphous*² |
| 1-047 | 4 | 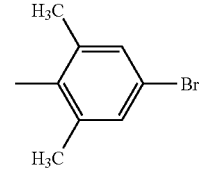 | CH | CH₃ | CH₃ | H | 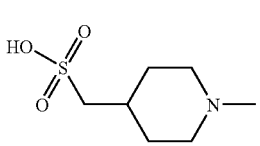 | amorphous |
| 1-048 | 4 | 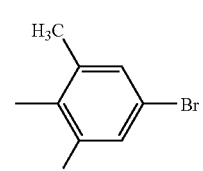 | CH | CH₃ | CH₃ | H | 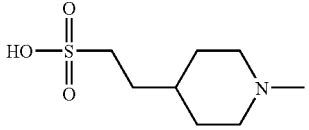 | amorphous |

TABLE 1*¹-continued

| Com. No. | Ex. No | X—(CHR³)ₙ—(CR¹R²)ₘ / R⁴, R⁵, N | Y | R⁶ | R⁷ | R⁸ | —Ar | melting point (° C.) (solvent for crystallization) |
|---|---|---|---|---|---|---|---|---|
| 1-049 | 1 | H₂N-S(=O)₂-CH₂CH₂-(4-piperidinyl)-N-CH₃ | CH | CH₃ | CH₃ | H | 4-Br-2,6-(CH₃)₂-phenyl | 208-210*² (EtOH/EtOAc) |
| 1-050 | 5 | EtO₂C-CH₂-(4-piperidinyl)-N-CH₃ | CH | CH₃ | CH₃ | H | 4-Br-2,6-(CH₃)₂-phenyl | 146-148*² (IPE) |
| 1-051 | 1 | HO₂C-CH₂-(4-piperidinyl)-N-CH₃ | N | CH₃ | CH₃ | H | 2,6-Cl₂-4-CF₃-phenyl | 178-180*³ |
| 1-052 | 1 | HO₂C-CH₂-(4-piperidinyl)-N-CH₃ | N | CH₃ | CH₃ | H | 2,6-Cl₂-4-OCF₃-phenyl | 191-193 (IPE) |
| 1-053 | 1 | HO₂C-CH₂-(4-piperidinyl)-N-CH₃ | N | CH₃ | CH₃ | H | 2-SCH₃-4-(CH(CH₃)₂)-phenyl | 136-138*² (EtOAc) |
| 1-054 | 1 | HO₂C-CH₂-CH₂-(4-piperidinyl)-N-CH₃ | N | CH₃ | CH₃ | H | 2-SCH₃-4-(CH(CH₃)₂)-phenyl | 141-143*² (EtOAc) |
| 1-055 | 1 | HO₂C-CH₂-CH₂-CH₂-(4-piperidinyl)-N-CH₃ | N | CH₃ | CH₃ | H | 2-SCH₃-4-(CH(CH₃)₂)-phenyl | 138-140*² (EtOAc) |

TABLE 1*1-continued

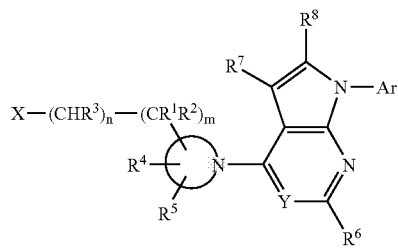

| Com. No. | Ex. No | X—(CHR³)ₙ—(CR¹R²)ₘ R⁴—N—R⁵ | Y | R⁶ | R⁷ | R⁸ | —Ar | melting point (° C.) (solvent for crystallization) |
|---|---|---|---|---|---|---|---|---|
| 1-056 | 1 | HO₂C—(CH₂)₃—piperidine-N-CH₃ | N | CH₃ | CH₃ | CH₃ | 4-Br-2,6-(CH₃)₂-phenyl | 212-214 (EtOAc) |
| 1-057 | 1 | HO₂C—(CH₂)₃—piperidine-N-CH₃ | N | CH₃ | CH₃ | H | 4-Br-2,6-(CH₃)₂-phenyl | 202-204 (EtOAc) |
| 1-058 | 1 | HO₂C—CH₂—piperidine-N-CH₃ | N | CH₃ | CH₃ | H | 2,4-diBr-phenyl (with Me) | 195-197 (IPE/EtOAc) |
| 1-059 | 1 | HO₂C—(CH₂)₂—piperidine-N-CH₃ | N | CH₃ | CH₃ | H | 2,4-diBr-phenyl (with Me) | 229-231 (THF/EtOAc) |
| 1-060 | 1 | HO₂C—(CH₂)₃—piperidine-N-CH₃ | N | CH₃ | CH₃ | H | 2,4-diBr-phenyl (with Me) | 164-166*2 (EtOAc) |
| 1-061 | 2 | H₂NOC—CH₂—(3,3-diMe-piperidine)-N-CH₃ | N | CH₃ | CH₃ | CH₃ | 4-Br-2,6-(CH₃)₂-phenyl | 248-250 (IPE) |
| 1-062 | 2 | HO₂C—CH(CH₃)—piperidine-N-CH₃ | N | CH₃ | CH₃ | H | 4-Br-2,6-(CH₃)₂-phenyl | 263-265 (IPE) |

TABLE 1*¹-continued
| Com. No. | Ex. No | X—(CHR³)ₙ—(CR¹R²)ₘ / R⁴ / R⁵ | Y | R⁶ | R⁷ | R⁸ | —Ar | melting point (°C.) (solvent for crystallization) |
|---|---|---|---|---|---|---|---|---|
| 1-063 | 8 | 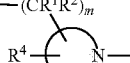 | N | CH₃ | CH₃ | CH₃ | 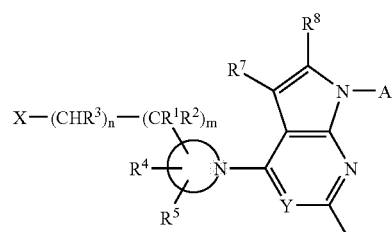 | amorphous |
| 1-064 | 1 | 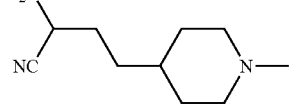 | N | CH₃ | CH₃ | H | 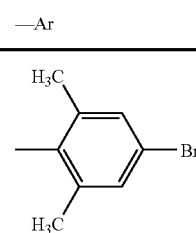 | 178-180*² (EtOAc) |
| 1-065 | 7 | 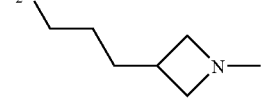 | CH | CH₃ | CH₃ | H | 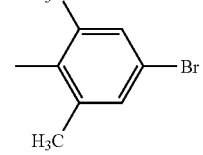 | 183-185 (EtOAc) |
| 1-066 | 7 | 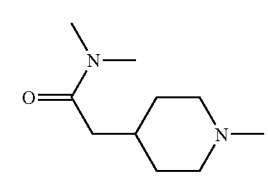 | CH | CH₃ | CH₃ | H | 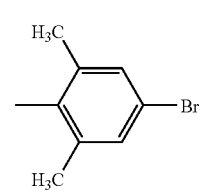 | 184-186 (EtOAc) |
| 1-067 | 5 | 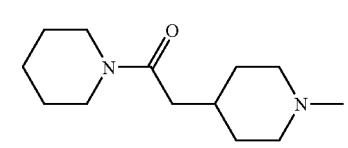 | CH | CH₃ | CH₃ | H | 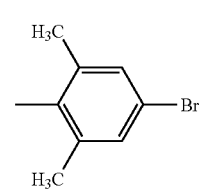 | amorphous |
| 1-068 | 5 | 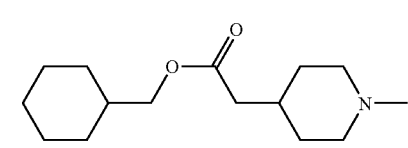 | CH | CH₃ | CH₃ | H | 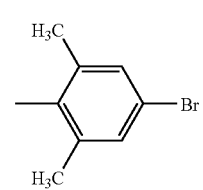 | amorphous |

TABLE 1*¹-continued

| Com. No. | Ex. No | X—(CHR³)ₙ—(CR¹R²)ₘ / R⁴ / R⁵ (N-ring) | Y | R⁶ | R⁷ | R⁸ | —Ar | melting point (°C.) (solvent for crystallization) |
|---|---|---|---|---|---|---|---|---|
| 1-069 | 5 | (CH₃)₂N-CH₂CH₂CH₂-O-C(O)-CH₂-(1-methylpiperidin-4-yl) | CH | CH₃ | CH₃ | H | 4-bromo-2,6-dimethylphenyl | amorphous |
| 1-070 | 5 | (CH₃)₂C=CH-CH₂CH₂-C(CH₃)=CH-CH₂-O-C(O)-CH₂-(1-methylpiperidin-4-yl) | CH | CH₃ | CH₃ | H | 4-bromo-2,6-dimethylphenyl | oil |
| 1-071 | 6 | cyclohexyl-O-C(O)-O-CH(CH₃)-O-C(O)-CH₂-(1-methylpiperidin-4-yl) | CH | CH₃ | CH₃ | H | 4-bromo-2,6-dimethylphenyl | oil |
| 1-072 | 6 | (CH₃)₃C-C(O)-O-CH₂-O-C(O)-CH₂-(1-methylpiperidin-4-yl) | CH | CH₃ | CH₃ | H | 4-bromo-2,6-dimethylphenyl | oil |
| 1-073 | 7 | PhCH₂-CH(CO₂Et)-NH-C(O)-CH₂-(1-methylpiperidin-4-yl) | CH | CH₃ | CH₃ | H | 4-bromo-2,6-dimethylphenyl | oil |
| 1-074 | 7 | PhCH₂-CH(CO₂H)-NH-C(O)-CH₂-(1-methylpiperidin-4-yl) | CH | CH₃ | CH₃ | H | 4-bromo-2,6-dimethylphenyl | 144-146*³ |

TABLE 1*¹-continued
| Com. No. | Ex. No | X—(CHR³)ₙ—(CR¹R²)ₘ / R⁴ / R⁵ | Y | R⁶ | R⁷ | R⁸ | —Ar | melting point (° C.) (solvent for crystallization) |
|---|---|---|---|---|---|---|---|---|
| 1-075 | 6 | 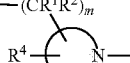 | CH | CH₃ | CH₃ | H | 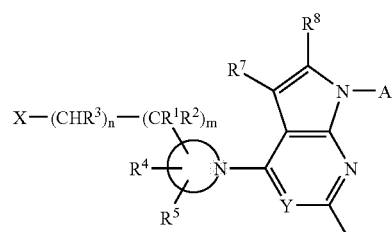 | oil |
| 1-076 | 7 | 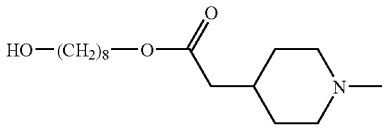 | CH | CH₃ | CH₃ | H | 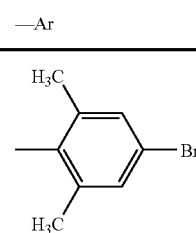 | oil |
| 1-077 | 6 | 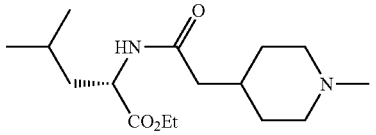 | CH | CH₃ | CH₃ | H | 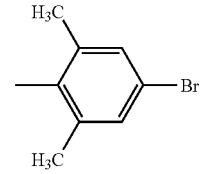 | amorphous |
| 1-078 | 2 | 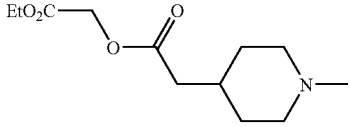 | N | CH₃ | CH₃ | H | 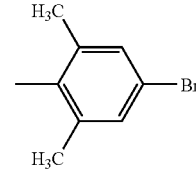 | amorphous |
| 1-079 | 1 | 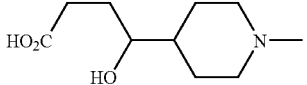 | N | CH₃ | —CH=CH— CH=CH— | | 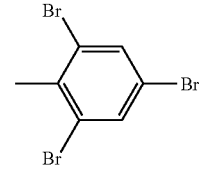 | 256-258 (EtOAc) |
| 1-080 | 1 | 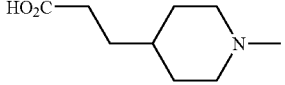 | N | CH₃ | —CH₂—CH₂— CH₂—CH₂— | | 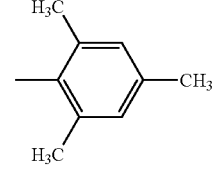 | 238-239 (EtOAc) |

TABLE 1*1-continued

| Com. No. | Ex. No | X—(CHR³)ₙ—(CR¹R²)ₘ / R⁴-N-R⁵ | Y | R⁶ | R⁷ | R⁸ | —Ar | melting point (° C.) (solvent for crystallization) |
|---|---|---|---|---|---|---|---|---|
| 1-081 | 1 | HO₂C-CH₂-(4-piperidinyl, N-methyl) | N | CH₃ | CH₃ | H | 2-CF₃-4,6-dimethylpyrimidin-5-yl | 254-256*3 |
| 1-082 | 1 | HO₂C-(CH₂)₂-(4-piperidinyl, N-methyl) | N | CH₃ | CH₃ | CH₃ | 2-N(Me)₂-4-methylpyridin-5-yl | amorphous |

*1Com. No. = compound number, Ex. No. = example number, solvent for crystallization: EtOAc = ethyl acetate, MeOH = methanol, EtOH = ethanol, IPE = diisopropylether, ET₂O = diethylether THF = tetrahydrofuran
Analytical data of non-crystal compounds are described below.

1-045
MS (ES, Neg): 504 (M − 1)⁻, 506 (M + 1)⁻; NMR (300 MHz, DMSO-d6) δ 1.33-1.69 (4 H, m), 1.75-2.13 (3 H, m), 1.88 (6 H, s), 2.42 (3 H, d, J = 1.1 Hz), 2.47 (3 H, s), 2.80-3.25 (2 H, m), 3.63-3.97 (2 H, m), 6.77 (1 H, br s), 7.19 (1 H, br s), 7.50-7.62 (2 H, m).

1-046
MS (ES, Neg): 518 (M − 1)⁻, 520 (M + 1)⁻; NMR (300 MHz, DMSO-d6) δ 1.18-1.98 (9 H, m), 1.88 (6 H, s), 2.42 (3 H, d, J = 0.9 Hz), 2.80-3.27 (2 H, m), 3.65-3.94 (2 H, m), 6.60-6.85 (1 H, m), 7.08-7.22 (1 H, m), 7.19 (1 H, br s), 7.50-7.62 (2 H, m).

1-047
MS (ES, Neg): 504 (M − 1)⁻, 506 (M + 1)⁻; NMR (300 MHz, DMSO-d6) δ 1.30-2.53 (2 H, m), 1.74-2.15 (3 H, m), 1.84 (6 H, s), 2.32 (3 H, s), 2.43 (3 H, d, J = 1.1 Hz), 2.47 (2 H, d, J = 6.4 Hz), 2.62-2.78 (2 H, m), 3.36-3.52 (2 H, m), 6.47 (1 H, s), 6.94-6.98 (1 H, m), 7.44 (2 H, s).

1-048
MS (ES, Neg): 518 (M − 1)⁻, 520 (M + 1)⁻; NMR (300 MHz, DMSO-d6) δ 1.20-1.87 (7 H, m), 1.84 (6 H, s), 2.40-2.60 (2 H, m), 2.43 (3 H, d, J = 0.9 Hz), 2.49 (3 H, s), 2.60-2.75 (2 H, m), 3.41-3.55 (2 H, m), 6.46 (1 H, s), 6.94-6.97 (1 H, m), 7.44 (2 H, s).

1-063
MS (ES, Pos): 566 (M + 1)⁺, 568 (M + 3)⁺; NMR (300 MHz, CDCl₃) δ 1.28-1.70 (6 H, m), 1.35 (3 H, t, J = 7.1 Hz), 1.72-2.12 (3 H, m), 1.84 (6 H, s), 1.94 (3 H, s), 2.37 (3 H, s), 2.49 (3 H, s), 2.82-3.00 (2 H, m), 3.46-3.55 (1 H, m), 3.90-4.09 (2 H, m), 4.30 (2 H, q, J = 7.1 Hz), 7.33 (2 H, s).

1-067
MS (ES, Pos): 566 (M + 1)⁺, 568 (M + 3)⁺; NMR (300 MHz, CDCl₃) δ 0.90-1.35 (4 H, m), 1.45-1.80 (10 H, m), 1.82-2.05 (2 H, m), 1.92 (6 H, s), 2.36 (2 H, d, J = 7.00 Hz), 2.44 (3 H, s), 2.49 (3 H, s), 2.70-2.85 (2 H, m), 3.52-3.61 (2 H, m), 3.92 (2 H, d, J = 6.37 Hz), 6.43 (1 H, m), 6.59-6.64 (1 H, m), 7.29 (2 H, s).

1-068
MS (ES, Pos): 594 (M + 1)⁺, 596 (M + 3)⁺; NMR (300 MHz, CDCl₃) δ 1.50-1.65 (4 H, m), 1.80-2.00 (1 H, m), 1.92 (6 H, s), 2.41 (2 H, d, J = 7.00 Hz), 2.44 (3 H, s), 2.45-2.49 (3 H, m), 2.70-2.83 (2 H, m), 3.50-3.62 (2 H, m), 5.11 (2 H, s), 6.42 (1 H, m), 6.59-6.64 (1 H, m), 7.25-7.40 (6 H, m).

1-069
MS (ES, Pos): 555 (M + 1)⁺, 557 (M + 3)⁺; NMR (300 MHz, CDCl₃) δ 1.48-1.70 (4 H, m), 1.78-1.95 (3 H, m), 1.92 (6 H, s), 2.25 (6 H, s), 2.36 (2 H, d, J = 7.00 Hz), 2.44 (3 H, s), 2.46-2.50 (3 H, m), 2.70-2.82 (2 H, m), 3.52-3.62 (2 H, m), 6.42 (1 H, m), 6.59-6.63 (1 H, m), 7.29 (2 H, s).

1-070
MS (ES, Pos): 606 (M + 1)⁺, 608 (M + 3)⁺; NMR (200 MHz, CDCl₃) δ 1.42-1.78 (4 H, m), 1.60 (3 H, s), 1.69 (3 H, s), 1.73 (3 H, s), 1.80-1.96 (1 H, m), 1.92 (6 H, s), 2.01-2.18 (4 H, m), 2.36 (2 H, d, J = 6.80 Hz), 2.44 (3 H, s), 2.46-2.51 (3 H, m), 2.68-2.85 (2 H, m), 3.49-3.63 (2 H, m), 4.63 (2 H, d, J = 7.00 Hz), 5.03-5.15 (2 H, m), 5.30-5.42 (2 H, m), 6.42 (1 H, m), 6.58-6.63 (1 H, m), 7.29 (2 H, s).

1-071
MS (ES, Pos): 640 (M + 1)⁺, 642 (M + 3)⁺; NMR (300 MHz, CDCl₃) δ 1.20-1.62 (10 H, m), 1.54 (3 H, d, J = 5.40 Hz), 1.70-1.82 (2 H, m), 1.82-2.04 (3 H, m), 1.92 (6 H, s), 2.37-2.42 (2 H, m), 2.44 (3 H, s), 2.46-2.50 (3 H, m), 2.70-2.82 (2 H, m), 3.49-3.61 (2 H, m), 4.58-4.70 (1 H, m), 6.42 (1 H, s), 6.59-6.63 (1 H, m), 6.80 (1 H, q, J = 5.40 Hz), 7.29 (2 H, s).

1-072
MS (ES, Pos): 584 (M + 1)⁺, 586 (M + 3)⁺; NMR (300 MHz, CDCl₃) δ 1.23 (9 H, s), 1.50-1.65 (4 H, m), 1.82-1.91 (1 H, m), 1.92 (6 H, s), 2.43 (2 H, d, J = 6.99 Hz), 2.45 (3 H, s), 2.46-2.50 (3 H, m), 2.71-2.82 (2 H, m), 3.50-3.61 (2 H, m), 5.79 (2 H, s), 6.42 (1 H, m), 6.59-6.63 (1 H, m), 7.29 (2 H, s).

1-073
MS (ES, Pos): 645 (M + 1)⁺, 647 (M + 3)⁺; NMR (300 MHz, CDCl₃) δ 1.27 (3 H, t, J = 7.15 Hz), 1.40-1.61 (3 H, m), 1.70-1.91 (2 H, m), 1.92 (6 H, s), 2.17-2.23 (2 H, m), 2.45 (3 H, s), 2.46-2.49 (3 H, m), 2.69-2.81 (2 H, m), 3.14-3.23 (2 H, m), 3.48-3.59 (2 H, m), 4.20 (2 H, q, J = 7.15 Hz), 4.91-4.98 (1 H, m), 5.89-5.93 (1 H, m), 6.42 (1 H, m), 6.59-6.63 (1 H, m), 7.10-7.18 (2 H, m), 7.22-7.37 (5 H, m).

1-075
MS (ES, Pos): 598 (M + 1)⁺, 600 (M + 3)⁺; NMR (300 MHz, CDCl₃) δ 1.18-1.43 (9 H, m), 1.50-1.72 (7 H, m), 1.83-2.06 (2 H, m), 1.92 (6 H, s), 2.35 (2 H, d, J = 6.99 Hz), 2.45 (3 H, s), 2.47-2.50 (3 H, m), 2.71-2.84 (2 H, m), 3.50-3.69 (4 H, m), 4.10 (2 H, d, J = 6.68 Hz), 6.42 (1 H, s), 6.60-6.63 (1 H, m), 7.29 (2 H, s).

1-076
MS (ES, Pos): 611 (M + 1)⁺, 613 (M + 3)⁺; NMR (300 MHz, CDCl₃) δ 0.95-1.05 (6 H, m), 1.29 (3 H, t, J = 7.15 Hz), 1.48-1.77 (6 H, m), 1.83-2.18 (2 H, m), 1.92 (6 H, s), 2.25 (2 H, d, J = 6.99 Hz), 2.44 (3 H, s), 2.47-2.50 (3 H, m), 2.70-2.83 (2 H, m), 3.49-3.62 (2 H, m), 4.20 (2 H, q, J = 7.15 Hz), 4.60-4.72 (1 H, m), 5.85 (1 H, d, J = 8.24 Hz), 6.42 (1 H, m), 6.59-6.62 (1 H, m), 7.29 (2 H, s).

1-077
MS (ES, Pos): 556 (M + 1)⁺, 558 (M + 3)⁺; NMR (300 MHz, CDCl₃) δ 1.30 (3 H, t, J = 7.15 Hz), 1.50-1.70 (3 H, m), 1.85-2.15 (2 H, m), 1.92 (6 H, s), 2.40-2.50 (2 H, m), 2.44 (3 H, s), 2.47-2.50 (3 H, m), 2.72-2.84 (2 H, m), 3.52-3.62 (2 H, m), 4.24 (2 H, q, J = 7.15 Hz), 4.64 (2 H, s), 6.43 (1 H, s), 6.59-6.63 (1 H, m), 7.29 (2 H, s).

1-078

TABLE 1*[1]-continued

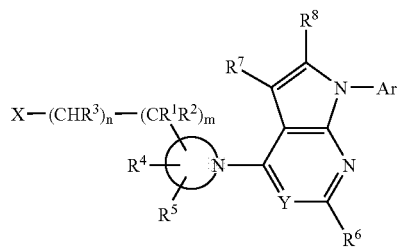

| Com.<br>No. | Ex.<br>No. | X—(CHR³)ₙ—(CR¹R²)ₘ<br>R⁴—⟨N⟩—<br>R⁵ | Y | R⁶ | R⁷ | R⁸ | —Ar | melting point<br>(° C.)<br>(solvent for<br>crystallization) |
|---|---|---|---|---|---|---|---|---|

MS (ES, Pos): 643 (M + 1)⁺, 645 (M + 3)⁺, 647 (M + 5)⁺, 649 (M + 7)⁺; NMR (300 MHz, CDCl₃) δ 1.45-2.05 (9 H, m), 2.43-2.46 (3 H, m), 2.52 (3 H, s), 2.57 (2 H, t, J = 7.07 Hz), 2.82-3.03 (2 H, m), 3.47-3.56 (1 H, m), 4.10-4.25 (2 H, m), 6.59-6.63 (1 H, m), 7.82 (2 H, s).
1-082
MS (ES, Pos): 465 (M + 1)⁺; NMR (300 MHz, CDCl₃) δ 1.20-1.80 (10 H, m), 1.85 (3 H, s), 2.02 (3 H, s), 2.2-2.43 (5 H, m), 2.51 (3 H, m), 2.92-3.03 (2 H, m), 3.13 (6 H, s), 3.91-4.04 (2 H, m), 6.44-6.48 (1 H, m), 7.96 (1 H, s).
*²1 HCl salt
*³The crystal was obtained after standing the compound purified with column chromatography.

TEST EXAMPLE 1

CRF Receptor Binding Test

Monkey amygdala membranes were used as a receptor preparation.
$^{125}$I-CRF was used as $^{125}$I-labeled ligand.
Binding reaction using the $^{125}$I-labeled ligand was carried out by the following method described in The Journal of Neuroscience, 7, 88 (1987).
Preparation of Receptor Membranes:
Monkey amygdala was homogenized in 50 mM Tris-HCl buffer (pH 7.0) containing 10 mM MgCl₂, 2 mM EDTA and centrifuged at 48,000×g for 20 min, and the precipitate was washed once with Tris-HCl buffer. The washed precipitate was suspended in 50 mM Tris-HCl buffer (pH 7.0) containing 10 mM MgCl₂, 2 mM EDTA, 0.1% bovine serum albumin and 100 kallikrein units/ml aprotinin, to obtain a membrane preparation.
CRF Receptor Binding Test:
The membrane preparation (0.3 mg protein/ml), $^{125}$I-CRF (0.2 nM) and a test drug were reacted at 25° C. for 2 hours. After completion of the reaction, the reaction mixture was filtered by suction through a glass filter (GF/C) treated with 0.3% polyethylene imine, and the glass filter was washed three times with phosphate-buffered saline containing 0.01% Triton X-100. After the washing, the radioactivity of the filter paper was measured in a gamma counter.
The amount of $^{125}$I-CRF bound when the reaction was carried out in the presence of 1 μM CRF was taken as the degree of nonspecific binding of $^{125}$I-CRF, and the difference between the total degree of $^{125}$I-CRF binding and the degree of nonspecific $^{125}$I-CRF binding was taken as the degree of specific $^{125}$I-CRF binding. An inhibition curve was obtained by reacting a definite concentration (0.2 nM) of $^{125}$I-CRF with various concentrations of each test drug under the conditions described above. A concentration of the test drug at which binding of $^{125}$I-CRF is inhibited by 50% (IC₅₀) was determined from the inhibition curve.
As a result, it was found that compounds I-001, 1-002, 1-003, 1-004, 1-005, 1-006, 1-007, 1-008, 1-009, 1-010, 1-011, 1-012, 1-014, 1-015, 1-016, 1-017, 1-018, 1-019, 1-020, 1-021, 1-022, 1-023, 1-024, 1-025, 1-026, 1-027, 1-028, 1-029, 1-030, 1-031, 1-032, 1-033, 1-034, 1-035, 1-039, 1-042, 1-045, 1-047, 1-048, 1-049, 1-053, 1-056, 1-061, 1-072, 1-073 can be exemplified as typical compounds having an IC₅₀ value of 100 nM or less.

TEST EXAMPLE 2

δ Receptor Binding Test

Rat Brain Membranes were Used as a Receptor Preparation.
$^{3}$H-DPDPE ([$_{D}$-Pen²,$_{D}$-Pen⁵]-Enkephalin) was used as $^{3}$H-labeled ligand.
Binding reaction using the $^{3}$H-labeled ligand was carried out by the following method.
Preparation of Receptor Membranes:
Rat brain was homogenized in 50 mM Tris-HCl buffer (pH 7.4) containing 10 mM MgCl₂ and 1 mM EDTA, and centrifuged at 48,000×g for 20 min, and the precipitate was washed once with Tris-HCl buffer. The washed precipitate was suspended in 50 mM Tris-HCl buffer (pH 7.4) containing 10 mM MgCl₂ and 1 mM EDTA, to obtain a membrane preparation.
Delta Opioid Receptor Binding Test:
The membrane preparation (1 mg protein/ml), H-DPDPE (1.5 nM) and a test drug were reacted at 25° C. for 70 minutes. After completion of the reaction, the reaction mixture was filtered by suction through a glass filter (GF/B) treated with 0.3% polyethylene imine, and the glass filter was washed three times with 50 mM Tris-HCl buffer (pH 7.4) containing 10 mM MgCl₂ and 1 mM EDTA. After the washing, scintillation cocktail was added to the filters, and the radioactivity of the filter was measured in a liquid scintillation counter.
The amount of $^{3}$H-DPDPE bound when the reaction was carried out in the presence of 10 μM naltrindole was taken as the degree of nonspecific binding of $^{3}$H-DPDPE, and the difference between the total degree of $^{3}$H-DPDPE binding and the degree of nonspecific $^{3}$H-DPDPE binding was taken as the degree of specific $^{3}$H-DPDPE binding. An inhibition curve was obtained by reacting a definite concentration (1.5 nM) of $^{3}$H-DPDPE with various concentrations of each test drug under the conditions described above. A concentration of the test drug at which binding of $^{3}$H-DPDPE is inhibited by 50% (IC₅₀) was determined from the inhibition curve.

As a result, it was found that compounds 1-001, 1-002, 1-003, 1-004, 1-005, 1-006, 1-011, 1-012, 1-016, 1-018, 1-019, 1-020, 1-021, 1-022, 1-025, 1-026, 1-027, 1-032, 1-045, 1-047 and 1-048 can be exemplified as typical compounds having an $IC_{50}$ value of 500 nM or less.

Effect of the Invention

According to the present invention, compounds having a high affinity for CRF receptors and/or δ receptors have been provided. These compounds have excellent pharmacokinetic properties including metabolic stability, bioavailability and brain concentration. These compounds are effective against diseases in which CRF is considered to be involved, such as depression, anxiety, Alzheimer's disease, Parkinson's disease, Huntington's chorea, eating disorder, hypertension, gastrointestinal diseases, drug dependence, cerebral infarction, cerebral ischemia, cerebral edema, cephalic external wound, inflammation, immunity-related diseases, alopecia, irritable bowel syndrome, sleep disorders, epilepsy, dermatitides, schizophrenia, pain, etc.

The invention claimed is:
1. A pyrrolopyrimidine compound substituted with a cyclic amino group represented by the following a [I]:

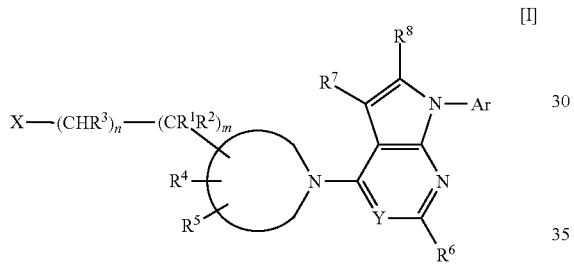

wherein the cyclic amino group is represented by the following a [II]:

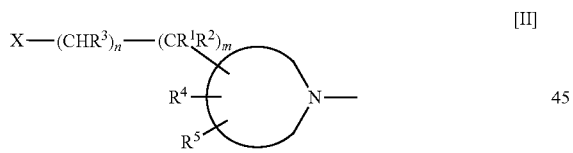

in which the cyclic amino group is a 3- to 8-membered saturated cyclic amine or a 3- to 8-membered saturated cyclic amine bridged with $C_{1-5}$alkylene or $C_{1-4}$alkylene-O-$C_{1-4}$alkylene between any different two carbon atoms of the cyclic amine, which cyclic amine is substituted with a group represented by —$(CR^1R^2)_m$—$(CHR^3)_n$—X, $R^4$ and $R^5$ independently on the same or different carbon atoms of the cyclic amine;

X is —$CO_2R^9$, —$CON(R^{10})R^{11}$, —$P(=O)(R^{12})R^{13}$ or —$S(=O)_kR^{14}$;

Y is N;

$R^1$ is hydrogen, hydroxy, $C_{1-5}$alkyl, $C_{1-5}$alkoxy-$C_{1-5}$alkyl or hydroxy-$C_{1-5}$alkyl;

$R^2$ is hydrogen or $C_{1-5}$alkyl;

$R^3$ is hydrogen, cyano, $C_{1-5}$alkyl, $C_{1-5}$alkoxy-$C_{1-5}$alkyl or hydroxy-$C_{1-5}$alkyl;

m is an integer selected from 0, 1, 2, 3, 4 and 5;

n is 0 or 1;

with the proviso that when X is —$CO_2R^9$ or —$CON(R^{10})R^{11}$, and n is 0, then m is an integer selected from 1, 2, 3, 4 and 5;

$R^4$ is hydrogen, hydroxy, hydroxy-$C_{1-5}$alkyl, cyano, cyano-$C_{1-5}$alkyl or $C_{1-5}$alkyl;

$R^5$ is hydrogen or $C_{1-5}$alkyl;

$R^6$ is hydrogen, halogen, $C_{1-5}$alkyl, $C_{3-8}$cycloalkyl, $C_{3-8}$cycloalkyl-$C_{1-5}$alkyl, hydroxy, $C_{1-5}$alkoxy, $C_{3-8}$cycloalkyloxy or —$N(R^{16})R^{17}$;

$R^7$ and $R^8$ are the same or different, and independently are hydrogen, halogen, $C_{1-5}$alkyl, $C_{3-8}$cycloalkyl, $C_{3-8}$cycloalkyl-$C_{1-5}$alkyl, hydroxy, $C_{1-5}$alkoxy, $C_{3-8}$cycloalkyloxy, —$N(R^{18})R^{19}$, —$CO_2R^{20}$, cyano, nitro, $C_{1-5}$alkylthio, trifluoromethyl or trifluoromethoxy;

$R^9$ is hydrogen, $C_{1-20}$alkyl, aryl, $C_{3-8}$cycloalkyl or —$CHR^{1a}OC(=O)$-$A^1$-$R^{1b}$, wherein said $C_{1-20}$alkyl optionally contains one to four double bonds and/or one to four triple bonds, and/ or said $C_{1-20}$alkyl is optionally substituted with one of the substituents selected from the group consisting of hydroxy, halogen, cyano, $C_{1-10}$alkoxy, $C_{1-5}$alkoxycarbonyl, $C_{3-8}$cycloalkyl, —$C(=O)N(R^{2a})R^{2b}$, —$N(R^{3a})R^{3b}$ and aryl which aryl is optionally substituted with one or more substituents, which are the same or different, selected from the group consisting of halogen, $C_{1-5}$alkyl and $C_{1-5}$alkoxy;

$R^{1a}$ is hydrogen or $C_{1-5}$alkyl;

$A^1$ is oxygen or a single bond;

$R^{1b}$ is $C_{1-5}$alkyl, $C_{3-8}$cycloalkyl or $C_{3-8}$cycloalkyl-$C_{1-5}$alkyl;

$R^{2a}$ and $R^{2b}$ are the same or different, and independently hydrogen or $C_{1-3}$alkyl;

$R^{3a}$ and $R^{3b}$ are the same or different, and independently hydrogen or $C_{1-3}$alkyl; or $R^{3a}$ and $R^{3b}$ are taken together to form —$(CH_2)_s$-$A^2$-$(CH_2)_t$—;

$A^2$ is methylene, oxygen, sulfur, $NR^{4a}$ or a single bond;

$R^{4a}$ is hydrogen, $C_{1-5}$alkyl or benzyl;

s and t are the same or different, and independently an integer selected from 1, 2 or 3;

$R^{10}$ is hydrogen, $C_{1-5}$alkyl, $C_{3-8}$cycloalkyl or $C_{3-8}$cycloalkyl-$C_{1-5}$alkyl;

$R^{11}$ is hydrogen, $C_{1-5}$alkyl, $C_{3-8}$cycloalkyl, $C_{3-8}$cycloalkyl-$C_{1-5}$alkyl or —$CHR^{5a}$—$(CH_2)_u$—$C(=O)R^{5b}$ or $R^{10}$ and $R^{11}$ are taken together to form —$(CH_2)_v$-$A^3$-$(CH_2)_w$—;

$R^{5a}$ is hydrogen, $C_{1-5}$alkyl, aryl or heteroaryl, wherein said $C_{1-5}$alkyl is optionally substituted with one of the substituents selected from the group consisting of aryl, heteroaryl, hydroxy, hydroxycarbonyl, 4-hydroxyphenyl, $C_{1-5}$alkoxy, amino, guanidino, mercapto, $C_{1-5}$alkylthio or aminocarbonyl or $R^{10}$ and $R^{5a}$ are taken together to form —$(CH_2)_p$—;

p is 3 or 4;

u is 0 or 1;

$R^{5b}$ is hydroxy, $C_{1-5}$alkoxy, benzyloxy or —$N(R^{6a})R^{6b}$;

$R^{6a}$ and $R^{6b}$ are the same or different, and independently hydrogen or $C_{1-3}$alkyl;

v and w are the same or different, and independently an integer selected from 1, 2 or 3;

$A^3$ is methylene, oxygen, sulfur or $NR^{7a}$;

$R^{7a}$ is hydrogen, $C_{1-5}$alkyl or benzyl;

$R^{12}$ and $R^{13}$ are the same or different, and independently are —$OR^{21}$ or —$N(R^{22})R^{23}$;

$R^{14}$ is —$OR^{21}$ or —$N(R^{22})R^{23}$;

k is 1 or 2;

R$^{16}$ and R$^{17}$ are the same or different, and independently are hydrogen, C$_{1-5}$alkyl, C$_{3-8}$cycloalkyl or C$_{3-8}$cycloalkyl-C$_{1-5}$alkyl;

R$^{18}$ and R$^{19}$ are the same or different, and independently are hydrogen, C$_{1-5}$alkyl, C$_{3-8}$cycloalkyl or C$_{3-8}$cycloalkyl-C$_{1-5}$alkyl;

R$^{20}$ is hydrogen or C$_{1-5}$alkyl;

R$^{21}$ is hydrogen, C$_{1-5}$alkyl, C$_{3-8}$cycloalkyl or C$_{3-8}$cycloalkyl-C$_{1-5}$alkyl;

R$^{22}$ and R$^{23}$ are the same or different, and independently are hydrogen, C$_{1-5}$alkyl, C$_{3-8}$cycloalkyl or C$_{3-8}$cycloalkyl-C$_{1-5}$alkyl;

Ar is aryl or heteroaryl which aryl or heteroaryl is unsubstituted or substituted with one or more substituents, which are the same or different, selected from the group consisting of halogen, C$_{1-5}$alkyl, C$_{3-8}$cycloalkyl, C$_{2-5}$alkenyl, C$_{2-5}$alkynyl, C$_{1-5}$alkoxy, C$_{1-5}$alkylthio, C$_{1-5}$alkylsulfinyl, C$_{1-5}$alkylsulfonyl, cyano, nitro, hydroxy, —CO$_2$R$^{25}$—C(=O)R$^{26}$, —CON(R$^{27}$)R$^{28}$, —OC(=O)R$^{29}$, —NR$^{30}$CO$_2$R$^{31}$, —S(O)$_r$N(R$^{32}$)R$^{33}$, trifluoromethyl, trifluoromethoxy, difluoromethoxy, fluoromethoxy, methylenedioxy, ethylenedioxy and —N(R$^{34}$)R$^{35}$;

R$^{25}$ is hydrogen, C$_{1-5}$alkyl, C$_{3-8}$cycloalkyl or C$_{3-8}$cycloalkyl-C$_{1-5}$alkyl;

R$^{26}$ is hydrogen or C$_{1-5}$alkyl;

R$^{27}$ and R$^{28}$ are the same or different, and independently are hydrogen, C$_{1-5}$alkyl, C$_{3-8}$cycloalkyl or C$_{3-8}$cycloalkyl-C$_{1-5}$alkyl;

R$^{29}$ is hydrogen or C$_{1-5}$alkyl;

R$^{30}$ is hydrogen or C$_{1-5}$alkyl;

R$^{31}$ is hydrogen or C$_{1-5}$alkyl;

R$^{32}$ and R$^{33}$ are the same or different, and independently are hydrogen, C$_{1-5}$alkyl, C$_{3-8}$cycloalkyl or C$_{3-8}$cycloalkyl-C$_{1-5}$alkyl;

r is 1 or 2;

R$^{34}$ and R$^{35}$ are the same or different, and independently are hydrogen, C$_{1-5}$alkyl, C$_{3-8}$cycloalkyl or C$_{3-8}$cycloalkyl-C$_{1-5}$alkyl, N-oxides thereof, or pharmaceutically acceptable salts thereof.

2. A pyrrolopyrimidine compound substituted with a cyclic amino group represented by the following a [I]:

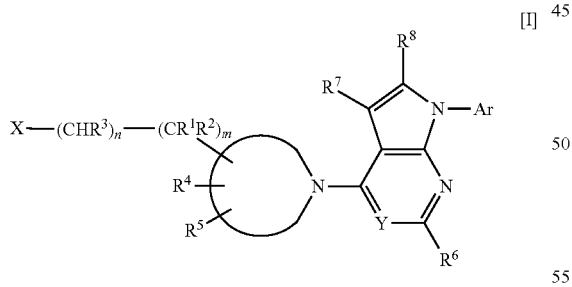

wherein the cyclic amino group is represented by the following a [II]:

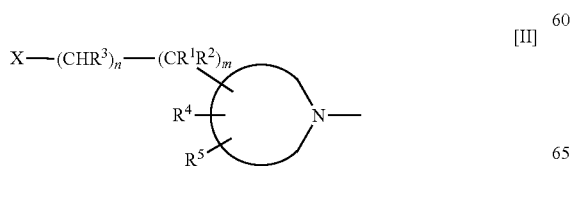

in which the cyclic amino group is a 3- to 8-membered saturated cyclic amine or a 3- to 8-membered saturated cyclic amine bridged with C$_{1-5}$alkylene or C$_{1-4}$alkylene-O—C$_{1-4}$-alkylene between any different two carbon atoms of the cyclic amine, which cyclic amine is substituted with a group represented by —(CR$^1$R$^2$)$_m$—(CHR$^3$)$_n$—X, R$^4$ and R$^5$ independently on the same or different carbon atoms of the cyclic amine;

X is —CO$_2$R$^9$, —CON(R$^{10}$)R$^{11}$, —P(=O)(R$^{12}$)R$^{13}$ or —S(=O)$_k$R$^{14}$;

Y is N;

R$^1$ is hydrogen, hydroxy, C$_{1-5}$alkyl, C$_{1-5}$alkoxy-C$_{1-5}$alkyl or hydroxy-C$_{1-5}$alkyl;

R$^2$ is hydrogen or C$_{1-5}$alkyl;

R$^3$ is hydrogen, cyano, C$_{1-5}$alkyl, C$_{1-5}$alkoxy-C$_{1-5}$alkyl or hydroxy-C$_{1-5}$alkyl;

m is an integer selected from 0, 1, 2, 3, 4 and 5;

n is 0 or 1;

with the proviso that when X is —CO$_2$R$^9$ or —CON(R$^{10}$) R$^{11}$, and n is 0, then m is an integer selected from 1, 2, 3, 4 and 5;

R$^4$ is hydrogen, hydroxy, hydroxy-C$_{1-5}$alkyl, cyano, cyano-C$_{1-5}$alkyl or C$_{1-5}$alkyl;

R$^5$ is hydrogen or C$_{1-5}$alkyl;

R$^6$ is hydrogen, C$_{1-5}$alkyl, C$_{3-8}$cycloalkyl, C$_{3-8}$cycloalkyl-C$_{1-5}$alkyl, hydroxy, C$_{1-5}$alkoxy, C$_{3-8}$cycloalkyloxy or —N(R$^{16}$)R$^{17}$;

R$^7$ and R$^8$ are the same or different, and independently are hydrogen, halogen, C$_{1-5}$alkyl, C$_{3-8}$cycloalkyl, C$_{3-8}$cycloalkyl-C$_{1-5}$alkyl, hydroxy, C$_{1-5}$alkoxy, C$_{3-8}$cycloalkyloxy, —N(R$^{18}$)R$^{19}$, —CO$_2$R$^{20}$, cyano, nitro, C$_{1-5}$alkylthio, trifluoromethyl or trifluoromethoxy;

R$^9$ is hydrogen, C$_{1-10}$alkyl, C$_{3-8}$cycloalkyl or C$_{3-8}$cycloalkyl-C$_{1-5}$alkyl;

R$^{10}$ and R$^{11}$ are the same or different, and independently are hydrogen, C$_{1-5}$alkyl, C$_{3-8}$cycloalkyl or C$_{3-8}$cycloalkyl-C$_{1-5}$alkyl;

R$^{12}$ and R$^{13}$ are the same or different, and independently are —OR$^{21}$ or —N(R$^{22}$)R$^{23}$;

R$^{14}$ is —OR$^{21}$ or —N(R$^{22}$)R$^{23}$;

k is 1 or 2;

R$^{16}$ and R$^{17}$ are the same or different, and independently are hydrogen, C$_{1-5}$alkyl, C$_{3-8}$cycloalkyl or C$_{3-8}$cycloalkyl-C$_{1-5}$alkyl;

R$^{18}$ and R$^{19}$ are the same or different, and independently are hydrogen, C$_{1-5}$alkyl, C$_{3-8}$cycloalkyl or C$_{3-8}$cycloalkyl-C$_{1-5}$alkyl;

R$^{20}$ is hydrogen or C$_{1-5}$alkyl;

R$^{21}$ is hydrogen, C$_{1-5}$alkyl, C$_{3-8}$cycloalkyl or C$_{3-8}$cycloalkyl-C$_{1-5}$alkyl;

R$^{22}$ and R$^{23}$ are the same or different, and independently are hydrogen, C$_{1-5}$alkyl, C$_{3-8}$cycloalkyl or C$_{3-8}$cycloalkyl-C$_{1-5}$alkyl;

Ar is aryl or heteroaryl which aryl or heteroaryl is unsubstituted or substituted with 1 or more substituents, which are the same or different, selected from the group consisting of halogen, C$_{1-5}$alkyl, C$_{3-8}$cycloalkyl, C$_{2-5}$alkenyl, C$_{2-5}$alkynyl, C$_{1-5}$alkoxy, C$_{1-5}$alkylthio, C$_{1-5}$alkylsulfinyl, C$_{1-5}$alkylsulfonyl, cyano, nitro, hydroxy, —CO$_2$R$^{25}$, C(=O)R$^{26}$, —CON(R$^{27}$)R$^{28}$, —OC(=O)R$^{29}$, —NR$^3$CO$_2$R$^{31}$, —S(O)$_r$N(R$^{32}$)R$^{33}$, trifluoromethyl, trifluoromethoxy, difluoromethoxy, fluoromethoxy, methylenedioxy, ethylenedioxy and —N(R$^{34}$)R$^{35}$;

R$^{25}$ is hydrogen, C$_{1-5}$alkyl, C$_{3-8}$cycloalkyl or C$_{3-8}$cycloalkyl-C$_{1-5}$alkyl;

$R^{26}$ is hydrogen or $C_{1-5}$alkyl;

$R^{27}$ and $R^{28}$ are the same or different, and independently are hydrogen, $C_{1-5}$alkyl, $C_{3-8}$cycloalkyl or $C_{3-8}$cycloalkyl-$C_{1-5}$alkyl;

$R^{29}$ is hydrogen or $C_{1-5}$alkyl;

$R^{30}$ is hydrogen or $C_{1-5}$alkyl;

$R^{31}$ is hydrogen or $C_{1-5}$alkyl;

$R^{32}$ and $R^{33}$ are the same or different, and independently are hydrogen, $C_{1-5}$alkyl, $C_{3-8}$cycloalkyl or $C_{3-8}$cycloalkyl-$C_{1-5}$alkyl;

r is 1 or 2;

$R^{34}$ and $R^{35}$ are the same or different, and independently are hydrogen, $C_{1-5}$alkyl, $C_{3-8}$cycloalkyl or $C_{3-8}$cycloalkyl-$C_{1-5}$alkyl, N-oxides thereof, or pharmaceutically acceptable salts thereof.

3. The pyrrolopyrimidine compound substituted with the cyclic amino group according to claim 2 represented by a [I], wherein Y is N; m is an integer selected from 1, 2, 3, 4 and 5; n is 0; $R^1$, $R^2$, $R^4$ and $R^5$ are hydrogen; X, the cyclic amino group, $R^6$, $R^7$, $R^8$ and Ar are as defined in claim 2; or pharmaceutically acceptable salts thereof.

4. The pyrrolopyrimidine compound substituted with the cyclic amino group according to claim 2 represented by a [I], wherein X is as defined in claim 2; Y is N; the cyclic amino group is a 4- to 7-membered saturated cyclic amine; m is an integer selected from 1, 2 and 3; n is 0; $R^1$, $R^2$, $R^4$ and $R^5$ are hydrogen; $R^6$ is $C_{1-5}$alkyl; $R^7$ and $R^8$ are the same or different, and independently are hydrogen or $C_{1-5}$alkyl; Ar is phenyl which phenyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —N($R^{34}$)$R^{35}$ wherein $R^{34}$ and $R^{35}$ are the same or different, and independently are hydrogen or $C_{1-3}$alkyl; or pharmaceutically acceptable salts thereof.

5. The pyrrolopyrimidine compound substituted with the cyclic amino group according to claim 2 represented by a [I], wherein X is —CO$_2$H, —CONH$_2$, —P(=O)(OH)$_2$ or —S(=O)$_2$OH; Y is N; the cyclic amino group is a 6-membered saturated cyclic amine; m is an integer selected from 1, 2 and 3; n is 0; $R^1$, $R^2$, $R^4$ and $R^5$ are hydrogen; $R^6$ is $C_{1-3}$alkyl; $R^7$ and $R^8$ are the same or different, and independently are hydrogen or $C_{1-3}$alkyl; Ar is phenyl which phenyl is substituted with two or three substituents, which are the same or different, selected from the group consisting of chloro, bromo, $C_{1-3}$alkyl, $C_{1-3}$alkoxy, $C_{1-3}$alkylthio, trifluoromethyl, trifluoromethoxy and dimethylamino; or pharmaceutically acceptable salts thereof.

6. The pyrrolopyrimidine compound substituted with the cyclic amino group according to claim 2 represented by a [I], wherein X is —CO$_2$H; Y is N; the cyclic amino group is a 6-membered saturated cyclic amine; m is an integer selected from 1, 2 and 3; n is 0; $R^1$, $R^2$, $R^4$ and $R^5$ are hydrogen; $R^6$ is methyl; $R^7$ and $R^8$ are the same or different, and independently are hydrogen or methyl; Ar is phenyl which phenyl is substituted with two or three substituents, which are the same or different, selected from the group consisting of chloro, bromo, $C_{1-3}$alkyl, $C_{1-3}$alkoxy, $C_{1-3}$alkylthio and trifluoromethyl; or pharmaceutically acceptable salts thereof.

7. The pyrrolopyrimidine substituted with the cyclic amino group represented by a [1] according to claim 1, which compounds are selected from the group consisting of 1-[7-(4-bromo-2,6-dimethyl-phenyl)-2,5,6-trimethyl-7H-pyrrolo[2,3-d]pyrimidin-4-yl]-piperidin-4-yl]-acetic acid, {1-[7-(4-bromo-2,6-dimethyl-phenyl)-2,5-dimethyl-7H-pyrrolo[2,3-d]pyrimidin-4-yl]-piperidin-4-yl}-acetic acid, 3-{1-[7-(4-bromo-2,6-dimethyl-phenyl)-2,5,6-trimethyl-7H-pyrrolo[2,3-d]pyrimidin-4-yl]-piperidin-4-yl}-propionic acid, 3-{1-[7-(4-bromo-2,6-dimethyl-phenyl)-2,5-dimethyl-7H-pyrrolo[2,3-d]pyrimidin-4-yl]-piperidin-4-yl}-propionic acid, {1-[7-(4-isopropyl-2-methylsulfanyl-phenyl)-2,5-dimethyl-7H-pyrrolo[2,3-d]pyrimidin-4-yl]-piperidin-4-yl}-acetic acid, 4-{1-[7-(4-bromo-2,6-dimethyl-phenyl)-2,5,6-trimethyl-7H-pyrrolo[2,3-d]pyrimidin-4-yl]-piperidin-4-yl}-butyric acid, and 2-{1-[7-(4-bromo-2,6-dimethyl-phenyl)-2,5,6-trimethyl-7H-pyrrolo[2,3-d]pyrimidin-4-yl]-3,3-dimethyl-piperidin-4-yl}-acetamide, 8. An antagonist for corticotropin releasing factor (CRF) receptors, comprising a pyrrolopyrimidine compound substituted with a cyclic amino group, or a pharmaceutically acceptable salt thereof according to claim 1 or 2, as an active ingredient.

\* \* \* \* \*

UNITED STATES PATENT AND TRADEMARK OFFICE
CERTIFICATE OF CORRECTION

| | | |
|---|---|---|
| PATENT NO. | : 7,951,811 B2 | Page 1 of 1 |
| APPLICATION NO. | : 11/630042 | |
| DATED | : May 31, 2011 | |
| INVENTOR(S) | : Atsuro Nakazato et al. | |

It is certified that error appears in the above-identified patent and that said Letters Patent is hereby corrected as shown below:

In claim 3 at column 75, line 18:
after represented by a - should read by formula In claim 4 at column 75, line 24:
after represented by a - should read by formula In claim 5 at column 75, line 39:
after represented by a - should read by formula In claim 7 at column 76, line 18:
after represented by a - should read by formula Signed and Sealed this
Twenty-ninth Day of November, 2011

David J. Kappos
*Director of the United States Patent and Trademark Office*